US009702824B2

United States Patent
Cong et al.

(10) Patent No.: US 9,702,824 B2
(45) Date of Patent: Jul. 11, 2017

(54) PH SENSORS

(71) Applicant: PROMEGA CORPORATION, Madison, WI (US)

(72) Inventors: Mei Cong, Madison, WI (US); Cesear Corona, Paso Robles, CA (US); Mark G. McDougall, Arroyo Grande, CA (US); Chad Zimprich, Stoughton, WI (US)

(73) Assignee: PROMEGA CORPORATION, Madison, WI (US)

( * ) Notice: Subject to any disclaimer, the term of this patent is extended or adjusted under 35 U.S.C. 154(b) by 156 days.

(21) Appl. No.: 14/384,081

(22) PCT Filed: Mar. 8, 2013

(86) PCT No.: PCT/US2013/029956
§ 371 (c)(1),
(2) Date: Sep. 9, 2014

(87) PCT Pub. No.: WO2013/134686
PCT Pub. Date: Sep. 12, 2013

(65) Prior Publication Data
US 2015/0044776 A1    Feb. 12, 2015

Related U.S. Application Data

(60) Provisional application No. 61/608,805, filed on Mar. 9, 2012.

(51) Int. Cl.
*G01N 31/16* (2006.01)
*G01N 21/80* (2006.01)
(Continued)

(52) U.S. Cl.
CPC .............. *G01N 21/80* (2013.01); *C09B 11/24* (2013.01); *C09B 11/28* (2013.01); *G01N 31/221* (2013.01); *G01N 2021/7786* (2013.01)

(58) Field of Classification Search
None
See application file for complete search history.

(56) References Cited

U.S. PATENT DOCUMENTS 6,130,101 A    10/2000  Mao et al.
7,238,842 B2   7/2007   Wood et al.
(Continued)

FOREIGN PATENT DOCUMENTS

| CN | 102659744 | 9/2012 |
|----|-----------|--------|
| JP | 2014-185083 | 10/2014 |

(Continued)

OTHER PUBLICATIONS

Aigner et al., New fluorescent pH sensors based on covalently linkable PET rhodamines, Talanta, 2012, 99:194-201.
(Continued)

*Primary Examiner* — Robert Xu
(74) *Attorney, Agent, or Firm* — Casimir Jones SC; David W. Staple

(57) ABSTRACT

Provided herein are fluorescent sensor agents, and methods of use and manufacture thereof. In particular, sensor agents are provided that exhibit a detectable change in fluorescence (e.g., fluorescence intensity) upon alteration of the pH of the surrounding environment (e.g., upon moving from one pH environment to another).

12 Claims, 49 Drawing Sheets

(51) Int. Cl.
*G01N 31/22* (2006.01)
*C09B 11/24* (2006.01)
*C09B 11/28* (2006.01)
*G01N 21/77* (2006.01)

(56) References Cited

U.S. PATENT DOCUMENTS

| | | |
|---|---|---|
| 7,425,436 B2 | 9/2008 | Darzins et al. |
| 7,867,726 B2 | 1/2011 | Wood et al. |
| 7,888,086 B2 | 2/2011 | Darzins et al. |
| 7,935,803 B2 | 5/2011 | Darzins et al. |
| 8,461,358 B2 | 6/2013 | Nagano et al. |
| 9,040,674 B2 | 5/2015 | Benson et al. |
| 2008/0274907 A1 | 11/2008 | Beacham et al. |

FOREIGN PATENT DOCUMENTS

| | | |
|---|---|---|
| WO | 93/06868 | 4/1993 |
| WO | 94/08629 | 4/1994 |
| WO | 94/09056 | 4/1994 |
| WO | 96/26754 | 9/1994 |
| WO | 2010/091126 | 8/2010 |
| WO | 2013/134686 | 9/2013 |

OTHER PUBLICATIONS

Asanuma et al., Acidic-pH-Activatable Fluorescence Probes for Visualizing Exocytosis Dynamics, Angewandte Chemi International, 2014, 53:6085-6089.

Bojinov et al., Synthesis and energy-transfer properties of fluorescence sensing bichromophoric system based on Rhdamine 6G and 1,8-naphthalimide, Sensors and Actuators B: Chemical, 2009, 143:42-49.

Georgiev et al., Selective ratiometric pH-sensing PAMAM light-harvesting dendrimer basedon Rhodamine 6G and 1,8-naphthalimide, Journal of Photochemistry and Photobiology A: Chemistry, 277:62-74.

Grimm et al., Synthesis of Rhodamines from Fluoresceins Using Pd-Catalyzed C-N Cross-Coupling, Organic Letters, 2011, 13:6354-6357.

Kierat et al., A fluorescent redox sensor with tuneable oxidation potential, Bioorganic & Medicinal Chemistry Letters, 2010, 20:1457-1459.

Kim et al., Study on various fluorescein derivatives as pH sensors, Tetrahedron Lett, 2011, 52:2340-2343.

Koide et al., Scalable and Concise Synthesis of Dicholorofluorescein Derivatives Displaying Tissue Permeation in Live Zebrafish Embryos, ChemBiochem, 2008, 9:214-218.

Liu et al., One-pot synthesis of a new rhodamine-based dually-responsive pH sensor and its application to bioimaging, Tetrahedron, 2014, 70:6974-6979.

Madsen et al., Syntheis of Rhodamine 6G-Based Compounds for the ATRP Synthesis of Fluorescently Labeled Biocompatible Polymers, Biomacromolecules, 2011, 12:2225-2234.

Scheucher et al., Magnetic Optical Sensor Particles for pH Measurement, AIP Conference Proceedings, 2010, p. 15-19.

Tan et al., A novel "off-on" colorimetric and fluorescent rhodamine-based pH chemosensor for extreme acidity, Spectrochimica Acta Part A: Molecular and Biomolecular Sepctroscopy, 2015, 140:489-494.

Tomalia et al., Starburst Dendrimers: Molecular-Level Control of Size, Shape, Surface Chemistry, Topology, and Flexibility from Atoms to Macroscopic Matter, Angew. Chem. Int. Ed. Engl. 29:138-175 (1990).

Yuan et al., Development of FRET-Based Dueal-Excitation Ratiometric Fluorescent pH Probes and Their Photocaged Derivatives, Chem Eur J, 2012, 18:1247-1255.

Extended European Search Report for EP 13757114.7, mailed Jul. 23, 2015, 14 pages.

International Search Report and Written Opinion for PCT/US2013/029956, mailed Jun. 10, 2013, 12 pages.

FIG. 1
A) 4453
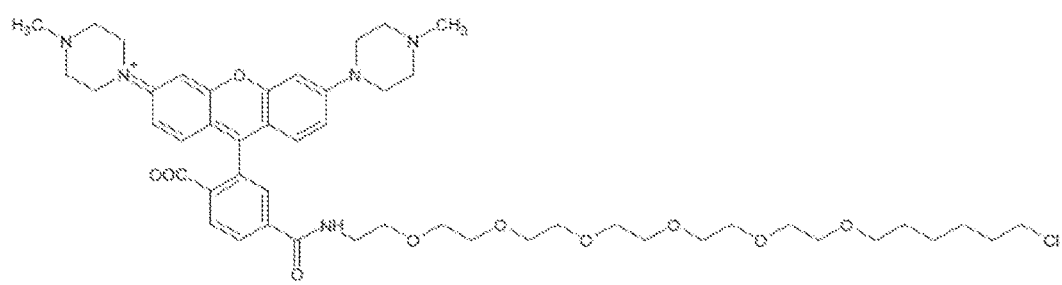
B) 4479
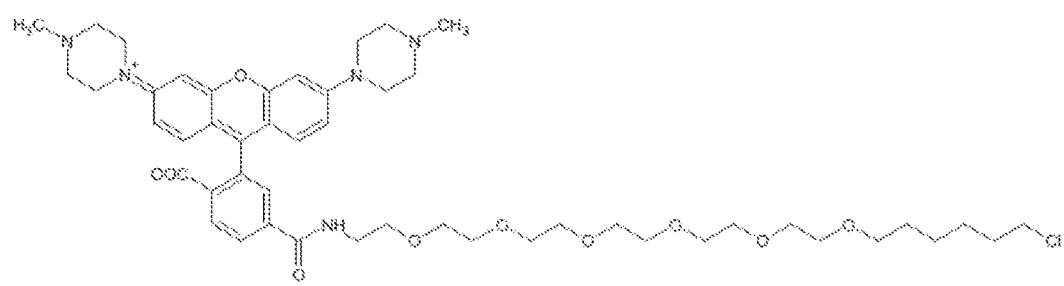
C) 4959
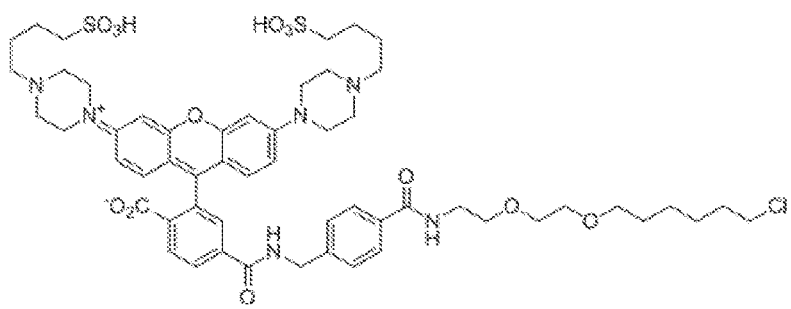

FIG. 1 (cont.)
D) 5004
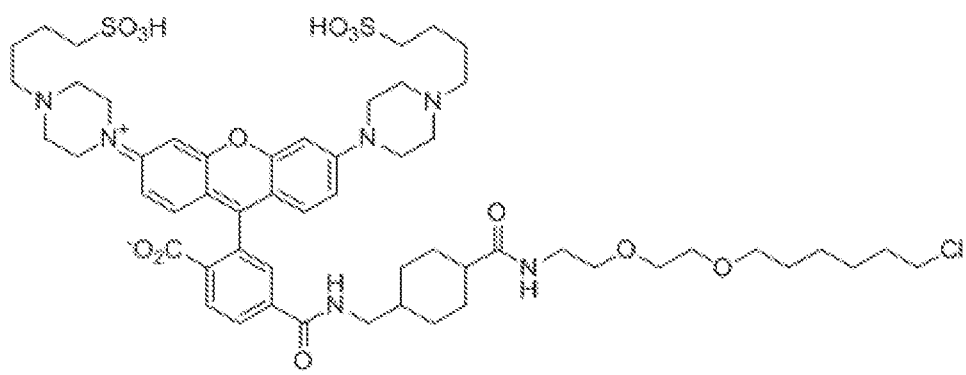
E) 5183
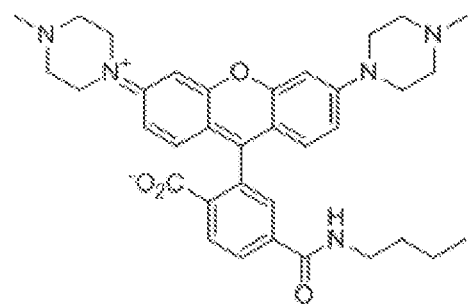

FIG. 2
A)
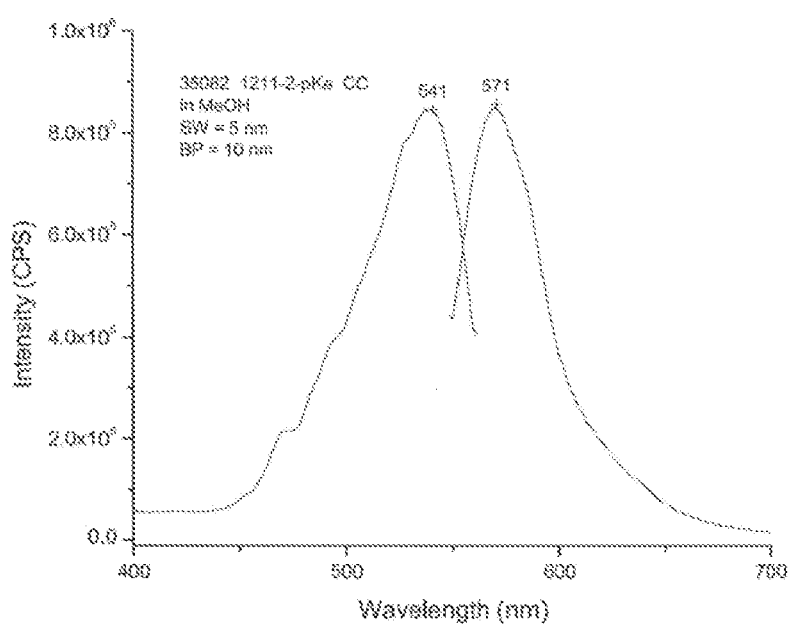
B)
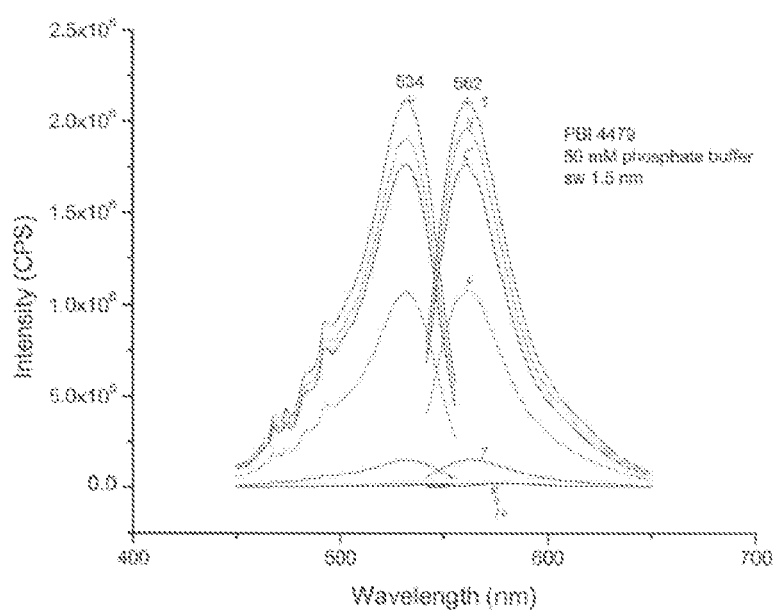

FIG. 3
A)
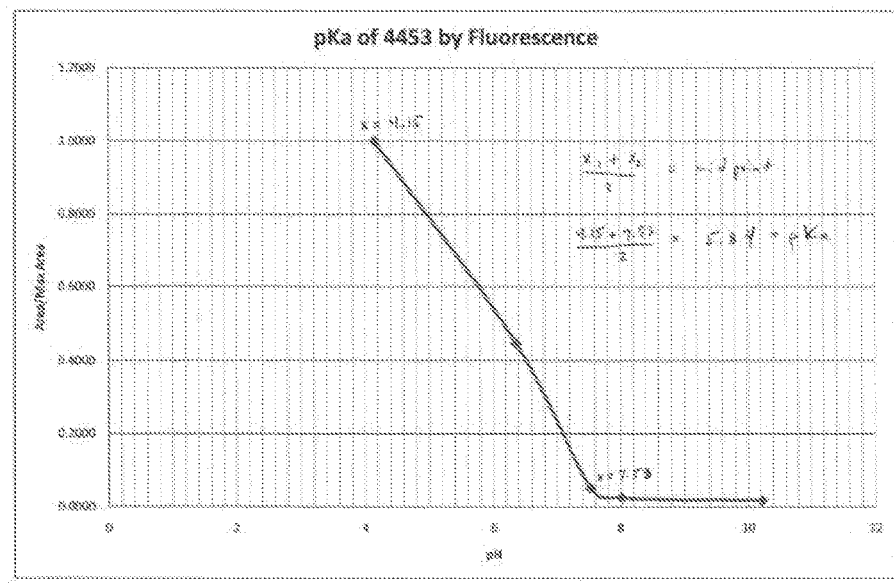
B)
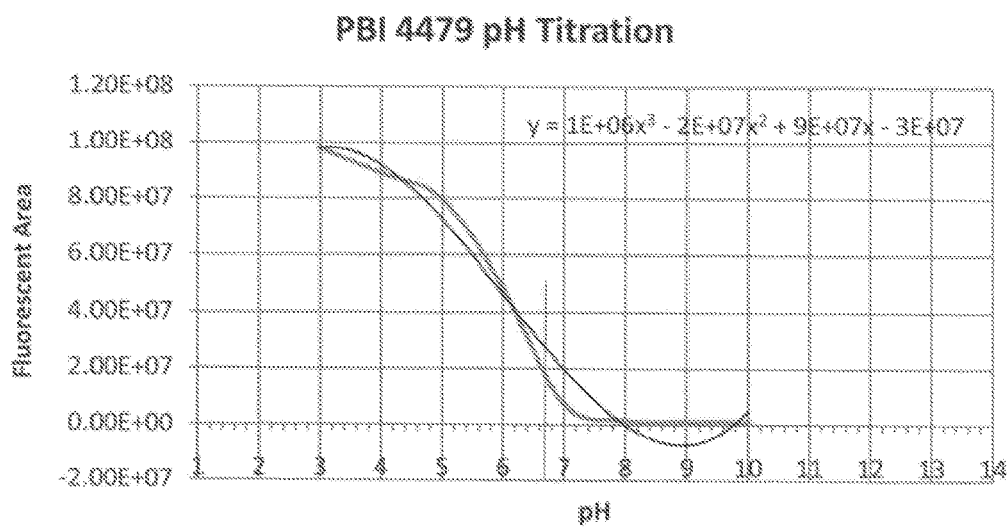

FIG. 3 (cont.)
C)
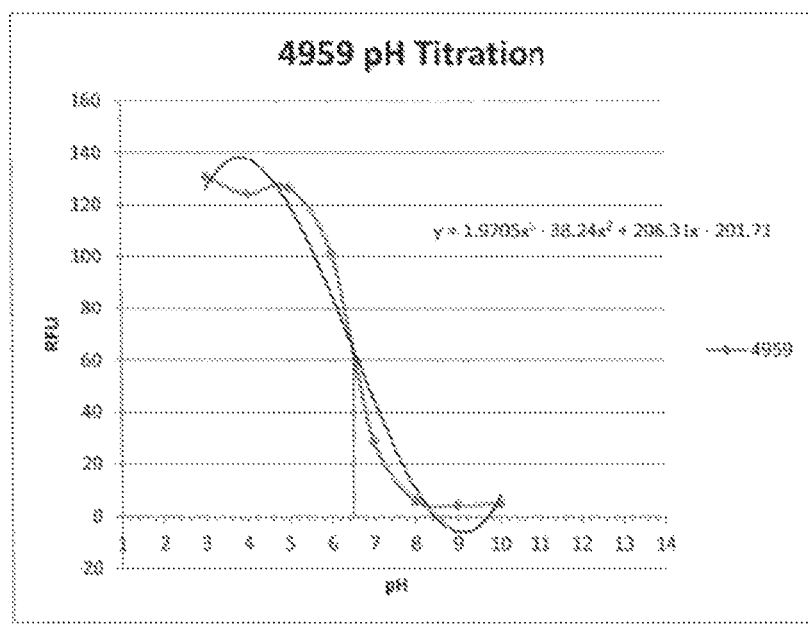
D)
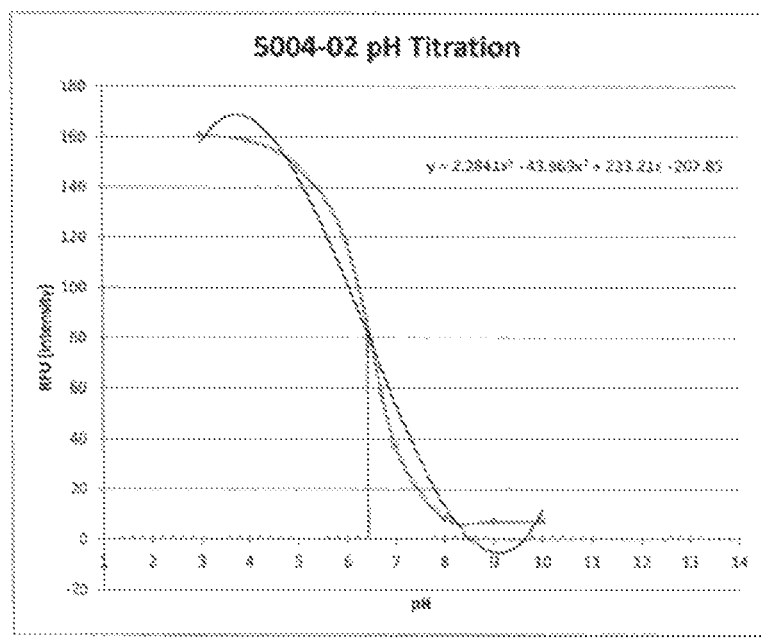

E)

FIG. 44
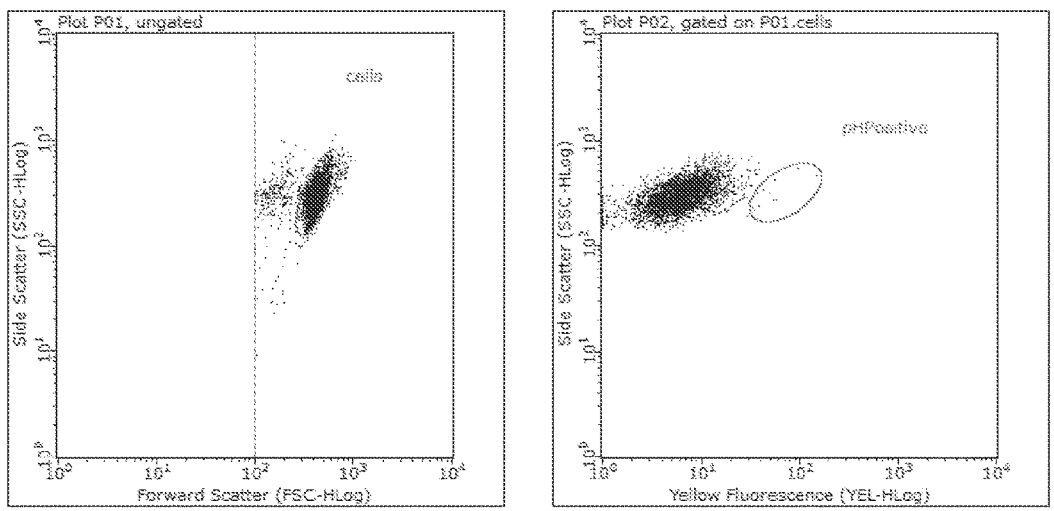
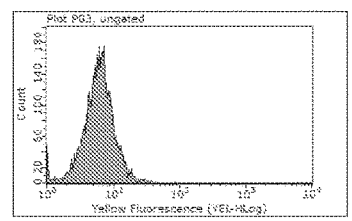

FIG. 45
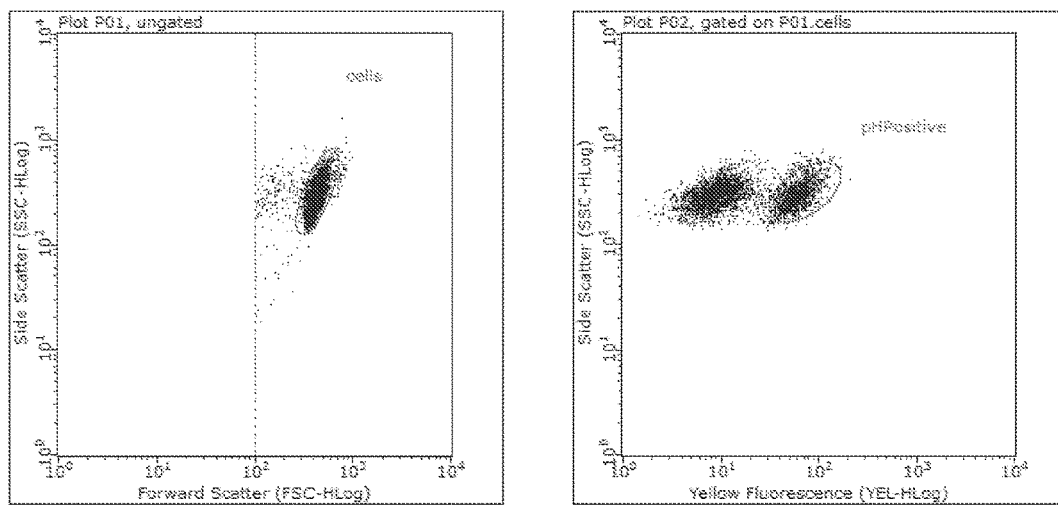
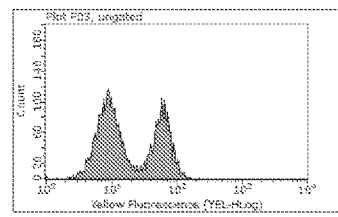

PH SENSORS

CROSS REFERENCE TO RELATED APPLICATIONS

This Application claims priority to U.S. Provisional Patent Application Ser. No. 61/608,805, filed Mar. 9, 2012, hereby incorporated by reference in its entirety.

FIELD

Provided herein are fluorescent sensor agents, and methods of use and manufacture thereof. In particular, sensor agents are provided that exhibit a detectable change in fluorescence (e.g., fluorescence intensity) upon alteration of the pH of the surrounding environment (e.g., upon moving from one pH environment to another).

BACKGROUND

Changes in pH regulate many biological and cellular processes. Differences in pH exist between the intracellular and extracellular environments as well as between various cellular compartments.

SUMMARY

In some embodiments, the present invention provides pH sensor agents comprising a rhodamine-class core structure and one or more (e.g., 2, 3, 4, 5, 6, or more) substituted piperazine groups. In some embodiments, pH sensor agents comprise two substituted piperazine groups. In some embodiments, the substituted piperazine groups are attached to amino groups on the rhodamine-class core structure. In some embodiments, the substituted piperazine groups are attached to the rhodamine-class core structure at a first nitrogen of the substituted piperazine. In some embodiments, the substituted piperazine groups comprise a substituent group attached to a second nitrogen of the substituted piperazine. In some embodiments, the substituent comprises an alkyl group. In some embodiments, the alkyl group comprises a heteroalkyl group. In some embodiments, the substituent comprises any combination of alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. In some embodiments, the pH sensor agent is fluorescent at acidic pH (e.g., pH 1-6, pH 1, pH 2, pH 3, pH 4, pH 5). In some embodiments, the pH sensor agent is maximally fluorescent at an acidic pH. In some embodiments, the pH sensor agent exhibits less than 10% of maximum fluorescence at a neutral pH (e.g., about 9%, about 8%, about 7%, about 6%, about 5%, about 4%, about 3%, about 2%, about 1%, about 0.5%, about 0.1%). In some embodiments, the pH sensor agent is non-fluorescent at a neutral pH (e.g., pH 6-8). In some embodiments, the pH sensor agent undergoes photoioninduced electron transfer quenching at neutral or basic pH. In some embodiments, the rhodamine-class core structure comprises rhodamine B, rhodamine 6G, rhodamine 123, carboxytetramethylrhodamine, tetramethylrhodamine, an isothiocyanate derivative of tetramethylrhodamine, sulforhodamine 101, Texas Red, Rhodamine Red, or NHS-rhodamine. In some embodiments, the substituted piperazine groups comprise a piperazine ring and a substituent group, wherein the substituent group is selected from an alkyl chain or a substituted alkyl chain. In some embodiments, the substituted alkyl chain is selected from $CH_2(CH_2)_nSO_3^-$ and $CH_2(CH_2)_nCO_2H$, wherein n=0-25 (e.g., n=2-6, n=3-4, etc.).

In certain embodiments, a pH sensor comprises the general structure of (Formula I):

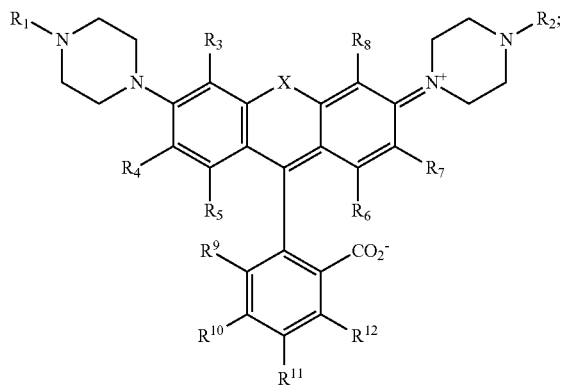

wherein $R_1$-$R_{12}$ are independently: H, F, Cl, Br, I, OH, an alkoxide group, an alkyl group, a heteroalkyl group, an aryl group, $CO_2H$, $SO_3H$, L-$CO_2H$, L-$SO_3H$, L-W, or L-CS; wherein L is a linear, branched, and/or cyclic covalent linkage comprising 0-16 non-hydrogen atoms (e.g., L=1=) and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, F, Cl, Br, I, OH, an alkoxide group, an alkyl group, an aryl group, $CO_2H$, $SO_3H$, L-$CO_2H$, L-$SO_3H$, L-Y, or L-CS; and wherein M is selected from C, N, O, Si, P, S, Ge, As, Se, Sn, Sb, Te, Pb, Bi, and Po.

In certain embodiments, a pH sensor comprises the general structure of (Formula II):

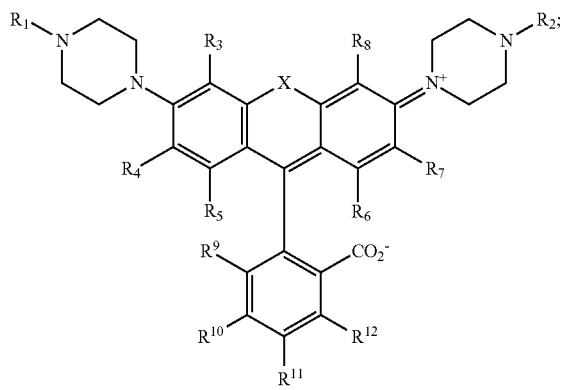

wherein $R_1$ and $R_2$ are independently: H, an alkyl group, an aryl group, L, L-W, or L-CS; wherein $R_3$-$R_8$ are independently: H, F, Cl, an alkoxide group, an alkyl group, an aryl group; and wherein $R_9$-$R_{12}$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS.

In particular embodiments, a pH sensor comprises the general structure of (Formula III):

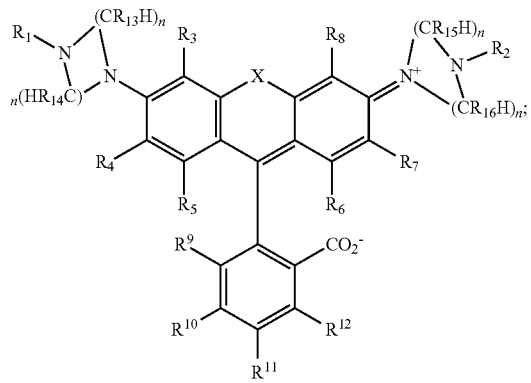

wherein $R_1$ and $R_2$ are independently: H, an alkyl group, an aryl group, L, L-W, or L-CS; wherein $R_3$-$R_8$ are independently: H, F, Cl, an alkoxide group, an alkyl group, an aryl group; wherein $R_9$-$R_{12}$ are independently: H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, an alkyl group, an alkyl group, an aryl group, L, L-R, L-W, or L-CS; wherein M is selected from C, N, O, Si, P, S, Ge, As, Se, Sn, Sb, Te, Pb, Bi, and Po; wherein each n is independently 2-4, wherein each individual $R_{13}$, $R_{14}$, $R_{15}$, and $R_{16}$ are independently: H, F, Cl, Br, I, OH, an alkoxide group, an alkyl group, an aryl group, $CO_2H$, $SO_3H$, L-$CO_2H$, L-$SO_3H$, L-R, L-W, or L-CS. In some embodiments, one or more cyclic structures are formed by bonds between groups selected from: an $R_{13}$ or the associated C and $R_3$ or the associated C, an $R_{14}$ or the associated C and $R_4$ or the associated C, an $R_{15}$ or the associated C and $R_8$ or the associated C, and an $R_{16}$ or the associated C and $R_7$ or the associated C.

In other embodiments, pH sensor agents comprise the general structure of (Formula IV):

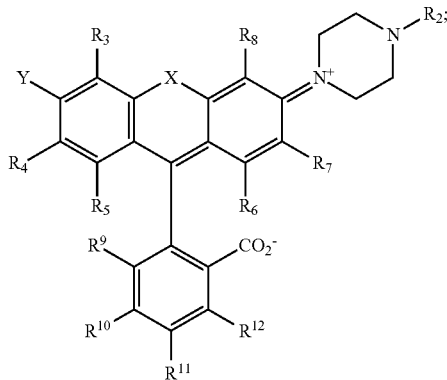

wherein $R_2$ is: H, an alkyl group, an aryl group, L, L-W, or L-CS; wherein $R_3$-$R_8$ are independently: H, F, Cl, an alkoxide group, an alkyl group, an aryl group; wherein $R_9$-$R_{12}$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, an alkyl group, an alkyl group, an aryl group, L, L-R, L-W, or L-CS; wherein M is selected from C, N, O, Si, P, S, Ge, As, Se, Sn, Sb, Te, Pb, Bi, and Po; and wherein Y is any N—$R_{18}$, wherein $R_{18}$ is any alkyl group or aryl group cyclized independently or as part of a cyclic structure with $R_3$ or $R_4$.

In some embodiments, pH sensor agents comprise the general structure of (Formula V):

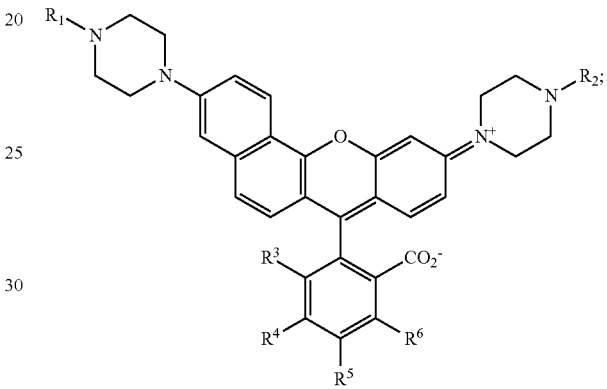

wherein $R_1$ and $R_2$ are independently: H, an alkyl group, an aryl group, L, L-W, or L-CS; wherein $R_3$-$R_6$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; and wherein W is a reactive group.

In certain embodiments, pH sensor agents comprise the general structure of (Formula VI):

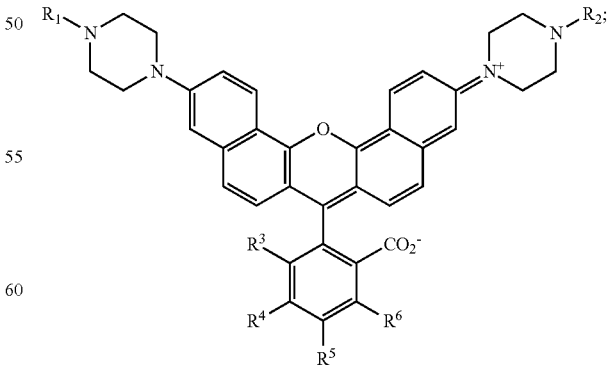

wherein $R_1$ and $R_2$ are independently: H, an alkyl group, an aryl group, L, L-W, or L-CS; wherein $R_3$-$R_6$ are independently H, F, Cl, Br, I, OH, an alkoxide group, an alkyl group, an aryl group, CO$_2$H, SO$_3$H, L-CO$_2$H, L-SO$_3$H, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thio-ether, halide, single bonds, double bonds, triple bonds, and aromatic bonds; and wherein W is a reactive group.

In some embodiments, the present invention provides a pH sensor agent comprising a structure of:

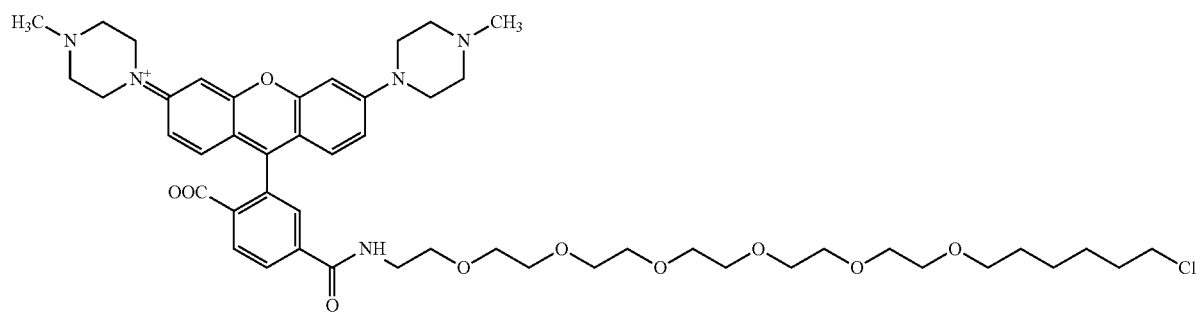

In some embodiments, the present invention provides a pH sensor agent comprising a structure of:

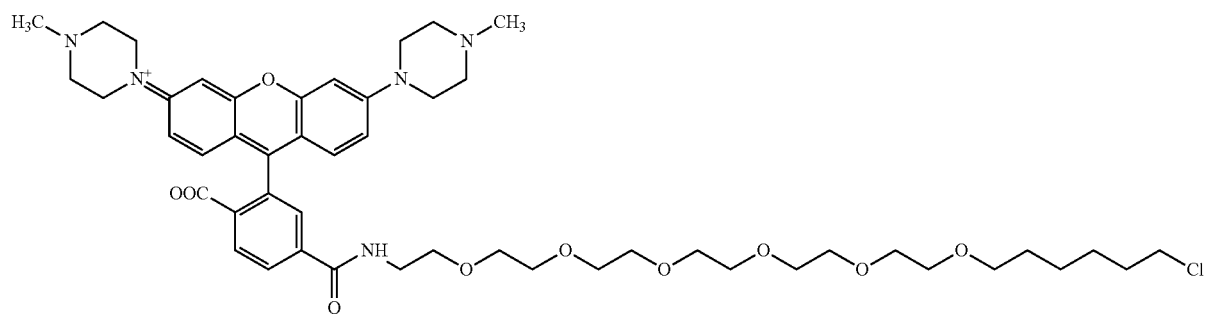

In some embodiments, the present invention provides compositions comprising an entity of interest tethered (e.g., directly, indirectly, covalently, non-covalently, etc.) to a pH sensor agent. In some embodiments, the entity of interest is selected from: a protein, peptide, polysaccharide, lipid, macromolecular complex, polynucleotides, nucleic acids, or small molecule. In some embodiments, the entity of interest is a protein, wherein the protein is a cell surface receptor, antibody or enzyme. In some embodiments, the entity of interest is a polysaccharide, wherein the polysaccharide is dextran. In some embodiments, the entity of interest and the pH sensor agent are tethered by a linker moiety.

In certain embodiments herein, methods of detecting the pH of an environment comprising: (a) contacting the environment with a pH sensor agent; (b) detecting fluorescence (or lack thereof) from the pH sensor agent; and (c) correlating the fluorescence to the pH in the environment are provided. In some embodiments, correlating the fluorescence comprises comparing the fluorescence intensity to reference value(s) (e.g., standard value, control value, maximum fluorescence under experimental conditions, maximum fluorescence under control conditions, etc.).

Particular embodiments of the present invention provide methods of monitoring changes in the pH of an environment comprising: (a) contacting the environment with a pH sensor agent; (b) detecting fluorescence (or lack thereof) from the pH sensor agent over time; and (c) correlating changes in fluorescence to changes in pH in the environment. In some embodiments, fluorescence changes may comprise increase in fluorescence, decrease in fluorescence, or both (e.g., an increase in fluorescence followed by a decrease, a decrease in fluorescence followed by an increase, etc.). In some embodiments, detecting fluorescence from the pH sensor agent over time comprises real-time detection of fluorescence. In some embodiments, detecting fluorescence from the pH sensor agent over time comprises detecting fluorescence at various time points.

Certain embodiments of the present invention provide methods of detecting movement of an entity of interest from a first pH environment to a second pH environment comprising: (a) contacting the first pH environment with a pH sensor agent; (b) detecting fluorescence (or lack thereof) of the pH sensor agent in the first pH environment; (c) monitoring the fluorescence of the pH sensor agent, wherein a change (e.g., increase or decrease) in the fluorescence indicates movement of the pH sensor agent to a second pH environment. In some embodiments, the first pH environment is extracellular, and the second pH environment is intracellular. In some embodiments, fluorescence is monitored in real-time. In some embodiments, the pH sensor agent is detected a various time points. In some embodiments, the pH sensor agent is tethered to an entity of interest. In some embodiments, the entity of interest is selected from: a protein, peptide, polysaccharide, lipid, polynucleotides, nucleic acids, or small molecule. In some embodiments, the entity of interest is a protein, wherein the protein is a cell surface receptor, antibody or enzyme.

In some embodiments, the present invention provides a composition comprising an entity of interest (e.g., molecule, protein, peptide, particle, complex, macromolecule, compound, nucleic acid, polynucleotide etc.) tethered to a pH sensor agent comprising a rhodamine-class core structure and one or more (e.g., two) substituted piperazine groups. In some embodiments, the entity of interest is selected from: a particle (e.g., nanoparticle, bead, viral particle, etc.), protein, peptide, polysaccharide, lipid, macromolecular complex, polynucleotide, nucleic acids, or small molecule. In some embodiments, the entity of interest is a protein or peptide. In some embodiments, the protein is a cell surface receptor, antibody or enzyme. In some embodiments, the entity of interest is a polysaccharide, wherein the polysaccharide is dextran. In some embodiments, the entity of interest (e.g., molecule, particle, complex, macromolecule, compound, etc.) and the pH sensor agent are tethered by a linker moiety. In some embodiments, an entity of interest is a lanthanide-complexing group; a nickel-complexing group; a cobalt-complexing group; ethylenediamine tetraacetic acid; nitrilo-acetic acid; a nucleotide; a substrate of an enzyme; an inhibitor of an enzyme, preferably an irreversible inhibitor of an enzyme forming a covalent bond with an enzyme; an agonist of a receptor; a ligand that binds with a KD of at least 10 µM to a nucleic acid; a ligand that binds with a KD of at least 10 µM to a protein; a substrate of SNAP-tag; a substrate of CLIP-tag; a substrate of Halo-tag, a ligand binding to dihydrofolate reductase; methotrexate; trimethoprim; a substrate of biotin ligase; a substrate of phosphopantetheine transferase; a substrate of lipoic acid ligase; biotin; a ligand binding to streptavidin, avidin or neutravidin; a cofactor of an enzyme; a hormone; a toxin; a fluorophore; a nucleic acid polymer; a hapten; an antigen; a drug; a lipid; a lipid assembly; a non-biological organic polymer; a polymeric microparticle; an animal cell a plant cell; a bacterium, a yeast; a virus; or a protist.

In some embodiments, the present invention provides methods of detecting the pH of an environment comprising: (a) contacting a pH sensor agent comprising a rhodamine-class core structure and one or more (e.g., two) substituted piperazine groups with the environment; (b) detecting fluorescence (or lack thereof) from the pH sensor agent; and (c) correlating the fluorescence to the pH. In some embodiments, correlating the fluorescence comprises comparing the fluorescence intensity to control values (e.g., from a positive or negative control, from the sensor at a difference time point or in a different environment, etc.).

In some embodiments, the present invention provides methods of monitoring changes in the pH of an environment comprising: (a) contacting a pH sensor agent comprising a rhodamine-class core structure and one or more (e.g., two) substituted piperazine groups to the environment; (b) detecting fluorescence from the pH sensor agent over time; and (c) correlating changes in fluorescence to changes in pH. In some embodiments, detecting fluorescence from the pH sensor agent over time comprises real time detection of fluorescence. In some embodiments, detecting fluorescence from the pH sensor agent over time comprises detecting fluorescence at various time points (e.g., start point, end point, times therein).

In some embodiments, the present invention provides methods of detecting movement of an entity of interest (e.g., molecule, particle, complex, macromolecule, compound, nucleic acid, polynucleotide, etc.) from a first pH environment to a second pH environment comprising: (a) contacting a pH sensor agent comprising a rhodamine-class core structure and one or more (e.g., two) substituted piperazine groups with the first pH environment; (b) detecting fluorescence of the pH sensor agent in the first pH environment; (c) monitoring the fluorescence of the pH sensor agent, wherein a change in the fluorescence indicates movement of the pH sensor agent to a second pH environment. In some embodiments, the first pH environment is extracellular, and the second pH environment is intracellular. In some embodiments, the first pH environment is a cellular compartment and/or organelle, and the second pH environment is cytoplasm or a second cellular compartment and/or organelle. In some embodiments, the first pH environment is basic or neutral, and the second pH environment is acidic. In some embodiments, the first pH environment is acidic, and the second pH environment is basic or neutral. In some embodiments, fluorescence is monitored in real-time. In some embodiments, fluorescence is detected at various time points. In some embodiments, the change in fluorescence is an increase of fluorescence. In some embodiments, the change in fluorescence is a decrease of fluorescence. In some embodiments, the pH sensor agent is tethered to an entity of interest (e.g., molecule, particle, complex, macromolecule, compound, nucleic acid, polynucleotide, etc.). In some embodiments, the entity of interest is selected from: a protein, peptide, polysaccharide, lipid, nucleic acid, polynucleotide or small molecule. In some embodiments, the entity of interest is a protein, and wherein the protein is a cell surface receptor, antibody or enzyme.

In particular embodiments, the present invention provides kits comprising a pH sensor agent, or a composition comprising a pH sensor agent, in a container. In some embodiments, the present invention provides kits comprising a pH sensor agent tethered to a second entity in a container. In certain embodiments, a second entity is selected from: a peptide, a protein, a polysaccharide, a lipid, a small molecule, a molecule, a nucleic acid, an oligonucleotide, a polynucleotide, a particle (e.g. viral particle, nanoparticle, etc.), a complex, a macromolecule, a compound, etc. In some embodiments, kits further comprise additional components, reagents, controls, substrates, and/or materials.

DESCRIPTION OF THE DRAWINGS

FIG. 1 shows molecular structures of pH sensor compounds (a) PBI-4453 (b) PBI-4479, (c) PBI-4959, (d) PBI-5004, and (e) PBI-5183.

FIG. 2 shows fluorescence emission spectra for (a) compound PBI-4453 and (b) compound PBI-4479.

FIG. 44 shows FACS negative control in U2-OS Cells.

FIG. 45 shows FACS analysis using pH Sensor PBI-4479 in U2-OS HaloTag-ECS cells.

DEFINITIONS

Figure 3:
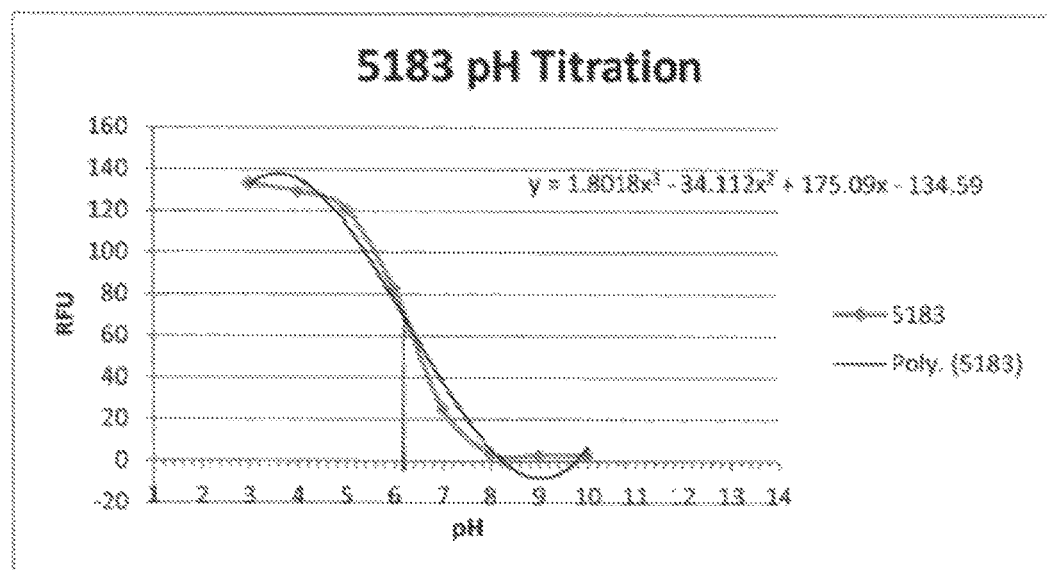
FIG. 3 shows graphs demonstrating the pH dependence of the fluorescence emission of compounds (a) PBI-4453 (b) PBI-4479, (c) PBI-4959, (d) PBI-5004, and (e) PBI-5183.
Figure 4:
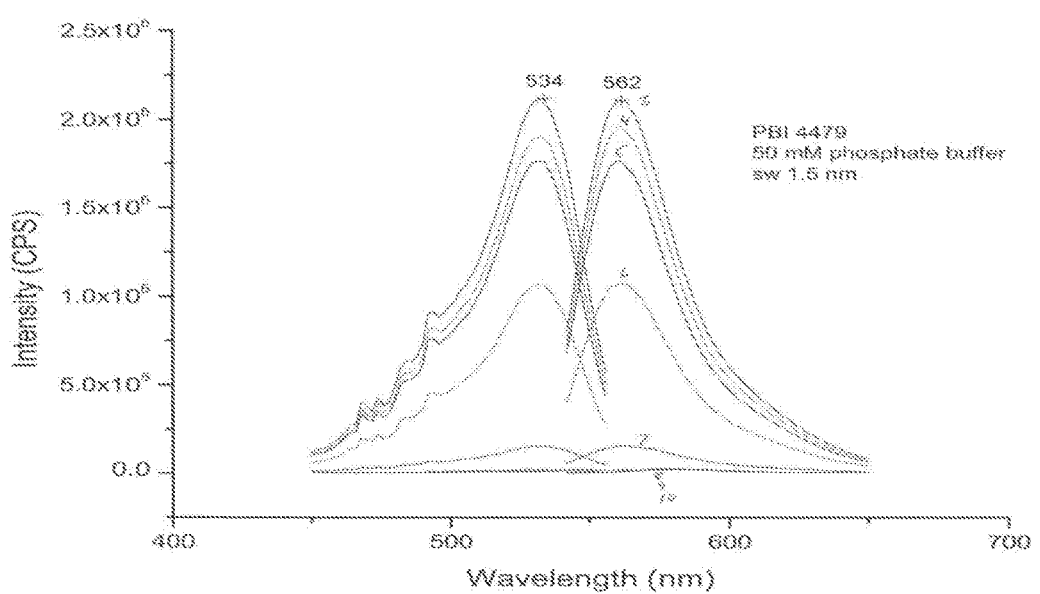
FIG. 4 shows a graph demonstrating the emission and excitation fluorescence intensity profiles of PBI-4479.
Figure 5:
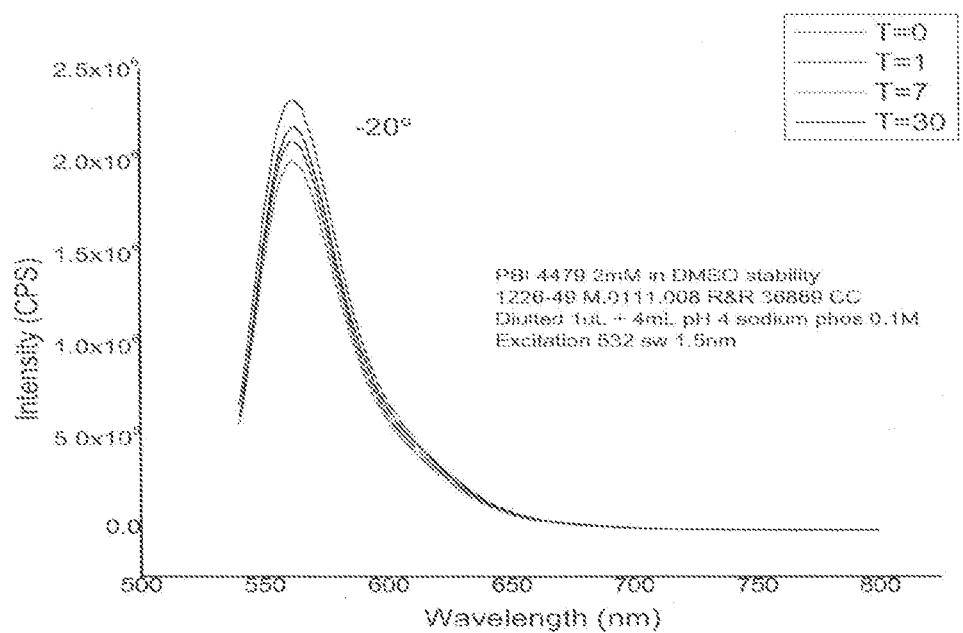
FIG. 5 shows a graph demonstrating the stability profile of PBI-4479 at −20° C.
Figure 6:
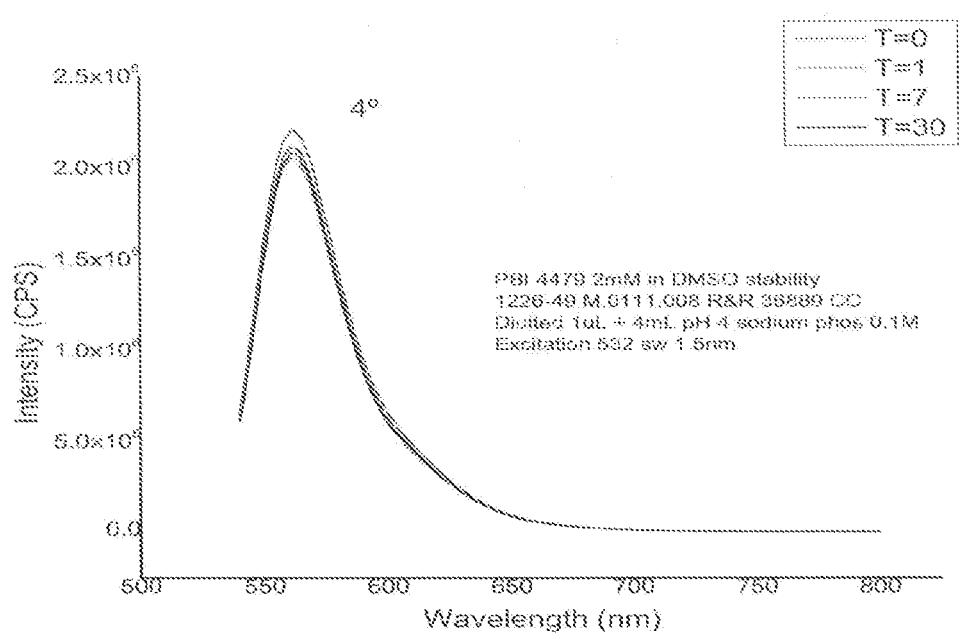
FIG. 6 shows a graph demonstrating the stability profile of PBI-4479 at 4° C.
Figure 7:
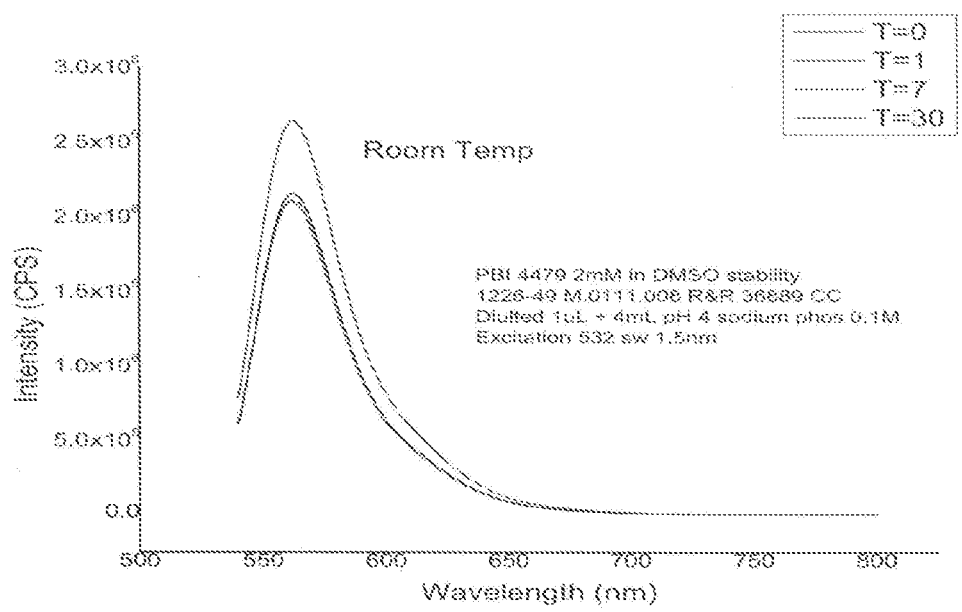
FIG. 7 shows a graph demonstrating the stability profile of PBI-4479 at room temperature.
Figure 8:
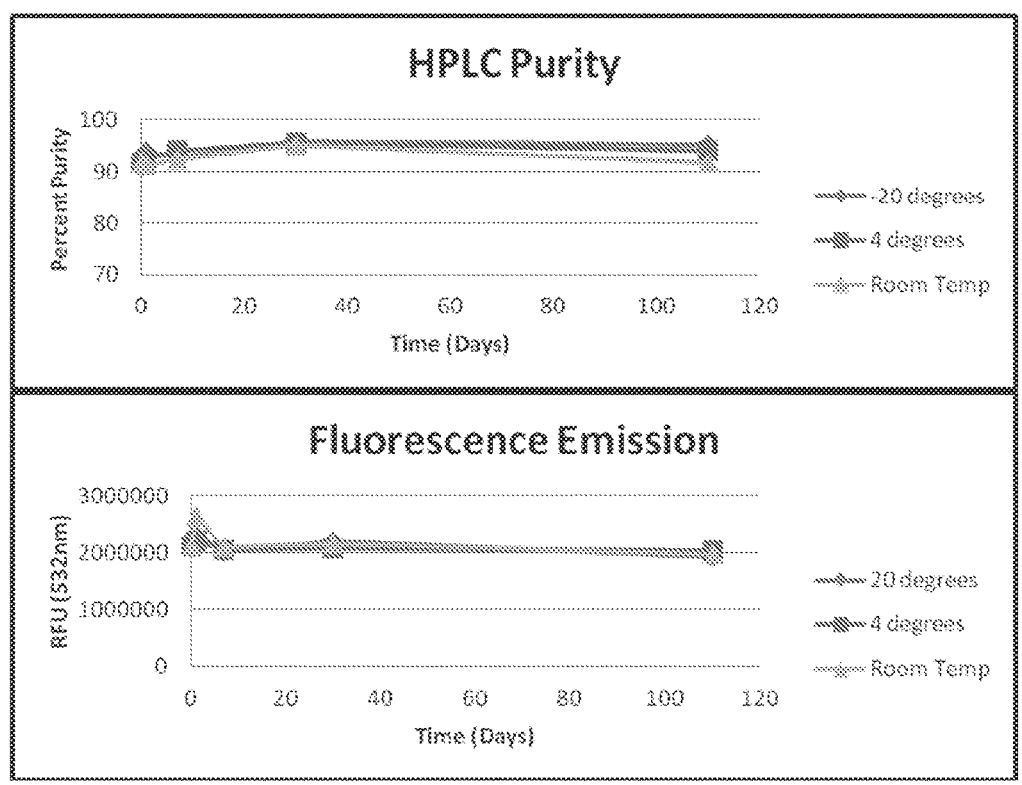
FIG. 8 shows the fluorescent emission intensity and purity (via HPLC) of the pH sensor PBI-4479.

As used herein, the term "maximum fluorescence" refers to the peak fluorescence intensity for any particular fluorescent agent (e.g., in a particular assay, under particular conditions, in a particular environment, etc.).

As used herein, the term "environment" refers to any physical space with specific chemical and physical characteristics that can affect agents or entities residing with the space. Exemplary environments include, but are not limited to: in vitro environments, in vivo environments (e.g., in whole animals), intracellular environment, endosomal environment, extracellular environment, intramembrane environment, etc.

As used herein, the term "entity" refers to any separately distinguishable or definable molecular unit. An entity may be of natural or synthetic creation, and may be as small as molecular hydrogen ($H_2$), or as large as a protein, ribonucleoprotein complex, synthetic particle, polynucleotide, nucleic acid, or viral particle.

As used herein, the term "reactive group" refers to a chemical moiety capable of reacting with a partner chemical moiety to for a covalent linkage. A moiety may be considered a reactive group based on its high reactivity with a single partner-moiety, a set of partner-moieties, or based on its reactivity with many partners.

As used herein, the term "alkyl" refers to saturated aliphatic groups including straight-chain, branched-chain and cyclic groups having the number of carbon atoms specified, or if no number is specified, having up to 20 carbon atoms. The term "$C_4$-$C_6$ alkyl" as used herein refers to a straight or branched chain of carbon atoms of four to six carbons. The term "cycloalkyl" as used herein refers to a mono-, bi-, or tricyclic aliphatic ring having 3 to 20 carbon atoms, unless the number of carbons is specified (e.g., $C_6$ cycloalkyl, cyclohexane, etc.). A "heteroalkyl" refers to an alkyl group substituted with one, two, three, or more substituents including but not limited to alkoxy, amino, imino, imide, alkyl, alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted.

As used herein, the term "aryl" refers to an unsubstituted or substituted aromatic ring (e.g., a 5-6 membered ring containing 0-4 heteroatoms independently selected from N, O and S). A "heteroaryl" refers to an aryl group substituted with one, two, three, or more substituents including but not limited to alkoxy, amino, imino, imide, alkyl, alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, pyridyll, pyrimidyl, pyrazinyl, triazyl, furyl, thienyl, pyrrolyl, thiazolyl, oxazolyl, imidazolyl, isoxazolyl, pyrazolyl, 1,2,3-triazolyl, 1,2,4-triazolyl, thiadiazolyl and tetrazoly halophenyl, loweralkylphenyl, naphthyl, biphenyl, phenanthrenyl and naphthacenyl. Attachment points to the aryl groups are defined as any carbon or nitrogen atom in the ring system that contains a hydrogen atom when the aryl group is not attached. Up to 3 aryl ring hydrogens residing on carbon or nitrogen atoms may be independently substituted with groups selected from those described above with reference to the heterocycloalkyl groups.

As used herein, the terms "halo" or "halogen" refer to Cl, Br, F and/or I substituents. The term "haloalkyl", and the like, refer to an aliphatic carbon radicals having at least one hydrogen atom replaced by a Cl, Br, F or I atom, including mixtures of different halo atoms.

The term "alkoxide", as used herein, refers to the oxy anion of an alcohol having from 1 to 20 carbons, arranged linearly or branched. Exemplary alkoxides include methoxide, ethoxide, propoxide, isopropoxide, butoxide, and t-butoxide.

DETAILED DESCRIPTION

Provided herein are fluorescent sensor agents (e.g., molecules), and methods of use and manufacture thereof. In particular, sensor agents are provided that exhibit a detectable change in fluorescence (e.g., intensity) upon alteration of the pH of the surrounding environment (e.g., upon moving from one cellular environment to another).

In some embodiments, fluorescent sensors are provided that exhibit a detectable change (e.g., an increase or decrease) in fluorescence characteristics (e.g., emission, excitation, wavelength, magnitude, intensity, etc.) upon alteration of the pH of the environment (e.g., proximate environment) within which the sensor resides (e.g., extracellular, intracellular, cytoplasmic, nuclear, endosomal, etc.). In some embodiments, a detectable change in signal (e.g., on/off of fluorescent emission, reduction in fluorescence intensity) is detectable upon a change in pH (e.g., neutral to acidic, neutral to basic, acidic to basic, basic to acidic, weakly basic to highly basic, weakly acidic to highly acidic, etc.). In some embodiments, sensor agents are fluorescent in a first pH environment (e.g., acidic). In some embodiments, sensor agents are non-fluorescent in a second pH environment (e.g., neutral, basic). In other embodiments, sensor agents exhibit a low level fluorescence in a second pH environment (e.g., neutral, basic) when compared to a first pH environment. In some embodiments, sensor agents are configured for attaching and/or tethering (e.g., covalently, non-covalently, directly, indirectly (e.g., via a linker or other group, moiety, or molecule)) to a protein (e.g. enzyme, receptor, etc.), molecule of interest, complex, antibody, polysaccharide (e.g., dextran, etc.), viral particle, nucleic acid, polynucleotide, lipid, small molecule, etc.

In some embodiments, the present invention provides piperazino rhodamine molecules that exhibit photoinduced electron transfer (PET) quenching when the R-substituted nitrogen is unprotontated or becomes deprotonated. In some embodiments, such piperazino rhodamine molecules provide fluorogenic pH sensors that are dark (e.g., non-fluorescent, exhibit a low level fluorescence (e.g., <10%, <5%, <4%, <3%, <2%, <1%) of maximal fluorescence in otherwise similar conditions)) at basic to neutral pH and fluorescent (e.g., >50% of maximal fluorescence, >75% of maximal fluorescence, >90% of maximal fluorescence, >95% of maximal fluorescence, >99% of maximal fluorescence) at acidic pH. Structurally similar rosamine structures are not water soluble, become involved in unfavorable/undesirable cellular interactions, and/or tend to compartmentalize (e.g., within cellular organelles and/or compartments). In some embodiments, the piperazino rhodamine molecules described herein provide useful fluorescent sensor agents (e.g., pH sensor agents).

In some embodiments, sensor agents comprise a rhodamine core structure (e.g., rhodamine class core structure, rhodamine-like core structure, etc.). In some embodiments, a rhodamine core structure comprises a rhodamine class compound. Sensor agents provided herein are not limited by the structure of the rhodamine core structure. Any rhodamine class compound, rhodamine-related structure, or rhodamine-derivative finds use as a core structure, for example: rhodamine B, rhodamine 6G, rhodamine 123, carboxytetramethylrhodamine (TAMRA), tetramethylrhodamine (TMR), the isothiocyanate derivative of TMR (TRITC) sulforhodamine 101, Texas Red, Rhodamine Red, NHS-rhodamine, and derivatives thereof.

In some embodiments, sensor agents comprise one or more piperazine groups, piperazine class compounds, substituted piperazine groups, or piperazine derivatives attached to a rhodamine class core. In some embodiments, suitable piperazine class compounds include, but are not limited to: phenylpiperazines, benzylpiperazines, diphenylmethylpiperazines (benzhydrylpiperazines), pyridinylpiperazines, pyrimidinylpiperazines, 1,4,-substituted piperazines, and tricyclics. In some embodiments, piperazine groups comprise any suitable substituents and/or functional groups. In some embodiments, one or more substituents and/or functional groups are located at any position of a piperazine class compound. In some embodiments, piperazine groups are attached to the amino groups of a rhodamine-class core structure. In some embodiments, one piperazine group is attached to each amino group of a rhodamine class core. In some embodiments, substituted piperazine groups are attached to amino groups on said rhodamine-class core structure. In some embodiments, a sensor agent comprises two piperazine groups (e.g., substituted piperazine groups). In some embodiments, one of the ring nitrogens of a piperazine group is attached to the rhodamine core (e.g., at the amino group). In some embodiments, a piperazine group comprises a substituent group and/or functional group attached to one of the ring nitrogens of a piperazine group.

In some embodiments, sensor agents comprise the general structure of Formula I:

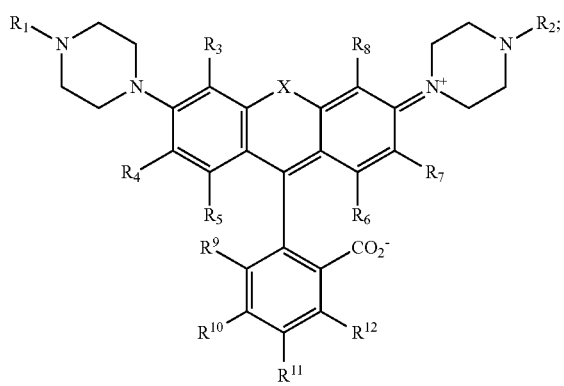

wherein $R_1$-$R_{12}$ are independently: H, F, Cl, Br, I, OH, an alkoxide group, an alkyl group, an aryl group, $CO_2H$, $SO_3H$, L-$CO_2H$, L-$SO_3H$, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, F, Cl, Br, I, OH, an alkoxide group, an alkyl group, an aryl group, $CO_2H$, $SO_3H$, L-$CO_2H$, L-$SO_3H$, L-Y, or L-CS; and wherein M is selected from C, N, O, Si, P, S, Ge, As, Se, Sn, Sb, Te, Pb, Bi, and Po.

In some embodiments, sensor agents comprise the general structure of Formula II:

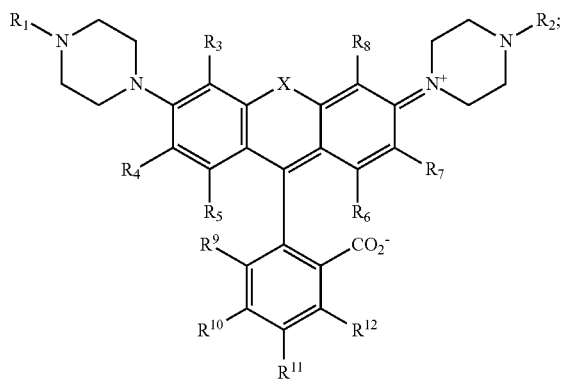

wherein $R_1$ and $R_2$ are independently: H, an alkyl group, an aryl group, L, L-W, or S-L-W; wherein $R_3$-$R_8$ are independently: H, F, Cl, an alkoxide group, an alkyl group, an aryl group; wherein $R_9$-$R_{12}$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group selected from, for example: SE, iodoacetamide, maleimide, acid halides, isocyanates, sulfonyl halides, etc.; wherein X is: O, $CR_{13}$, $MR_{17}$; wherein $R_{17}$ is: H, an alkyl group, an alkyl group, an aryl group, L, L-W, L-R, or L-CS; and wherein M is selected from C, N, O, Si, P, S, Ge, As, Se, Sn, Sb, Te, Pb, Bi, and Po.

In some embodiments, sensor agents comprise the general structure of Formula III:

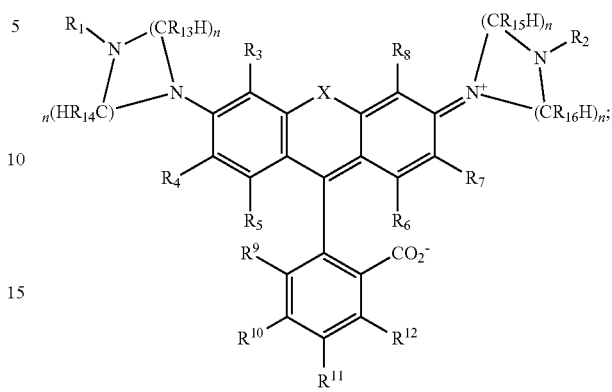

wherein $R_1$ and $R_2$ are independently: H, an alkyl group, an aryl group, L, L-W, or L-CS; wherein $R_3$-$R_8$ are independently: H, F, Cl, an alkoxide group, an alkyl group, an aryl group; wherein $R_9$-$R_{12}$ are independently: H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, an alkyl group, an alkyl group, an aryl group, L, L-R, L-W, or L-CS; wherein M is selected from C, N, O, Si, P, S, Ge, As, Se, Sn, Sb, Te, Pb, Bi, and Po; wherein each n is independently 2-4, wherein each individual $R_{13}$, $R_{14}$, $R_{15}$, and $R_{16}$ are independently: H, F, Cl, Br, I, OH, an alkoxide group, an alkyl group, an aryl group, $CO_2H$, $SO_3H$, L-$CO_2H$, L-$SO_3H$, L-R, L-W, or L-CS. In some embodiments, an $R_{13}$ or the associate C forms a cyclic structure with $R_3$ or the associated C, an $R_{14}$ or the associate C forms a cyclic structure with $R_4$ or the associated C, an $R_{15}$ or the associate C forms a cyclic structure with $R_g$ or the associated C, and/or an $R_{16}$ or the associate C forms a cyclic structure with $R_7$ or the associated C.

In some embodiments, sensor agents comprise the general structure of Formula IV:

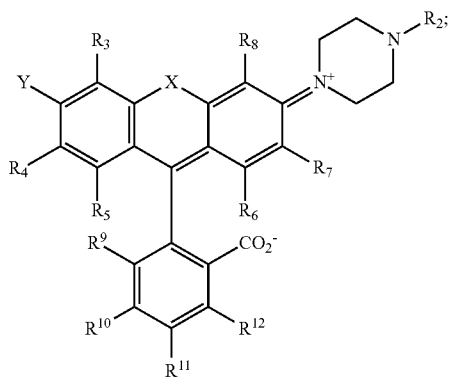

wherein $R_2$ is: H, an alkyl group, an aryl group, L, L-W, or L-CS; wherein $R_3$-$R_8$ are independently: H, F, Cl, an alkoxide group, an alkyl group, an aryl group; wherein $R_9$-$R_{12}$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, an alkyl group, an alkyl group, an aryl group, L, L-R, L-W, or L-CS; wherein M is selected from C, N, O, Si, P, S, Ge, As, Se, Sn, Sb, Te, Pb, Bi, and Po; and wherein Y is any N—$R_{18}$, wherein $R_{18}$ is any alkyl group or aryl group cyclized independently or as part of a cyclic structure with $R_3$ or $R_4$.

In some embodiments, sensor agents comprise the general structure of Formula V:

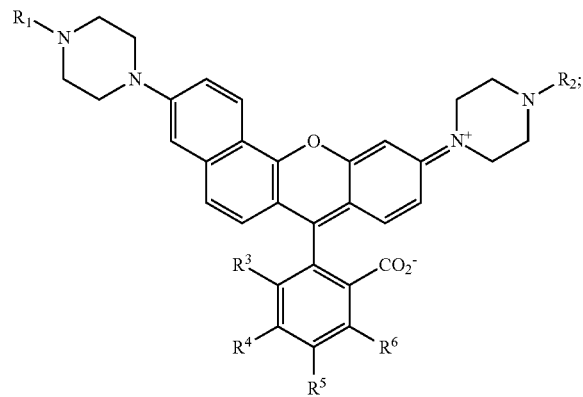

wherein $R_1$ and $R_2$ are independently: H, an alkyl group, an aryl group, L, L-W, or L-CS; wherein $R_3$-$R_6$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; and wherein W is a reactive group.

In some embodiments, sensor agents comprise the general structure of Formula VI:

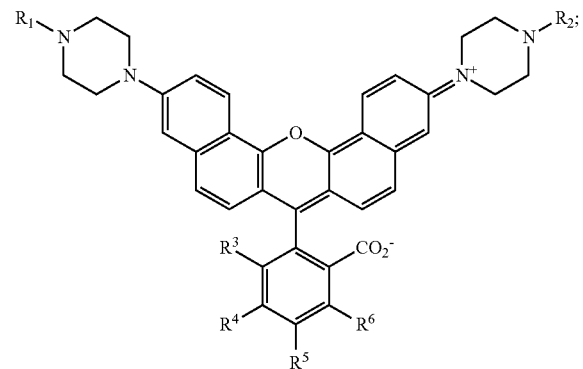

wherein $R_1$ and $R_2$ are independently: H, an alkyl group, an aryl group, L, L-W, or L-CS; wherein $R_3$-$R_6$ are independently H, F, Cl, Br, I, OH, an alkoxide group, an alkyl group, an aryl group, $CO_2H$, $SO_3H$, L-$CO_2H$, L-$SO_3H$, L-R, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; and wherein W is a reactive group.

In certain embodiments, the R groups ($R^1$-$R^{18}$) of the above structures (Formulas I-VI), each independently comprise any combination of hydrogen, alkyl, alkenyl, alkynyl, phenyl, benzyl, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. In some embodiments, one or more R groups ($R^1$-$R^{18}$) comprise substituted alkyl moieties. In some embodiments, a substituted alkyl moiety comprises and alkyl chain displaying one or more functional groups (e.g., O, N, S, or P containing functional groups) at one or more positions along its length.

In preferred embodiments, sensor agents comprise rhodamine class core and one or more R-substituted piperazino groups. The core may comprise, consist of, or essentially consist of a rhodamine class compound. In certain embodiments, R-substituted piperazino groups are bound (e.g., directly or through a suitable linker group) to one or more of the amino groups on the rhodamine class core.

In some embodiments, sensor agents comprise the structure of one of Formulas VII-XII:

Formula VII

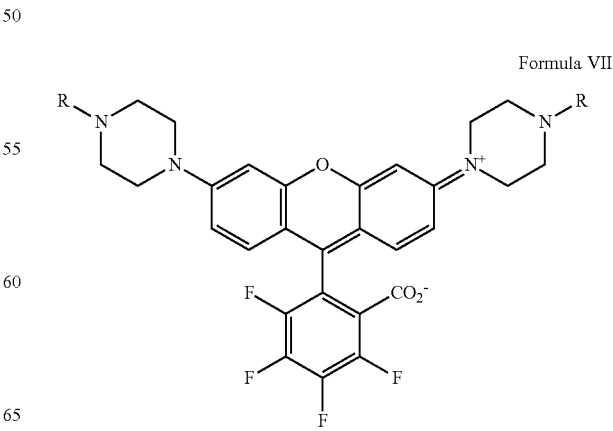

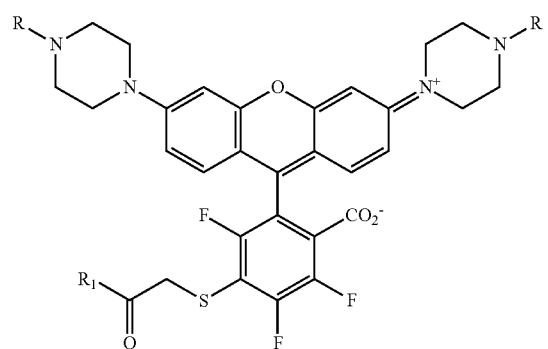

Formula VIII

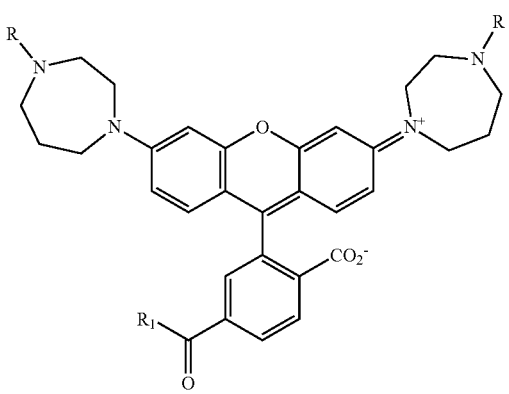

Formula XI

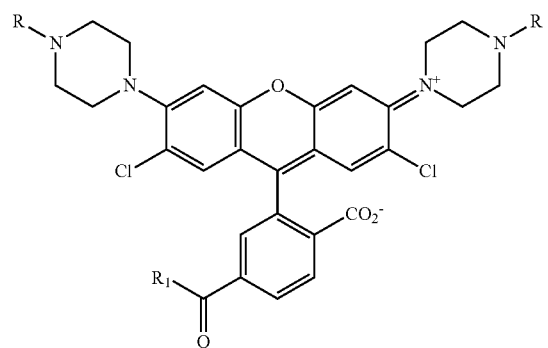

Formula IX

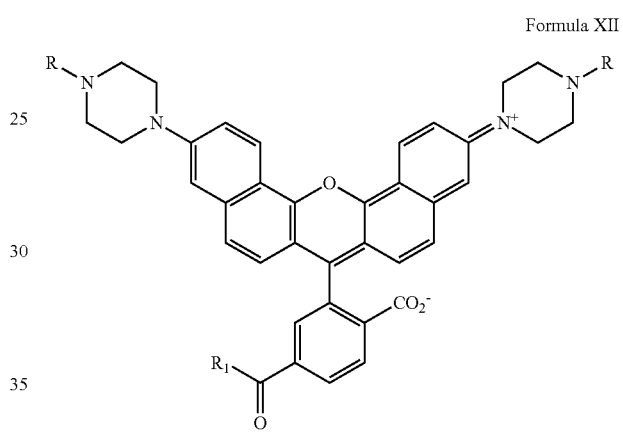

Formula XII

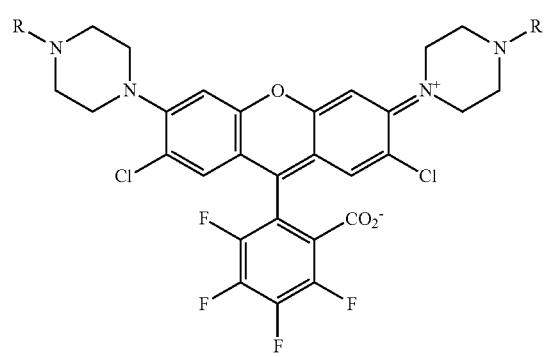

Formula X wherein each R independently comprises an alkyl group (e.g. linear, branched, cyclic, or combinations thereof) of 1-20 carbons, a substituted alkyl group (e.g., $CH_2COCH_2COOH$), or a terminally substituted alkyl group (e.g., $(CH_2)_4SO_3^-$); and wherein $R_1$ comprises, an alkyl group, aryl group, substituted alkyl or aryl group, any suitable functional group (e.g. OH, SH, a ligand, $NH(CH_2O)_u (CH_2)_v$-halogen (wherein u=0-10 and v=0-10), etc.).

In some embodiments, sensor agents comprise the structure of one of Formula XIII:

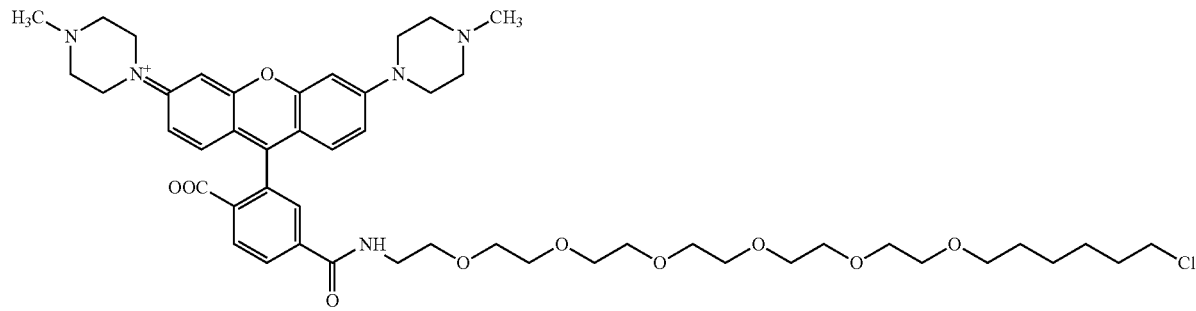

In some embodiments, sensor agents comprise the structure of one of Formula XIV:

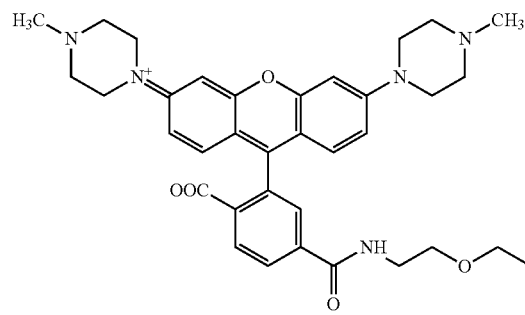

In some embodiments, a sensor agent is non-fluorescent (e.g., exhibits no fluorescence) at a first pH or pH range (e.g., neutral, basic, or acidic). In some embodiments, a sensor agent is non-fluorescent at basic pH (e.g. pH>7, pH>8, pH>9, pH>10, ranges therein, etc.). In some embodiments, a sensor agent is non-fluorescent at neutral pH or at weak acidic or weak basic pH (e.g. pH 7, pH 5.5-7.5, pH 5-8, ranges therein, etc.). In some embodiments, a sensor agent is non-fluorescent at about pH 7.2. In some embodiments, a sensor agent is weakly fluorescent (e.g., <10% of maximum fluorescence, <5% of maximum fluorescence, <1% of maximum fluorescence) at a first pH or pH range (e.g., neutral, basic, or acidic). In some embodiments, a sensor agent is weakly fluorescent (e.g., <10% of maximum fluorescence, <5% of maximum fluorescence, <1% of maximum fluorescence) at basic pH (e.g. pH>7, pH>8, pH>9, pH>10, ranges therein, etc.). In some embodiments, a sensor agent is weakly fluorescent (e.g., <10% of maximum fluorescence, <5% of maximum fluorescence, <1% of maximum fluorescence) at neutral pH or at weak acidic or weak basic pH (e.g. pH 7, pH 5.5-6.5, pH 5-8, ranges therein, etc.). In some embodiments, a sensor agent is weakly fluorescent (e.g., <10% of maximum fluorescence, <5% of maximum fluorescence, <1% of maximum fluorescence) at about pH 7.2. In some embodiments, fluorescence is measured and/or compared using any suitable units (e.g. counts per second (CPS)). In some embodiments, fluorescence is measured and/or reported as relative to a reference measurement (e.g., a reference sample, a control sample, a no fluorophore control, etc.). In some embodiments, fluorescence is measured and/or reported as relative to a maximum or minimum fluorescence signal (e.g., under the conditions being monitored, under standard conditions, under control conditions, etc.).

In some embodiments, a sensor agent fluoresces at a second pH or pH range (e.g., neutral, basic, or acidic). In some embodiments, a sensor agent is fluorescent at acidic pH (e.g. pH<7, pH<6, pH<5, pH<4, pH<3, ranges therein, etc.). In some embodiments, a sensor agent is highly fluorescent (e.g., >50 of maximum fluorescence, >60% of maximum fluorescence, >70% of maximum fluorescence, >80% of maximum fluorescence, >90% of maximum fluorescence, >95% of maximum fluorescence, >99% of maximum fluorescence) at acidic pH (e.g. pH<7, pH<6, pH<5, pH<4, pH<3, ranges therein, etc.). In some embodiments, a sensor agent is maximally fluorescent between pH 1.0 and 5.5 (e.g., pH 1.0, pH 1.1, pH 1.2, pH 1.3, pH 1.4, pH 1.5, pH 1.6, pH 1.7, pH 1.8, pH 1.9, pH 2.0, pH 2.1, pH 2.2, pH 2.3, pH 2.4, pH 2.5, pH 2.6, pH 2.7, pH 2.8, pH 2.9, pH 3.0, pH 3.1, pH 3.2, pH 3.3, pH 3.4, pH 3.5, pH 3.6, pH 3.7, pH 3.8, pH 3.9, pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, and pH 5.5).

In some embodiments, a sensor agent exhibits maximal excitation in the acidic range (e.g., pH 1-5, pH 1-5.5, pH 1-6, pH 1-6.5, pH 1-6.9), and decreasing excitation intensity at increasing pH, reaching zero or almost zero fluorescence (e.g., <1% of maximal fluorescence, <5% of maximal fluorescence) in the neutral range (e.g., pH 5.5-8.5). In some embodiments, the fluorescence of a sensor agent decreases as pH increases (e.g., from acidic pH to neutral or basic pH). In some embodiments, fluorescence intensity in the neutral, weak acidic, or weak basic pH ranges (e.g. pH 6.0, pH 6.5, pH 7.0, pH 7.5, pH 8.0, pH8.5) is less than 10% of fluorescence intensity in the acidic pH range (e.g. pH 3.5, pH 4.0, pH 4.5, pH 5.0, pH 5.5, pH 6.0). In some embodiments, small changes in pH (e.g., pH 0.1, pH 0.2, pH 0.3, pH 0.4, pH 0.5) are detectable as changes in fluorescence intensity.

In some embodiments, a suitable sensor agent provides one or more of the characteristics of: non-fluorescent or low fluorescence at a first pH (e.g., neutral or basic) but brightly fluorescent at a second pH (e.g., acidic); photo-stable; chemically stable; stable in a biological environment; non-reactive in a biological environment; non-toxic to cells; conjugatable; contains a linker or functional group for covalent linkage to another molecule or complex; water soluble; cell membrane permeable; cell membrane impermeable; reversible gain/loss of signal (e.g., infinitely reversible); low background; does not compartmentalize within biological systems; localizes within cells; does not localize within cells, etc.

In some embodiments, sensor agents are stable under aqueous, biological, and/or physiological conditions (or other desired conditions). In some embodiments, sensor agents are stable under physiological conditions (or other desired conditions), exhibiting a half life of at least: 10 minutes . . . 20 minutes . . . 30 minutes . . . 1 hour . . . 2 hours . . . 6 hours . . . 12 hours . . . 24 hours . . . 48 hours . . . 72 hours . . . 96 hours, ranges therein, or more). In some embodiments, sensor agents are stable at a broad range of pHs, for example: pH 0.5 . . . pH 1.0 . . . pH 2.0 . . . pH 3.0 . . . pH 4.0 . . . pH 5.0 . . . pH 6.0 . . . pH 7.0 . . . pH 8.0 . . . pH 9.0 . . . pH 10.0, ranges therein, or more. In some embodiments, sensor agents are stable at a broad range of salt and or buffer concentrations (e.g., 0 nM . . . 10 nM . . . 100 nM . . . 1 μM . . . 10 μM . . . 100 μM . . . 1 mM . . . 10 mM . . . 100 mM . . . 1M . . . 10M, ranges therein, or more).

In some embodiments, fluorescent sensor agents are provided that passively cross cellular membranes (e.g., plasma membrane, nuclear membrane, organellar membrane (e.g., endosomal membrane, mitochondrial membrane, chloroplast membrane, etc.), etc.). In some embodiments, sensor agents exhibit detectable changes in fluorescence upon crossing a membrane from one pH environment (e.g., acidic, basic, neutral, or varying degrees thereof) to another (e.g., acidic, basic, neutral, or varying degrees thereof). In some embodiments, sensor agents are membrane impermeable. In some embodiments, sensor agents are unable to cross (e.g., passively and/or otherwise) one or more types of biological membranes (e.g., plasma membrane, nuclear membrane, endosomal membrane, mitochondrial membrane, chloroplastic membrane, etc.). In some embodiments, sensor agents are unable to cross one or more types of membranes without a carrier. In some embodiments, sensor agents require endocytosis to gain cellular entry.

In some embodiments, fluorescent sensor agents are attached (e.g., covalently or non-covalently) to an entity of interest (e.g., peptide, protein, polysaccharide, lipid, small molecule, molecule, nucleic acid, polynucleotide, particle (e.g. viral particle, nanoparticle, etc.), complex, macromolecule, compound, etc.). In some embodiments, fluorescent sensor agents monitor the movement of an entity of interest (e.g., molecule, particle, complex, macromolecule, compound, nucleic acid, polynucleotide, etc.) from a first environment (e.g., extracellular, neutral pH, etc.) to a second environment (e.g., intracellular, acidic, etc.). In some embodiments, a fluorescent sensor agent is attached to an entity of interest to monitor changes in the pH in the environment surrounding the entity of interest. In some embodiments, attachment of the entity of interest is reversible (e.g., cleavable (e.g., photocleavable, chemically cleavable, enzymatically cleavable))

In some embodiments, a sensor agent is covalently linked, non-covalently coupled, bioconjugated (e.g., dextran), and/or antibody conjugated to another entity. In some embodiments, a sensor agent is covalently linked, non-covalently coupled, bioconjugated (e.g., dextran), and/or antibody conjugated to another entity that is internalized (e.g., endocytosed) by a cell. In some embodiments, a sensor agent is covalently linked to an entity of interest (e.g., molecule, particle, complex, macromolecule, compound, nucleic acid, polynucleotide, etc.). In some embodiments, a sensor agent is covalently linked to a protein (e.g., cell surface receptor) and/or protein complex of interest. In some embodiments, a sensor agent is non-covalently coordinated to an entity of interest. In some embodiments, a sensor agent is non-covalently coordinated linked to a protein (e.g., cell surface receptor) and/or protein complex of interest. In some embodiments, sensors are capable of detecting: cellular internalization (e.g., monitoring the internalization of cellular receptors), changes in extracellular or intracellular pH (e.g., due to normal and/or pathological cell processes), intracellular trafficking (e.g., movement from one cellular region or organelle to another), signal transduction events (e.g., causing a change in local conditions in a intracellular compartment), etc.

In some embodiments, a sensor agent is targeted to the cell surface. In some embodiments, a sensor agent is directly or indirectly tethered to a cell surface protein and/or receptor. In some embodiments, a cell surface protein is provided (e.g., expressed) as a fusion with a protein (e.g., enzyme, hydrolase, dehalogenase) that forms a stable bond (e.g., covalent) with a pH sensor agent. In some embodiments, a sensor agent is tethered (e.g., covalently or non-covalently) to a substrate that forms a stable bond (e.g., covalent) with a protein (e.g., enzyme, hydrolase, dehalogenase) that is part of a fusion with a protein of interest (e.g., cell surface protein, disease marker protein). In some embodiments, sensor agents are targeted to cell surface receptors that are indicative of disease states (e.g., cancer, infection, etc.). In some embodiments, sensor agents find utility in tumor targeting (e.g., in acidic environment around tumor cells).

In some embodiments, a sensor agent comprises one or more sites, substituents, and/or functional groups for attachment to a second entity (e.g., agents, moiety, protein, compound, macromolecule, particle, antibody, polysaccharide, etc.). In some embodiments, attachment sites are located at positions that do not affect the fluorescence and/or pH sensitivity of the sensor agent. In some embodiments, attachment sites provide a reactive group that enables the sensor agent to be tethered (e.g., covalently or non-covalently) to a second entity. In some embodiments, attachment sites present functional groups that utilize known coupling chemistries (e.g., maleimide/thiol, carboxylic acid/thiol, click chemistry, Diels-alder, disulfide exchange, hydrazide coupling, carboxylic acid/amine, biotin/steptavividin, etc.) to tether sensor agents to a second entity. The present invention is not limited by chemistries for coupling sensor agents to a second entity. Any suitable coupling chemistries are within the scope of the invention.

In some embodiments, a sensor agent comprises, or is tethered to, a second entity by a linker moiety. In some embodiments, a linker moiety is part of the sensor agent. In some embodiments, a linker moiety is added to a sensor agent via coupling chemistry for attachment to the second entity. In some embodiments, a linker moiety (e.g. a moiety which connects a sensor agent and a second entity) is provided. The present invention is not limited to any particular linker moiety. Indeed, a variety of linker moieties are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, a linker comprises any combination of alkyl, alkenyl, alkynyl, phenyl, benzyl, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention.

In some embodiments, sensor agents are tethered to cellular, extracellular, biological, and/or pathogenic components (e.g., protein, nucleic acid, small molecule, lipid, polysaccharide, virus, etc.). In some embodiments, sensor agents are tethered to a cell surface analyte or extracellular analyte to monitor internalization thereof. In some embodiments, the cell-surface analyte is a cell surface component (e.g., lipid, receptor, etc.). In some embodiments, the cell surface component comprises a cell surface receptor (e.g., an ion channel-linked receptor (e.g., acetylcholine receptor), enzyme-linked receptor (e.g., receptor tyrosine kinases; tyrosine kinase associated receptors; receptor-like tyrosine phosphatases; receptor serine/threonine kinases; receptor guanylyl cyclases, histidine kinase associated receptors), and/or G-protein-coupled receptor/7-transmembrane receptor). Particular transmembrane receptors that find use in embodiments described herein include, but are not limited to: angiotensin2-type1a receptor (AT1R), vasopressin 2 receptor (V2R), delta-opioid receptor (OPRD1) and epidermal growth factor receptor (EGFR) delta opioid receptor, vasopressin 2 receptor, EDG1 receptor, β2-adrenergic receptor (ADRB2), arginine vasopressin receptor 2 (AVPR2), serotonin receptor 1a (HTR1A), m2 muscarinic acetylcholine receptor (CHRM2), chemokine (C-C motif) receptor 5 (CCR5), dopamine D2 receptor (DRD2), kappa opioid receptor (OPRK), or α1a-adregenic receptor (ADRA1A), the insulin growth factor-1 receptor (IGF-R), etc. It is to be understood that the methods and compositions of the present invention are not limited to the cell surface components (e.g., cell membrane proteins) listed herein. In some embodiments, the fluorescent signal from a sensor agent (or lack of a signal) is detected and/or monitored to detect the internalization of the tethered component. In some embodiments, upon internalization (e.g., endocytosis, phagocytosis, etc.), the tethered component transfers from a neutral pH environment to an acidic environment. In some embodiment, internalization of the tethered component is detected and/or monitored by detecting or monitoring fluorescence emission from the sensor agent. In some embodiments, receptor internalization (e.g., endocytosis) involves a change of pH from near neutral to acidic. In some embodiments, sensor agents are provided that undergo an alteration in fluorescence upon internalization of an associated receptor. In some embodiments, a sensor is provided that undergoes an increase in fluorescent emission (e.g., from non-fluorescent to detectable fluorescence) upon moving from a neutral pH to an acidic pH (e.g., upon internalization of a receptor to which the sensor is attached).

In some embodiments, pH sensor agents and methods of use thereof for monitoring, detecting, or quantitating cellular internalization and/or endocytosis are provided. In some embodiments, compositions and methods described herein are useful for monitoring any type of endocytosis, e.g., clathrin-mediated, caveole, macropinocytosis, or phagocytosis. In some embodiments, endocytosis is monitored irrespective of the endocytosis pathway and/or endocytic components involved in the process. In some embodiments, compositions and methods provided herein detect and monitor pH changes associated with cellular internalization, thereby detecting and/or monitoring cellular internalization (e.g., endocytosis). In some embodiments, compositions and methods are configured to detect all types of cellular internalization and/or endocytosis. In some embodiments, compositions and methods to detect dynamin-dependent endocytosis are provided. In some embodiments, compositions and methods are provided to detect one or more types of endocytosis, e.g., clathrin-mediated, caveole, macropinocytosis, phagocytosis, and/or dynamin-dependent. In some embodiments, compositions and methods are provided to detect a single type of endocytosis, e.g., clathrin-mediated, caveole, macropinocytosis, dynamin-dependent, or phagocytosis.

In some embodiments, a pH sensor agent is a substrate for an enzyme (e.g., hydrolase, dehalogenase, etc.) or is attached to a substrate for an enzyme. In some embodiments, a pH sensor agent is a substrate or is attached to a substrate for an enzyme (e.g., hydrolase, dehalogenase, etc.) or mutant enzyme (e.g., one that forms a covalent attachment to the sensor agent or attached substrate upon interaction). In some embodiments, a pH sensor is covalently or non-covalently attached to an enzyme engineered to form a highly stable and/or covalent bond with its substrate. In some embodiments, a pH sensor is covalently or non-covalently attached to a substrate of an enzyme engineered to form a highly stable and/or covalent bond with its substrate. Such enzymes and substrates are described, for example in U.S. Pat. No. 7,935,803; U.S. Pat. No. 7,888,086; U.S. Pat. No. 7,867,726; U.S. Pat. No. 7,425,436; and U.S. Pat. No. 7,238,842; each of which are herein incorporated by reference in their entireties. In some embodiments, interaction (e.g., covalent) of a pH sensor (or attached enzyme substrate) with an enzyme (e.g., one engineered to form a highly stable and/or covalent bond with its substrate) allows for monitoring the pH in the local environment of the enzyme. In some embodiments, the enzyme is part of a fusion protein. In some embodiments, the fusion protein is localized to a specific region or compartment within a biological system (e.g., cell). In some embodiments, the fusion protein is localized to the cell surface, cell membrane, organelle membrane, cytoplasm, an organelle (e.g., mitochondria, nucleus, etc.), etc. In some embodiments, localization of the fusion protein results in localization of the pH sensor (e.g., through covalent interactions between the fusion protein, the enzyme substrate, and the pH sensor).

In some embodiments, a pH sensor finds use in any suitable fluorescence-based assays (e.g., Forster Resonance Energy Transfer (FRET), Fluorescence Recovery After Photobleaching (FRAP), Fluorescence Loss in Photobleaching (FLIP), Fluorescence Localization After Photobleaching (FLAP), Fluorescence Correlation Spectroscopy (FCS), Fluorescence Cross-Correlation Spectroscopy (FCC S), Fluorescence Lifetime IMaging (FLIM), Bioluminescence Resonance Energy Transfer (BRET), etc. In some embodiments, energy transfer to and/or from a pH sensor is only possible and/or detectable under suitable pH conditions (e.g., acidic pH).

In some embodiments, a pH sensor agent is attached, tethered, coordinated, and/or conjugated to a carrier (e.g., protein, peptide, polysaccharide, small molecule, lipid, nucleic acid, polynucleotide, macromolecular complex, etc.). Suitable carriers may be water soluble or water insoluble. In some embodiments, any carrier that does not interfere with the pH sensing capacity of a sensor agent finds use in embodiments of the present invention. In some embodiments, any carrier that does not interfere with the fluorescence, solubility, stability, membrane permeability, pKa, excitation maximum, emission maximum, maximum fluorescence intensity, range of zero fluorescence, etc. of a sensor agent finds use in embodiments of the present invention. In some embodiments, a carrier facilitates cellular uptake of a pH sensor. In some embodiments, a carrier facilitates cellular localization of a pH sensor. In some embodiments, a carrier enhances the stability, solubility, membrane permeability, etc. of a pH sensor. In some embodiments, a pH sensor agent is coordinated to a polysaccharide (e.g., branched glucan (e.g., dextran)). In some embodiments, polysaccharide-conjugated sensor agent is water-soluble, stable within a biological system (e.g., cell), and/or capable of being internalized by phagocytotic and/or endocytic pathways. Suitable water soluble carriers include, but are not limited to: dextran, sepharose, coated beads, quantum dots, non-pH-sensitive fluorophores, nanoparticles, etc. Tethering of a pH sensor to a quantum dot or other non-pH-sensitive fluorophore (or other detectable moiety) allows for pH sensing and localization (e.g., irrespective of the local pH). Dextran provides numerous advantages as a carrier molecule for a pH sensor including being membrane impermeable without endocytosis and allowing for global internalization. In certain embodiments, multiple sensor agents are tethered to a single dextran (or other carrier). In some embodiments, one or more sensor agents and one or more other detectable agents (e.g., optical labels, contrast agents, fluorescent labels, etc.) are tethered to a single dextran (or other carrier).

In some embodiments, a pH sensor is conjugated to an antibody (e.g., secondary antibody) or other targeting moiety that specifically associates with a partner entity. In some embodiments, antibody-conjugated sensor agents provide monitoring of the pH environment of an antibody. In some embodiments, antibody-conjugated sensor agents provide detection or monitoring of cellular internalization of antibodies (e.g., recombinant antibodies). In some embodiments, antibody-conjugated pH sensors monitor antibody induced internalization. For example, various cancer cells express a cell membrane antigen(s). Screening antibodies that can bind to the antigen(s) and are internalized by the cancer cells can provide a powerful tool to aid in developing novel therapeutic methods to target toxins, drugs or short-range isotopes to be delivered specifically to the interior of the cancer cells. In some embodiments, internalization of antibodies upon binding to cell surface antigen is monitored by an antibody-tethered pH sensor agent.

In some embodiments, a pH sensor is targeted to a specific tissue, cell type, cellular region, sub-cellular region, etc. (e.g., by tethering (e.g., directly or indirectly) to a targeting moiety or cellular component (e.g., surface receptor)). In some embodiments, targeted sensor agents allow measuring and/or monitoring (e.g., at time points or in real-time) of the pH at specific locations (e.g., cell surface, cytoplasm, epicardium, etc.).

In some embodiments, sensor agents further comprise contrast agent functionality and provide utility in imaging (e.g., CT, MRI, PET, nuclear medicine, etc.). In some embodiments, a sensor agent is tethered to a contrast agent. In some embodiments, sensor agents with contract agent functionality find use in in vivo imaging applications.

In some embodiments, kits containing components, reagents, sensor agents (e.g., reactive sensor agents), controls, substrates, and/or materials (e.g., multiwell plates, cells) are provided. In some embodiments, kits are provided for performing the methods or assays described herein.

In some embodiments, methods and assays that are performed in a multiplex format are provided. In some embodiments, methods and assays are performed in a high throughput manner. In some embodiments, assays provided herein are rapidly performed in a multiwell plate, e.g., 96-well, 384-well, etc. In some embodiments, assays and methods provide a high-throughput screening compatible mix and read format (e.g., non-image based, flow-based, etc.).

In some embodiments, systems, devices, or apparatuses for assessing, quantitating, detecting, and/or monitoring the compositions, methods, and/or assays are provided. In some embodiments, systems, devices, and/or apparatuses are provided to detect, quantitate, or monitor, the amount of fluorescence emitted by a sensor or sensors, or changes therein. In some embodiments, detection, quantification, and/or monitoring are provided by a device, system or apparatus comprising one or more of a spectrophotometer, fluorometer, luminometer, photomultiplier tube, photodiode, nephlometer, photon counter, electrodes, ammeter, voltmeter, capacitative sensors, flow cytometer, CCD, etc. In some embodiments, methods and assays are provided for correlating fluorescence detection to chemical (e.g., change in pH) and/or biological (e.g., endocytosis, intracellular trafficking, pathogenicity, etc.) phenomena. In some embodiments, a device suitable for detection of a sensor agent is selected and/or provided.

EXPERIMENTAL

Example 1

Fluorescence of pH Sensor Agents

Experiments were conducted during development of embodiments of the present invention to determine the fluorescence characteristics of exemplary pH sensor agents PBI-4453 and PBI-4479 (SEE FIG. 1). Fluorescence excitation and emission intensities were measured at a range of wavelengths (SEE FIG. 2). Compound PBI-4453 exhibits an excitation maximum of 541 nm and an emission maximum of 571 nm (SEE FIG. 2A). Compound PBI-4479 exhibits an excitation maximum of 534 nm and an emission maximum of 562 nm (SEE FIG. 2B). Fluorescence detection was performed at a range of pH values (SEE FIG. 3). Compound PBI-4453 has a pKa of about 5.84, exhibits maximal fluorescence intensity at pH 4.15 or below, and exhibits about 5% or less of maximal fluorescence at pH 7.53 or higher (SEE FIG. 3A). Compound PBI-4479 has a pKa of about 6.1, exhibits maximal fluorescence intensity at pH 3 or below, and exhibits about 1% or less of maximal fluorescence intensity at pH 8 or higher (SEE FIG. 3B).

Example 2

Stability

PBI-4479 was dissolved to 2 mM in DMSO to approximately 2.33 mg/mL. Aliquots of 350 uL from the 2 mM solution were stored shielded from light at −20° C., 4° C. and room temperature. Stability was established by measuring fluorescent emission intensity and by testing HPLC purity at time 0, 1 day, 1 week, 1 month, 4 months, and 6 months from when the solutions were prepared and stored. For the fluorescence measurements, each aliquot was diluted (1 uL) into 4 mL of 0.1M sodium phosphate pH 4.0 directly into a 4.5 mL plastic cuvette and mixed by inversion of the vial. The maximum emission peak at 562 nm was acquired using a HoribaJobinYvon fluorometer using an excitation of 532 nm with 1.5 nm slit width. For HPLC measurements, each aliquot was diluted to 1 mM in 0.1M sodium phosphate pH 4.0, and 2 uL tested. The purity of each aliquot was tested using an Agilent 1100 liquid chromatography system equipped with a quaternary pump and a diode-array detector. The diode-array detector was set at 254 nm and 532 nm. The elution was performed using a mobile phase (A) containing 0.1% TFA in water, and a mobile phase (B) containing HPLC grade acetonitrile. A Phenomenex Synergi MAX-RP column (50×4.6 mm; 2.6 μm) was used to perform the chromatography. The HPLC was performed as follows: a gradient ran 3% to 60% mobile phase (B) to 3.60 minutes, a hold at 60% mobile phase (B) for 1 minute, a ramp up to 100% mobile phase (B) to 6 minutes, another hold at 100% mobile phase (B) for 2 minutes, and then back to 3% mobile phase (B) for 1.5 minutes. The column was given 2.5 minutes to re-equilibrate back to the starting conditions. In these conditions, the product elutes at approximately 3.7 minutes. Purity (as area percent) of the product was reported at 254 nm and 532 nm.

The results for both fluorescent emission intensity and purity by HPLC show very little variation over the 180 day study (See Table 1 and FIGS. 4-8). The relative standard deviations (RSD) for each data set are low, indicating minimal chemical change in the dye. A slight degradation is observed by fluorescence intensity when the solution is stored at room temperature. Based on these data, compound PBI-4479 is stable below room temperature for at least 180 days.

TABLE 1

| Time (days) | Temperature | | | | | |
|---|---|---|---|---|---|---|
| | −20 | | 4 | | RT | |
| | HPLC Purity @ 532 nm | Emission intensity | HPLC Purity @ 532 nm | Emission intensity | HPLC Purity @ 532 nm | Emission intensity |
| 0 | 91.1 | 2109020 | 91.8 | 2109020 | 91.8 | 2109020 |
| 1 | 93.9 | 2336260 | 92.5 | 2203160 | 91.3 | 2641010 |
| 7 | 92.7 | 2006990 | 93.9 | 2055280 | 92.5 | 2092940 |
| 30 | 95.8 | 2191770 | 95.7 | 2076310 | 95.1 | 2158320 |
| 110 | 95.2 | 1926570 | 93.9 | 2040510 | 91.8 | 1967130 |
| Ave | 93.7 | 2114122.0 | 93.6 | 2096856.0 | 92.5 | 2193684.0 |
| SD | 1.9 | 159729.1 | 1.5 | 64757.4 | 1.5 | 259805.3 |
| 1 SD High | 95.6 | 2273851.1 | 95.1 | 2161613.4 | 94.0 | 2453489.3 |
| 1 SD Low | 91.8 | 1954392.9 | 92.1 | 2032098.6 | 91.0 | 1933878.7 |
| 2 SD | 3.8 | 319458.2 | 3.0 | 129514.8 | 3.0 | 519610.6 |
| 2 SD High | 97.5 | 2433580.2 | 96.6 | 2226370.8 | 95.5 | 2713294.6 |
| 2 SD Low | 89.9 | 1794663.8 | 90.6 | 1967341.2 | 89.5 | 1674073.4 |
| RSD | 2.0 | 7.6 | 1.6 | 3.1 | 1.6 | 11.8 |

Example 3

Toxicity

Figure 9:
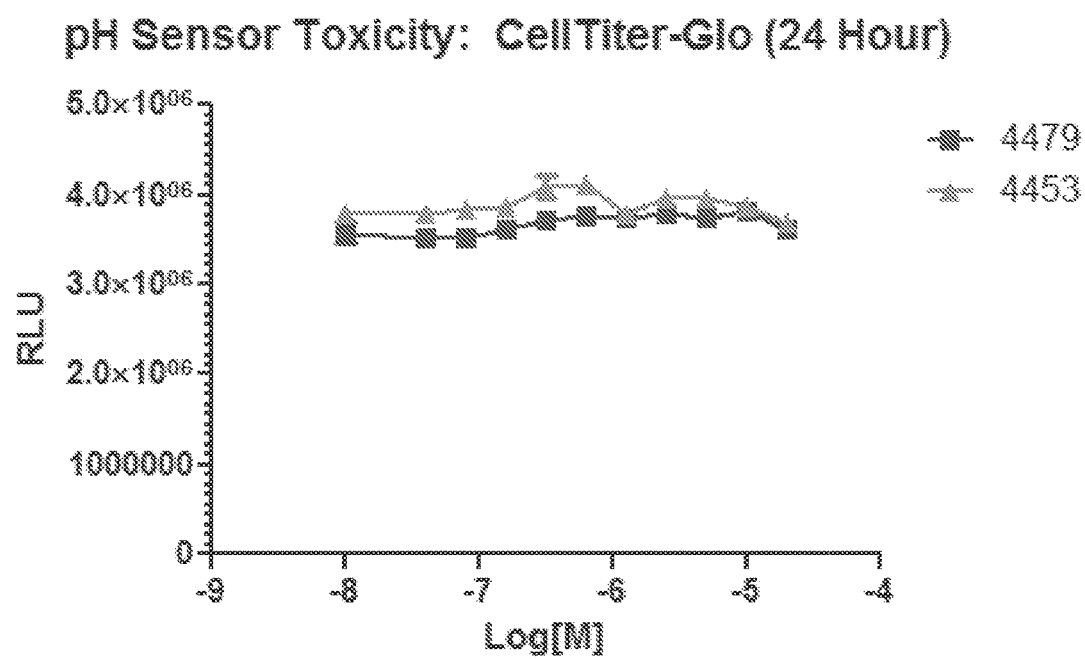
FIG. 9 shows a graph demonstrating the toxicity profiles of PBI-4479 and PBI-4453 in U2-OS cells.

The toxicity of dyes PBI-4479 and PBI-4453 was tested in U2OS cells. The cells were plated at 20,000 cells/well in McCoy's 5A media+10% FBS into wells of a 96-well plate. The compounds were then serially diluted 2-fold in McCoy's 5A+10% FBS to a 10× working solution. 10 ul of the working solution was added to the cells to a final concentration of 0 nM to 20 uM. The treated cells were then incubated overnight at 37° C., 5% $CO_2$. Toxicity was tested using Promega's CELLTITER-GLO Luminescent Cell Viability Assay according to the manufacturer's protocol. No toxicity was seen across varying concentrations of the compounds over the 24 hour period (SEE FIG. 9).

Example 4

Permeability and Specificity

Figure 10:
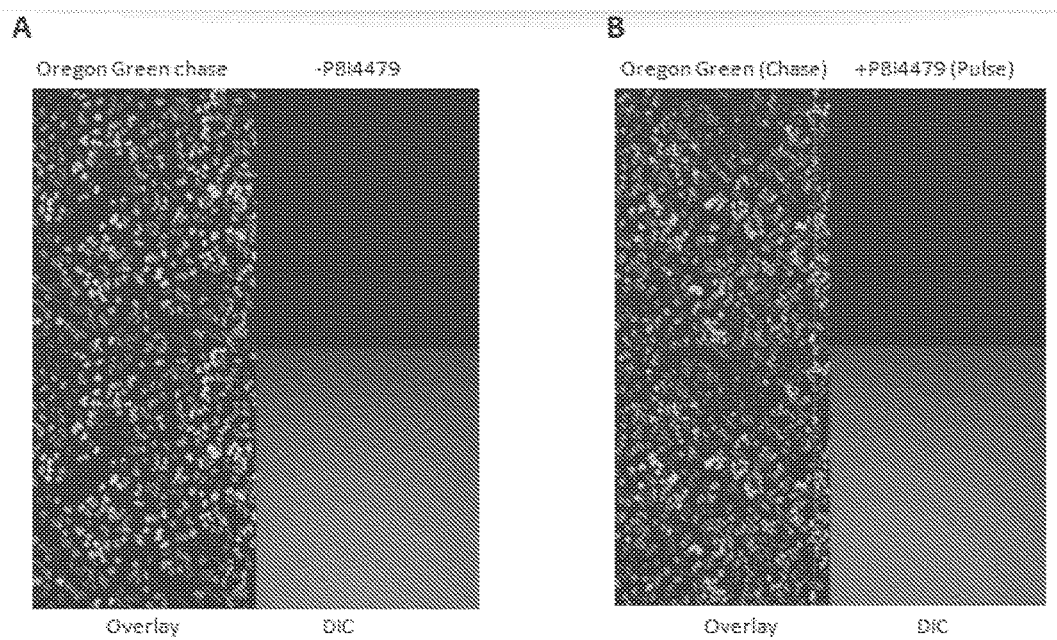
FIG. 10 shows a luminescent cell viability assay demonstrating the impermeability of PBI-4479 in U2-OS HaloTag-NLS cells.
Figure 11:
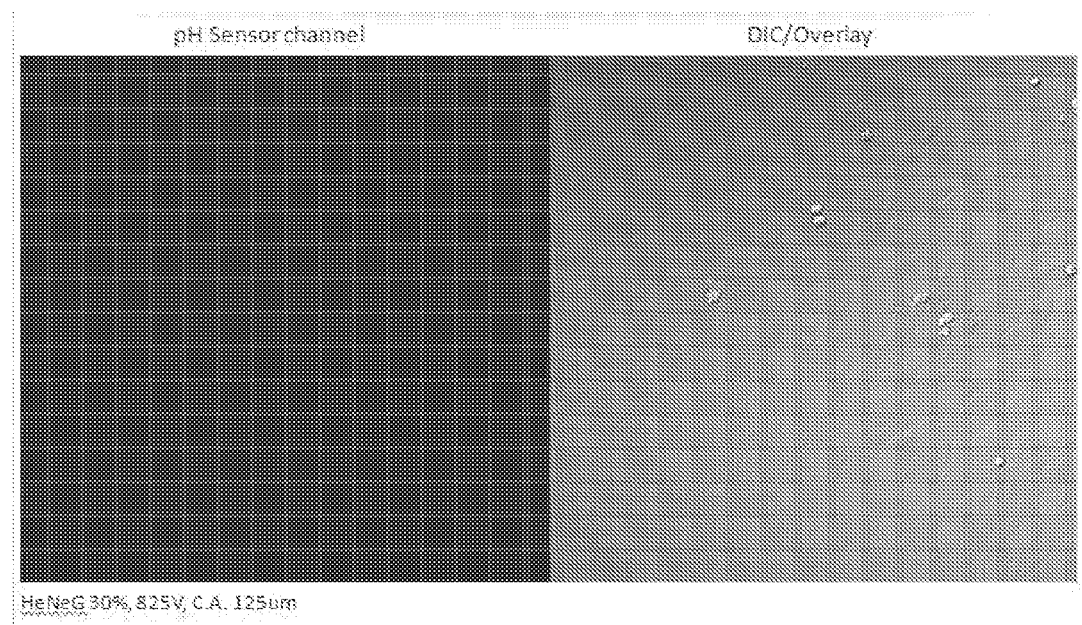
FIG. 11 shows the lack of non-specific labeling by PBI-4479 in U2-OS cells.
Figure 12:
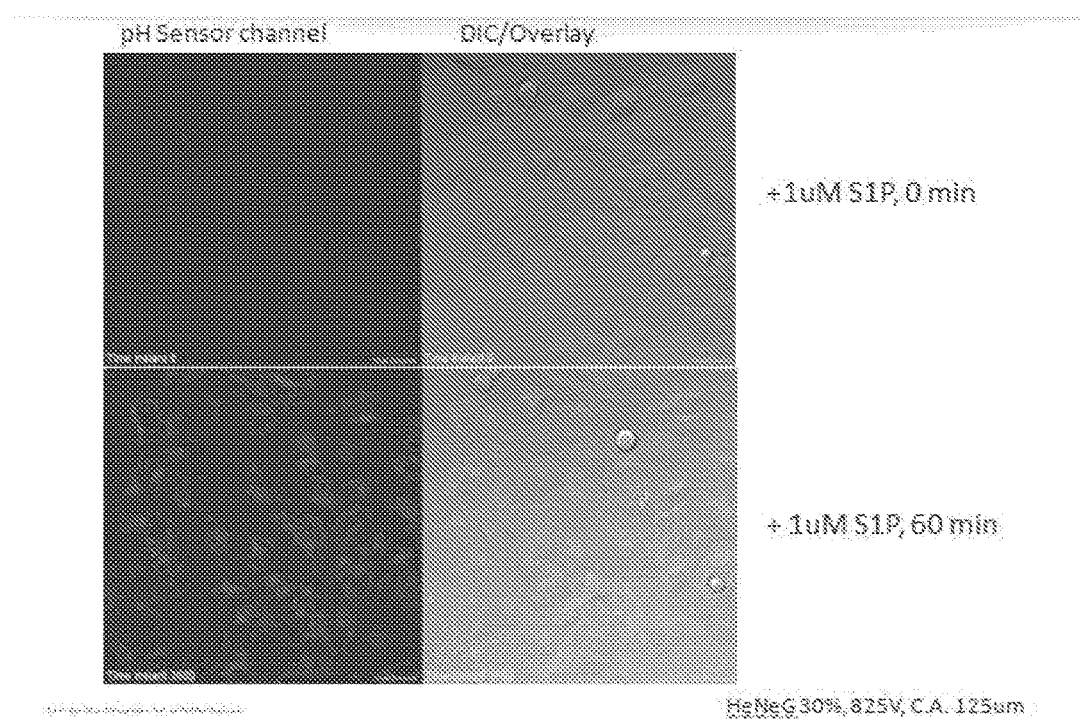
FIG. 12 shows detection of HaloTag-EDG1 internalization using PBI-4479.
Figure 13:
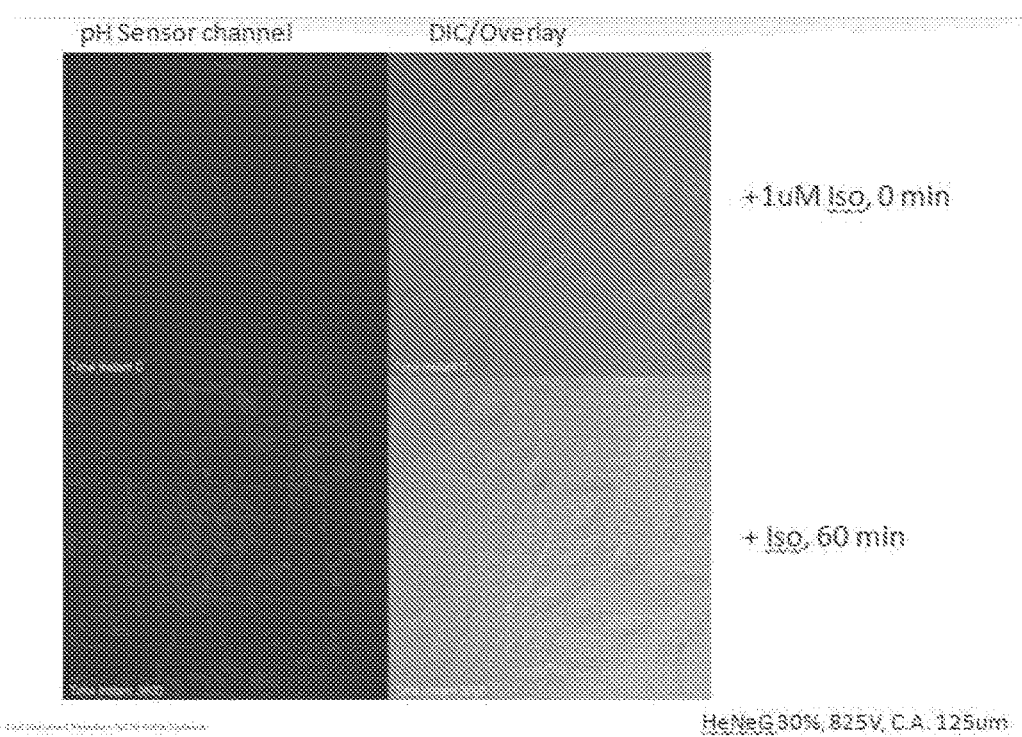
FIG. 13 shows detection of HaloTag-B2AR internalization using PBI-4479.
Figure 14:
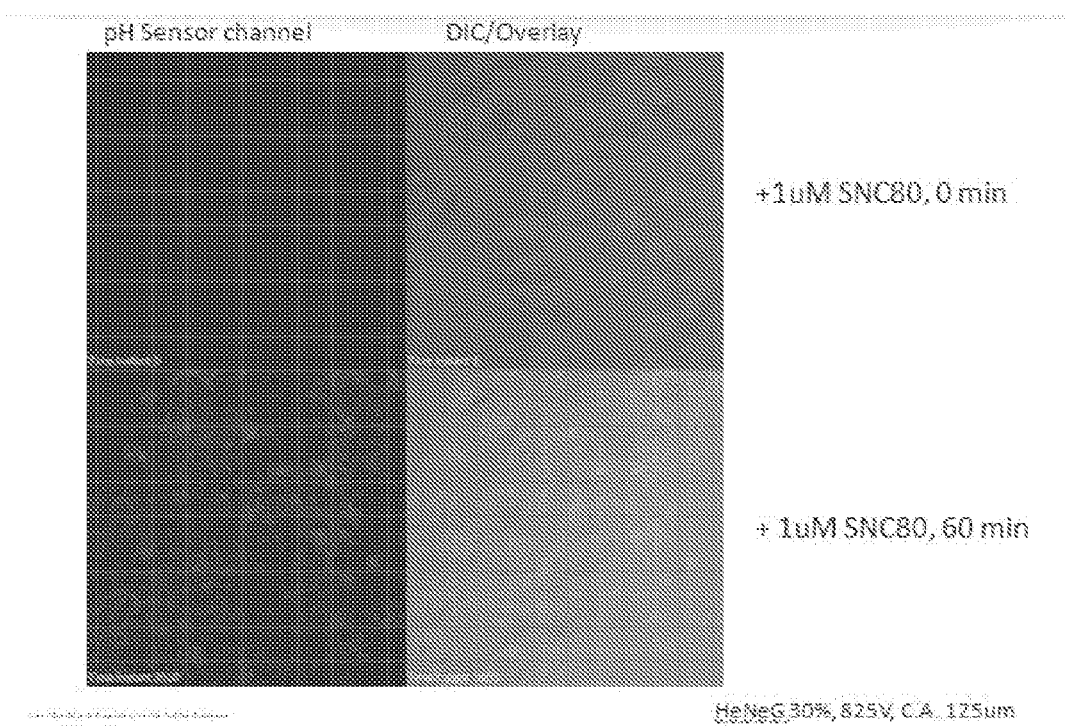
FIG. 14 shows detection of HaloTag-DOR1 internalization using PBI-4479.
Figure 15:
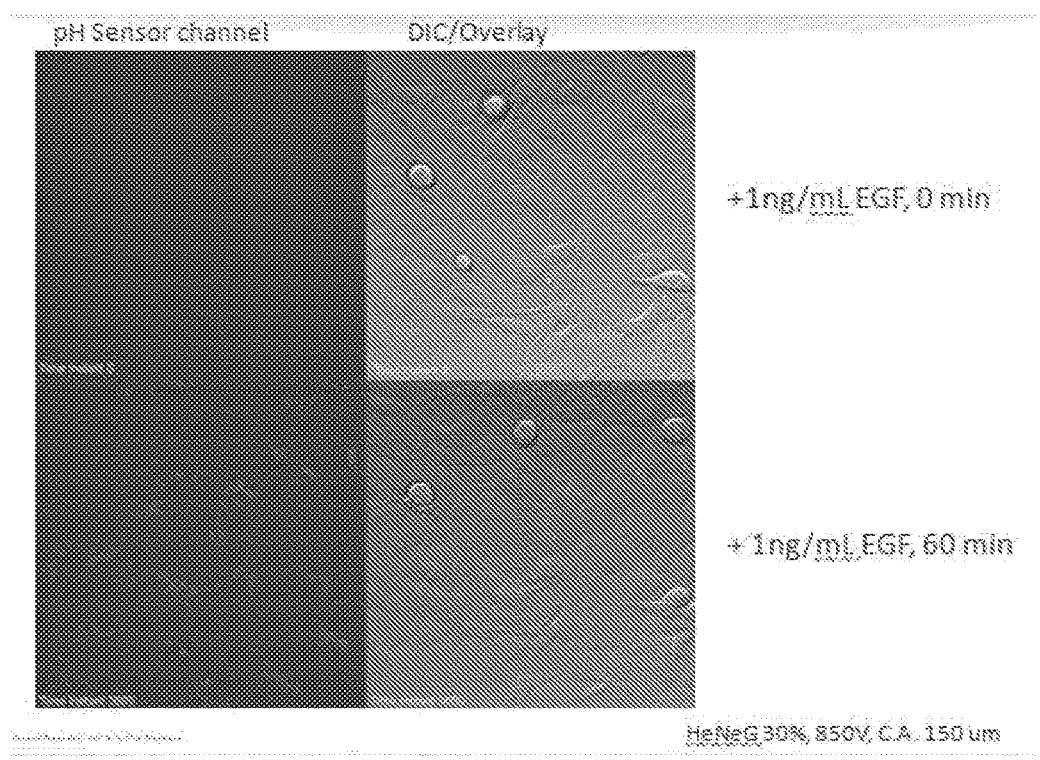
FIG. 15 shows detection of HaloTag-EGFR internalization using PBI-4479.

Experiments were conducted during development of embodiments of the present invention to determine the permeability and specificity of the pH sensor. U2-OS cells (for specificity) and U2-OS NLS cells (U2-OS cells stably expressing a HaloTag protein with a nuclear localization sequence (NLS); for permeability) were treated with the PBI-4479 sensor. Cells were plated at 40,000 cells/well in 200 ul McCoy's 5A media+10% FBS ("complete media") onto LTII chamber slides. The cells were then incubated overnight at 37° C., 5% $CO_2$. The cells were then pulsed with PBI-4479 from 0-20 uM for 1 hour. The media was then removed from the cells and chased with 1 uM Oregon Green in McCoy's 5A+10% FBS for 15 minutes followed by three, 5 minute washes in complete media. Cells were then imaged on an Olympus FV500. The results demonstrate that PBI-4479 is impermeable and does not label HaloTag-NLS stably expressed in U2-OS cells (SEE FIG. 10). Further, PBI-4479 does not non-specifically bind or label wild-type U2-OS cells (SEE FIG. 11).

Example 5

GPCR and Non-GPCR Internalization

Figure 16:
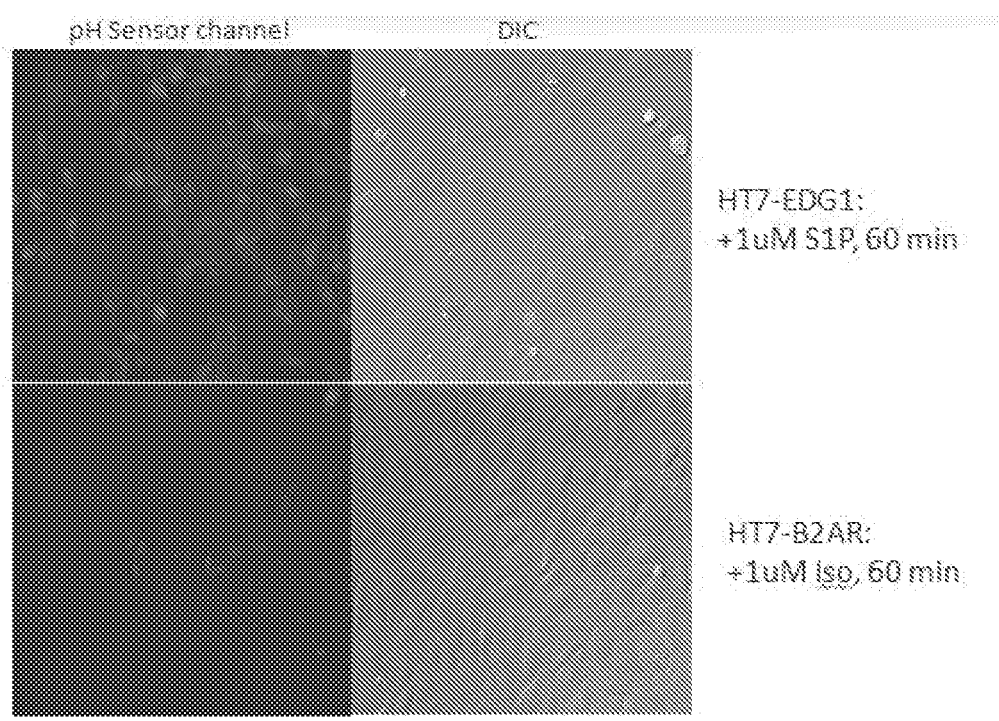
FIG. 16 shows detection of receptor internalization by epifluorescence.

Experiments were conducted during development of embodiments of the present invention to detect and monitor internalization/endocytosis. U2-OS cells expressing (either transiently or stably) a HaloTag (HT7)-Receptor fusion protein containing an IL6 signal sequence were used. The following HT7-receptor fusion proteins were expressed in the U2-OS cells: IL6-HT7-β2AR (β2 adrenergic receptor; NM_000024.3), IL6-HT7-EDG1 (endothelial differential growth gene 1; NM_001400), IL6-HT7-DOR1 (δ-opioid receptor; NM 000911) and IL6-HT7-EGFR (epidermal growth factor receptor; AB528482). The cells were plated at $2 \times 10^5$ cells/mL in complete media into wells. The cells were then incubated overnight at 37° C., 5% $CO_2$. The media was then replaced with 200 ul McCoy's 5A media with 0.5% charcoal-stripped FBS (Hyclone) and incubated for about 1 hour at 37° C., 5% $CO_2$. The cells were then labeled with 1 uM pH sensor PBI-4479 and incubated for 10 minutes at 37° C., 5% $CO_2$. The cells were then washed 3 times with 200 ul complete media to remove any unbound sensor. The cells were then stimulated with the respective agonist (1 uM Isoproterenol for IL6-HT7-β2AR, 1 uM S1P for IL6-HT7-EDG1, 1 uM SNC80 for IL6-HT7-DOR1, and 1 ng/mL rhEGF for IL6-HT7-EGFR) and imaged every 5 minutes for 1 hour on an Olympus FV500. The experiments demonstrate the ability of the pH sensor to detect internalization and monitor trafficking of various receptors (e.g., G-protein coupled receptors and tyrosine kinase receptors; SEE FIGS. 12-15), and that epifluorescence (detection not limited to confocal detection) can be used to detect internalization and monitor trafficking with the pH sensor (SEE FIG. 16).

Example 6

Blocking Internalization

Experiments were conducted during development of embodiments of the present invention to demonstrate the capability of the pH sensors described herein to detect and monitor the blocking of internalization/endocytosis.

Figure 17:
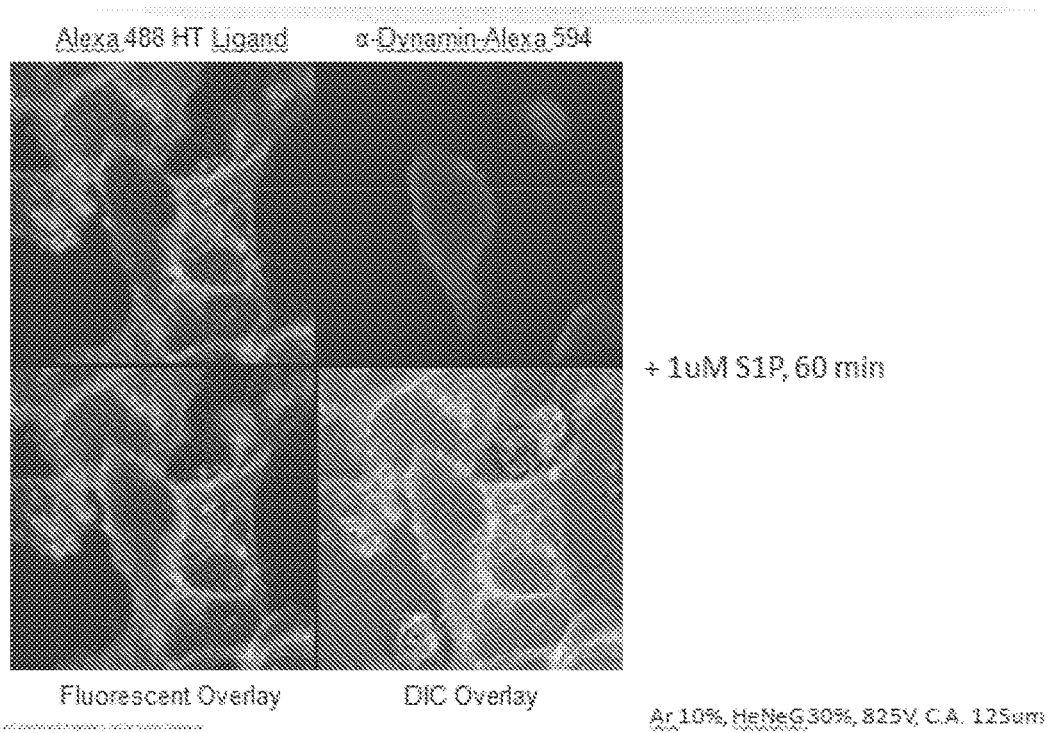
FIG. 17 shows prevention of HaloTag-EDG1 internalization by Dynamin (K44A).

U2-OS cells stably expressing a HaloTag-EDG1 fusion protein were plated as described in Example 5. After the overnight incubation, the cells were transiently transfected with Dynamin K44A+/−FLAG (provided by Dr. R. Lefkowitz at Howard Hughes Medical Institute), a dominant-negative mutant that prevents receptor mediated endocytosis, using Mirus' TransIT®-LT1 Transfection Reagent according to the manufacturer's protocol. Twenty-four hours post-transfection, the cells were labeled with an impermeable, 1 uM HaloTag-Alexa 488 ligand for 5 minutes in McCoy's 5A+10% FBS. The unbound ligand was removed by quickly washing three times with 200 ul McCoy's 5A+10% FBS. The cells were stimulated with 1 uM S1P (D-erythro sphingosine-1-phosphate; an EDG1 agonist) for 60 minutes and then fixed with 3.7% PFA (paraformaldehyde), permeabilized with 0.1% Triton X-100, blocked with 3% NGS (normal goat serum) and labeled with primary antibody α-M2 FLAG (Sigma 1:500) and goat α-mouse Alexa 594 (Molecular Probes-Life Technologies). Images were captured as previously described. Dynamin prevented the internalization of the HaloTag-EDG1 protein (SEE FIG. 17). The pH sensor was not used in this particular experiment. However, it is supporting evidence that the system is working, e.g., expression, labeling, localization and blocking were all functioning as expected.

Figure 18:
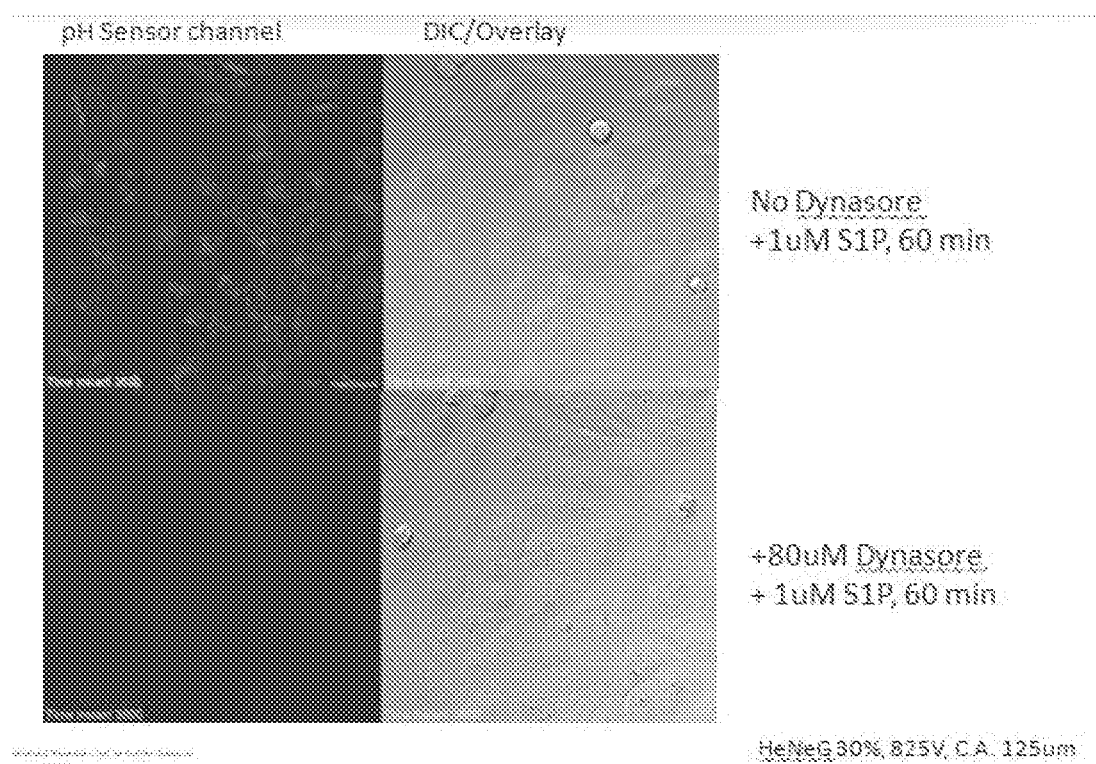
FIG. 18 shows blocking of HaloTag-EDG1 internalization by DYNASORE.

In addition to dynamin, DYNASORE, a reversible, non-competitive inhibitor of dynamin, can also be used to block internalization/endocytosis with the blocking detected and monitored using the pH sensor of the present invention. U2-OS cells stably expressing a HaloTag-EDG1 fusion protein were plated as described above. After the overnight incubation, the cells were simultaneously labeled for 30 minutes with 1 uM HaloTag pH sensor (PBI-4479) and 80 uM Dynasore (Sigma). Control cells were labeled with the 1 uM HaloTag pH sensor, but were not treated with Dynasore. The cells were then stimulated with 1 uM S1P for 60 minutes and imaged as previously described. DYNASORE prevented dynamin-dependent internalization/endocytosis of HaloTag-EDG1 in the presence of an agonist as detected by the pH sensor (SEE FIG. 18).

Example 7

Restoration of Internalization

Figure 19:
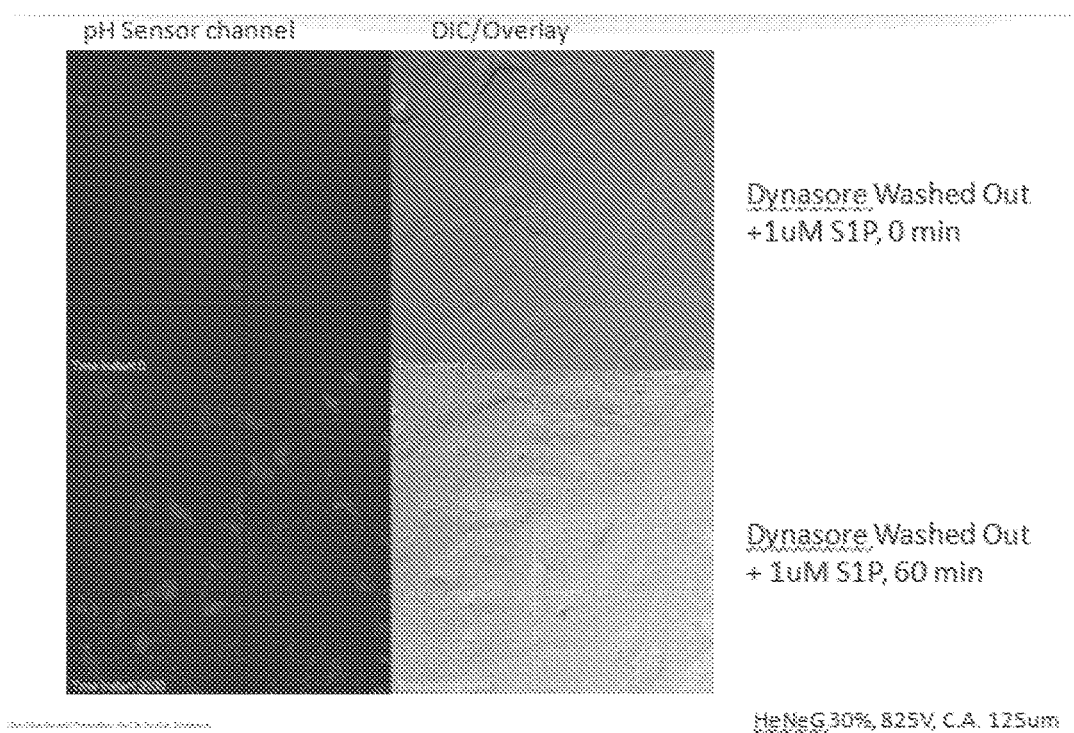
FIG. 19 shows restoration of HaloTag-EDG1 internalization by DYNASORE washout.

Experiments were conducted during development of embodiments of the present invention to further demonstrate the ability of the pH sensors to monitor and detect internalization. In such experiments, blocked internalization of HaloTag-EDG1 was restored. U2-OS cells stably expressing a HaloTag-EDG1 fusion protein were plated as described above. After the overnight incubation, the cells were simultaneously labeled with a HaloTag pH sensor (PBI-4479) and 80 uM DYNASORE (Sigma). Control cells were labeled with the HaloTag pH sensor, but were not treated with DYNASORE. The cells were then stimulated with 1 uM S1P and imaged (T=0 in FIG. 17). At this point, DYNASORE prevents the dynamin-dependent internalization/endocytosis of HaloTag-EDG1. DYNASORE was then removed by washing three times for 5 minutes with McCoy's 5A+10% FBS, and the media replaced with complete media containing 1 uM S1P. The cells were incubated for 60 minutes and imaged as previously described. Internalization of HaloTag-EDG1 was restored as detected and monitored by the pH sensor (SEE FIG. 19).

Example 8

Exemplary pH Sensor Agents and Precursor Molecules

Figure 20:
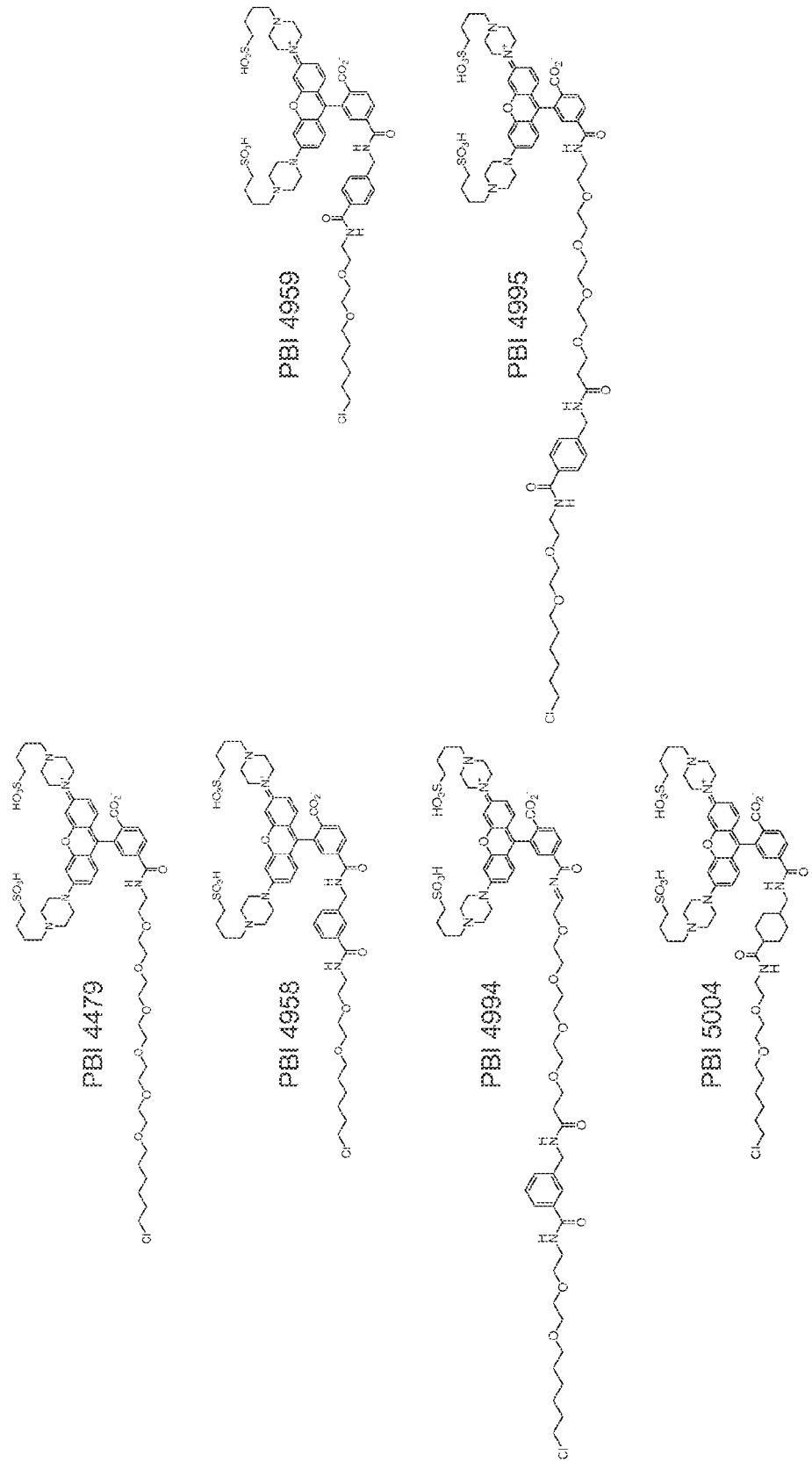
FIG. 20 shows exemplary pH sensor agents.

Various pH sensors and precursor molecules were produced during development of embodiments of the present invention (SEE FIG. 20).). Provided below are structures and synthesis procedures for examples of such sensor agents and precursors. These molecules are intended as examples and should not be viewed as limiting the scope of the present invention.

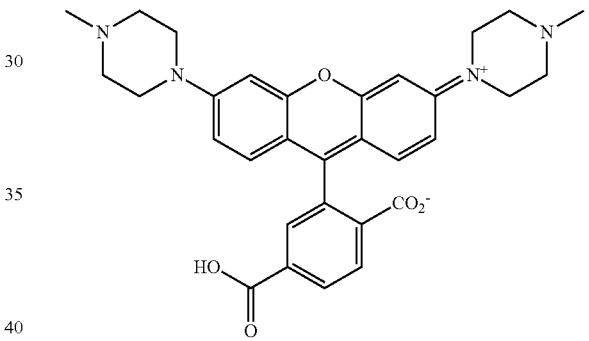

3',6'-bis(4-methylpiperazin-1-yl)-rhodamine(5,6)-carboxylic acid

In a pressure tube, 3',6'-diiodo-rhodamine(5',6') carboxylic acid (50.0 mg, 0.084 mmol), 1-methyl-piperazine (33.5 mg, 0.334 mmol), potassium tert-butoxide (18.8 mg, 0.167 mmol), CuI(15.9 mg, 0.083 mmol) and 22,2,2-trifluoroethanol (5 ml) were heated to 110° C. in an oil bath for 11 days. Volatiles were removed under reduced pressure and the residue was taken up in 1:1:0.1 ACN/water/TFA. Solids were filtered and the crude mixture was subjected to RP-HPLC giving an orange solid (29.0 mg, 64.2%) upon concentration.

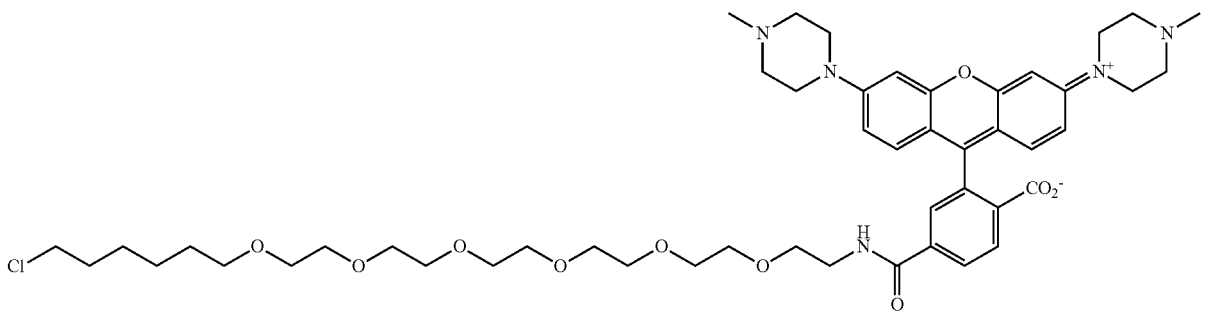

N-(24-chloro-3,6,9,12,15,18-hexaoxatetracosyl)-3',6'-bis(4-methylpiperazin-1-yl)-rhodamine-(5,6)carboxamide (PBI-4453)

To 3',6'-bis(4-methylpiperazin-1-yl)-rhodamine(5,6)-carboxylic acid (29.0 mg, 0.053 mmol) in DMF (3 ml), O—(Nsuccinimidyl)-N,N,N',N'-tetramethyluronium tetrafluoroborate (19.4 mg, 0.0644 mmol) and diisopropylethylamine (46.7 µl, 0.268 mmol) was added. The reaction mix was stirred for 3 hrs. before adding 24-chloro-3,6,9,12,15,18-hexaoxatetracosan-1-amine-HCl as a 0.4M solution in $CH_2Cl_2$ (46.71, 0.268 mmol) and diisopropylethylamine (160.9 µl, 0.064 mmol). The reaction was stirred overnight, and the volatiles removed under reduced pressure giving a dark solid that was dissolved in 1:1:0.01 ACN/water/TFA and subjected to RP-HPLCHPLCHPLC chromatography to give the product as a red solid. MS (ESI) m/z calcd for $C_{49}H_{68}ClN_5O_{10}$ (M+H$^+$) 921.5. found 922.6.

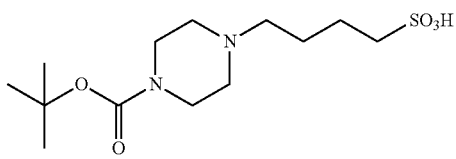 [SMILES: CC(C)(C)OC(=O)N1CCN(CCCCS(=O)(=O)O)CC1]

4-(4-(tert-butoxycarbonyl)piperazin-1-yl)butane-1-sulfonic acid

Butane sultone (1.15 ml, 11.28 mmol) and 1-Boc-piperazine (2.0 g, 10.74 mmol) in chlorobenzene (10 mL) were heated to 110° C. overnight giving a yellow precipitate. The mix was cooled to room temperature, solvent was decanted, and diethyl ether was added with vigorous stirring for 30 min. The resulting suspension was filtered to give the product (3.2 g, 92.4%) as a yellow solid. $^1$H-NMR (300 MHz, DMSO) δ 4.01 (t, 9.1 Hz, 2H), 3.45 (t, 11.8 Hz, 1H), 3.10 (m, 4H), 2.94 (m, 2H), 1.75 (m, 2H), 1.62 (m, 2H), 1.41 (s, 1H); MS (ESI) m/z calcd for $C_{13}H_{25}N_2O_5S$ (M−H$^+$) 321.2. found 321.2.

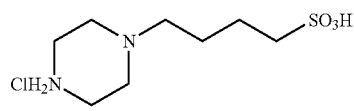

4-(piperazin-1-yl)butane-1-sulfonic acid, HCl salt 4-(4-(tert-butoxycarbonyl)piperazin-1-yl)butane-1-sulfonic acid (1.0 g, 3.10 mmol) in $CH_3OH$ (15 mL) and con HCl (1.5 mL) was stirred for 3 hrs. Volatiles were removed under reduced pressure, and the resulting yellow solid was dried overnight under hi-vac. $^1$H-NMR (300 MHz, DMSO) δ 3.67 (m, br, 8H), 3.61 (t, 7.2 Hz, 2H), 3.00 (t, 7.2 Hz, 2H), 2.00-1.83 (m, 4H); MS (ESI) m/z calcd for $C_8H_{19}N_2O_3S$ (M+H$^+$) 223.1. found 223.1.

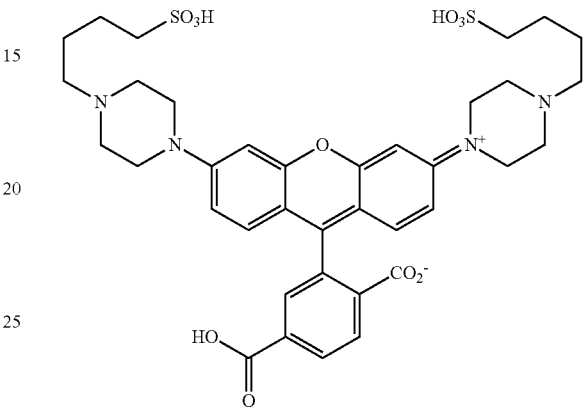

3',6'-bis(4-(4-sulfobutyl)piperazin-1-yl)rhodamine (5',6') carboxylic acid (PBI-4474)

3',6'-diiodorhodamine(5',6') carboxylic acid (50.0 mg, 0.084 mmol), 4-(piperazin-1-yl)butane-1-sulfonic acid-HCl (43.3 mg, 0.168 mmol), potassium-tert-butoxide (46.9 mg, 0.418 mmol) and CuI (31.8 mg, 0.168) were charged into a pressure tube and 2,2,2-trifluoroethanol (3 mL) was added. The tube was capped and heated to 110° C. in an oil bath for 10 days. Solvent was removed under reduced pressure, and the crude was suspended in 30 ml water, stirred for 10 min and centrifuged. The mother liquor was decanted, filtered, concentrated to 15 mL and subjected to RP-HPLC giving the product (6.5 mg, 9.5%) as a red solid. MS (ESI) m/z calcd for $C_{37}H_{45}N_4O_{11}S_2$ (M+H$^+$) 785.3. found 785.5.

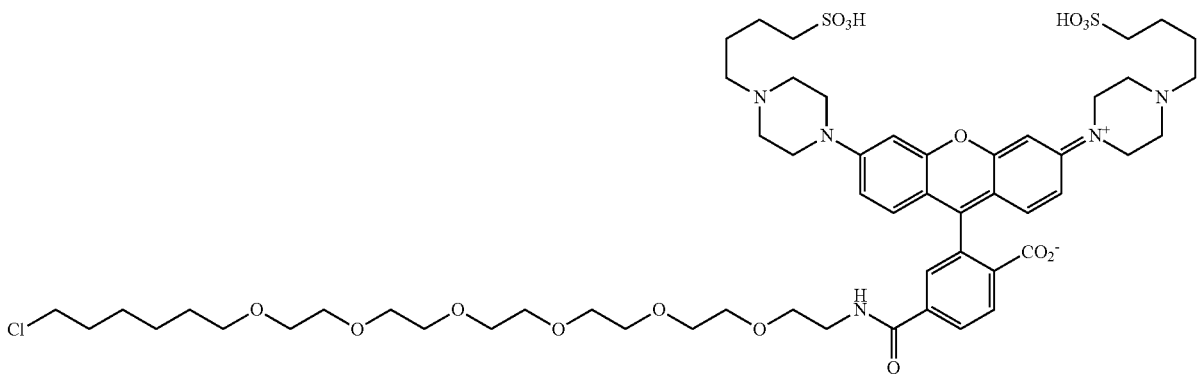

4,4'-(4,4'-((6',5')-((24-chloro-3,6,9,12,15,18-hexaoxatetracosyl)-3',6'-bis(4-(4-sulfobutyl)piperazin-1-yl) rhodamine(5',6') carboxamide (PBI-4479)

PBI-4474 (6.5 mg, 0.008 mmol), O—(N-succinimidyl)-N,N,N',N'-tetramethyluronium tetrafluoroborate (3.0 mg, 0.009 mmol) and diisopropylethylamine (7.21 μl, 0.041 mmol) were stirred in DMF (1 ml) for 1 hr. To the solution, 24-chloro-3,6,9,12,15,18-hexaoxatetracosan-1-amine-HCl as a 0.4M solution in $CH_2Cl_2$ (46.7 μl, 0.268 mmol) was added and allowed to stir for 1 hr. Volatiles were removed under reduced pressure, and the residue dissolved in water and subjected to RP-HPLCHPLC to give the product (9.6 mg, 96.4%) as a red solid. MS (ESI) m/z calcd for $C_5H_{81}ClN_5O_{16}S_2$ (M+H$^+$) 1166.5. found 1166.5.

PBI-4479-10,000 MW Amino Dextran (PBI-4627).

PBI-4474 (15.0 mg, 0.019 mmol), O—(N-succinimidyl-)—N,N,N',N'-tetramethyluronium tetrafluoroborate (6.9 mg, 0.023 mmol) and diisopropylethylamine (16.6 μl, 0.095 mmol) in 1 ml DMF was stirred for 2 hrs. Volatiles were removed under reduced pressure giving a red film that was dissolved in 0.1 M phosphate buffer. To the phosphate solution, 10,000 MW amino dextran (33 mg) was added, and the mixture stirred overnight in the dark. The resulting crude was purified by size exclusion chromatography (Sephadex® G-50, H2O eluent) to give the product as a red solid after lyophilization.

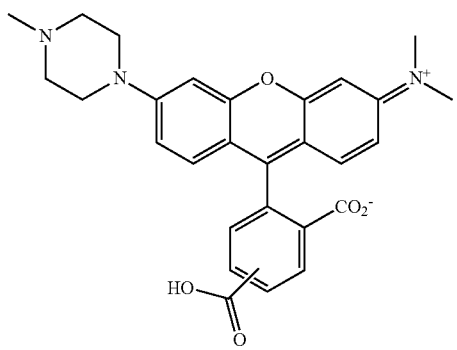

Dimethylamino-(4-methylpiperazin-1-yl)-rhodamine-(5',6')-)-carboxylic acid

To a mixture of 3'-(dimethylamino)-6'-iodo-3-oxo-3H-spiro[isobenzofuran-1,9'-xanthene]-5,6-carboxylic acid (29 mg, 57 μmol), N-methylpiperazine (11.3 mg, 113 μmol), copper(I) iodide (5.4 mg, 28 μmol), and sodium tert-butoxide (5.4 mg, 57) in a pressure tube fitted with magnetic stir bar, 2 mL of 2,2,2-trifluoroethanol was added. The vessel was sealed and heated with stirring at 120° C. by means of an oil bath overnight (~16 hours). After this time, the reaction was removed from the oil bath and cooled to room temperature before opening. About 2 ml water was added, and the resultant slurry centrifuged. The supernatant was subjected to preparative HPLC yielding a red solid upon evaporation of the appropriate fractions (12 mg, PBI-44%). MS (ESI) m/z calcd for $C_{28}H_{28}N_3O_5^+$ (M$^+$) 486.20. found 486. Ex/Em 545/572 nm.

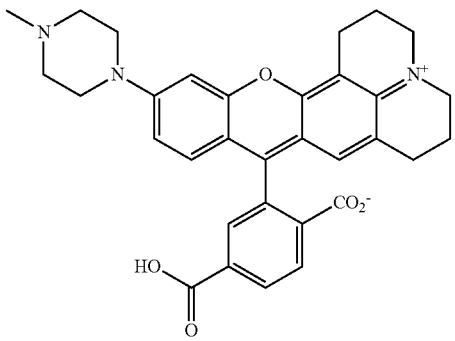

Hexahydroquinoiizino-(4-methylpiperazin-1-yl}-rhodamine-6'-carboxyic acid

To a mixture of 12-iodo-3'-oxo-1,2,3,5,6,7-hexahydro-3'H-spiro[chromeno[2,3-f]pyrido[3,2,1-ij]quinoline-9,1'-isobenzofuran]-6'-carboxylic acid (21 mg, 37 μmol), N-methylpiperazine (7.4 mg, 74 μmol), copper(I) iodide (3.5 mg, 19 μmol), and sodium tert-butoxide (3.6 mg, 37 μmol) in a pressure tube fitted with magnetic stir bar, 2 mL of 2,2,2-trifluoroethanol was added. The vessel was sealed and heated with stirring at 120° C. by means of an oil bath overnight (~16 hours). After this time, the reaction was removed from the oil bath and cooled to room temperature before opening. About 2 ml water was added, and the resultant slurry centrifuged. The supernatant was subjected to preparative HPLC yielding a red solid upon evaporation of the appropriate fractions (15 mg, 75%). MS (ESI) m/z calcd for $C_{32}H_{32}N_3O_5^+$ (M$^+$) 538.2. found 538.3. Ex/Em 559/586 nm.

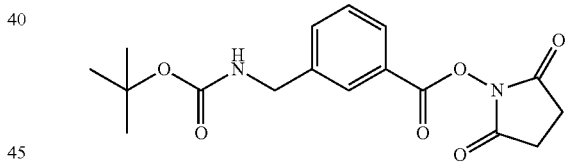

2,5-dioxopyrrolidin-1-yl 3-(((tert-butoxycarbonyl)amino)methyl)benzoate 3-(((tert-butoxycarbonyl)amino)methyl)benzoic acid (0.5 g, 1.99 mmol), O—(N-succinimidyl)-N,N,N',N'-tetramethyluronium tetrafluoroborate (718.8 mg, 2.39 mmol) and N,N-diisopropylethylamine (1.04 mL, 6.0 mmol) were dissolved in anhydrous DMF and stirred for 1 hour. The reaction mixture was diluted with ethyl acetate and washed with water and brine. The organic layer was dried over sodium sulfate and concentrated to give a white solid that was triturated with heptane and dried under hi-vacuum to give the product (492.0 mg) as a white solid. $^1$H-NMR (300 MHz, CDCl$_3$) δ 8.01 (m, 1H), 7.60 (m, 1H), 7.46 (m, 1H), 4.37 (d, 6.0 Hz, 1H), 2.89 (s, 4H), 1.44 (s, 9H). MS (ESI) m/z calcd for $C_{17}H_{19}N_2O_6$ (M−H$^+$) 347.1. found 347.2.

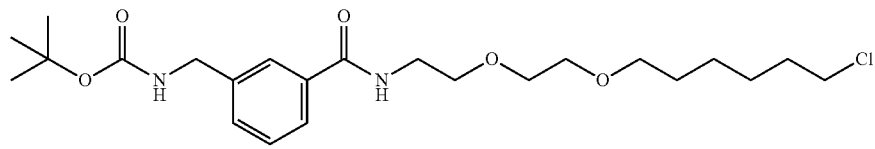 [SMILES: CC(C)(C)OC(=O)NCc1cccc(C(=O)NCCOCCOCCCCCCCl)c1]

Tert-butyl 3-((2-(2-((6-chlorohexyl)oxy)ethoxy)ethyl)carbamoyl)benzylcarbamate To a solution of 2,5-dioxopyrrolidin-1-yl 3-(((tert-butoxycarbonyl)amino)methyl)benzoate (50.0 mg, 1.14 mmol) in 10 mL DMF, 2-(2-((6-chlorohexyl)oxy)ethoxy)ethanamine-HCl (53.0 mg, 0.22 mmol) and N,N-diisopropylethylamine (0.14 mL, 0.79 mmol) was added. The reaction was capped and stirred overnight. Volatiles were removed under reduced pressure giving a yellow solid that was dissolved in DCM, absorbed on celite, dried and subjected to flash chromatography (EtOAc/Hep) purification giving the product (37.0 mg, 56.4%) as a white solid. $^1$H-NMR (300 MHz, CDCl$_3$) δ 7.61 (m, 1H), 7.63 (m, 1H), 7.40 (m, 1H), 4.34 (d, 5.7 Hz, 1H), 3.54 (m, H), 1.72 (m, 2H), 1.53 (s, 9H), 1.44 (s, 9H). MS (ESI) m/z calcd for $C_{23}H_{38}ClN_2O_5$ (M+H$^+$) 457.2. found 457.2.

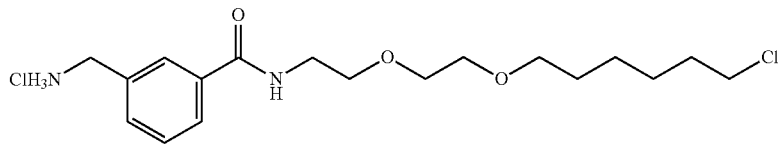

3-(aminomethyl)-N-(2-(2-((6-chlorohexyl)oxy)ethoxy)ethyl)benzamide-HCl

Tert-butyl 3-((2-(2-((6-chlorohexyl)oxy)ethoxy)ethyl)carbamoyl)benzylcarbamate was treated with HCl-dioxane (1 mL) and stirred overnight. Volatiles were removed under reduced pressure and the residue was triturated with Et$_2$O to give the product (49.9 mg, 0.14 mmol) as a white solid.

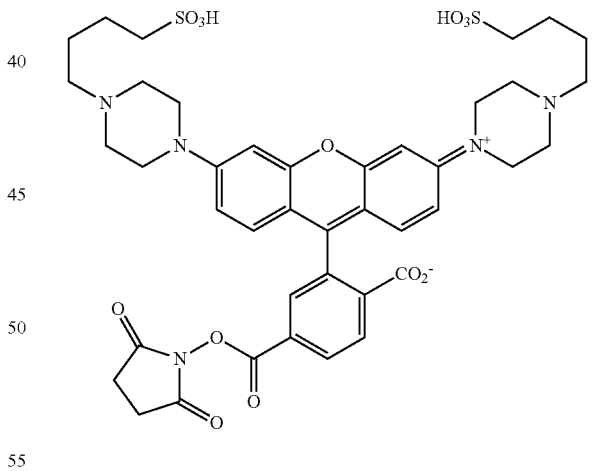

3',6'-bis(4-(4-sulfobutyl)piperazin-1-yl)rhodamine (5',6')succinimidyl ester PBI-4474 (25.0 mg, 0.03 mmol), O—(N-succinimidyl)-N,N,N',N'-tetramethyluronium tetrafluoroborate (19.2 mg, 0.06 mmol) and N,N-diisopropylethylamine (16.6 μL, 0.1 mmol) were stirred in DMF (2 mL) for 1 hr. The crude mixture was concentrated and subjected to RP-HPLC purification giving the product as a red solid.

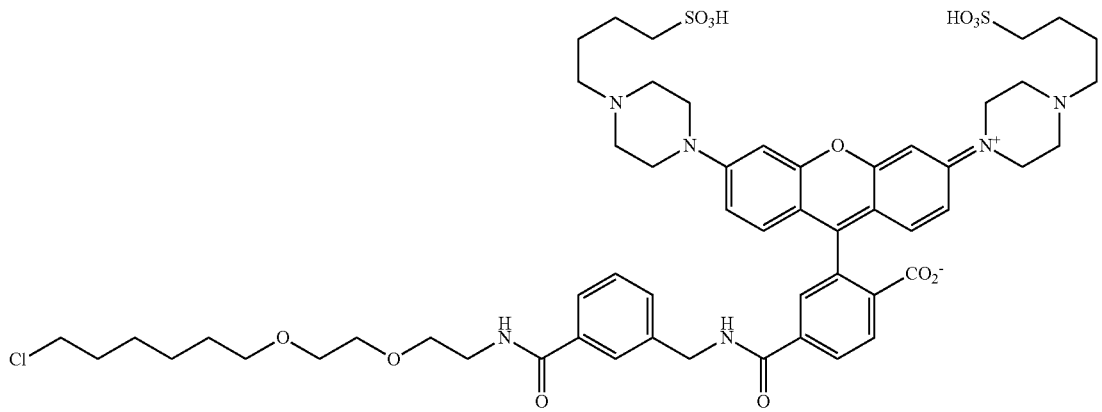

4-((3-((2-(2-((6-chlorohexyl)oxy)ethoxy)ethyl)carbamoyl)benzyl)-3',6'-bis(4-(4-sulfobutyl)piperazin-1-yl) rhodamine(5',6') carboxamide (PBI-4958)

3',6'-bis(4-(4-sulfobutyl)piperazin-1-yl) rhodamine(5',6') succinimidyl ester (10.0 mg, 0.01 mmol), 3-(aminomethyl)-N-(2-(2-((6-chlorohexyl)oxy)ethoxy)ethyl)benzamide-HCl, 0.25 M in DMF (0.05 mL, 0.01 mmol) and N,N-diisopropylethylamine were stirred in 1 mL DMF for 1 hr. The crude mixture was diluted with water and subjected to RP-HPLC preparative chromatography to give the product as a red solid (1.3 mg, 10.5%) after lyophilization. MS (ESI) m/z calcd for $C_{55}H_{72}ClN_6O_{13}S_2$ (M+H$^+$) 1123.4. found 1123.5.

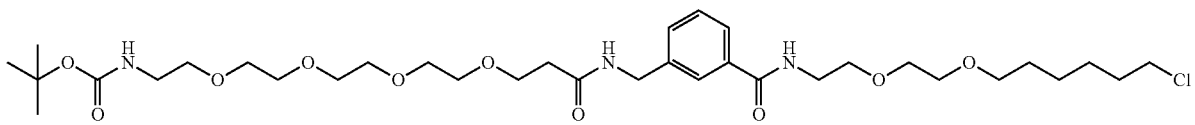 [SMILES: CC(C)(C)OC(=O)NCCOCCOCCOCCOCCC(=O)NCc1cccc(C(=O)NCCOCCOCCCCCCCl)c1]

Tert-butyl(1-(3-((2-(2-((6-chlorohexyl)oxy)ethoxy)ethyl)carbamoyl)phenyl)-3-oxo-6,9,12,15-tetraoxa 2-azaheptadecan-17-yl)carbamate To a solution of 2,2-dimethyl-4-oxo-3,8,11,14,17-pentaoxa-5-azaicosan-20-oic acid (20.0 mg, 0.05 mmol) in 1 mL DMF, O—(N-succinimidyl)-N,N,N',N'-tetramethyluronium tetrafluoroborate (19.8 mg, 0.07 mmol) and N,N-diisopropylethylamine (0.03 mL, 0.16 mL) was added. The mixture was stirred for 0.5 hr. A 0.5 mL aliquot was treated with 0.25 M solution of 3-(aminomethyl)-N-(2-(2-((6-chlorohexyl)oxy)ethoxy)ethyl)benzamide (0.1 mL, 0.03 mL). The mixture was stirred for 1.5 hrs before being concentrated to give the product as a yellow oil.

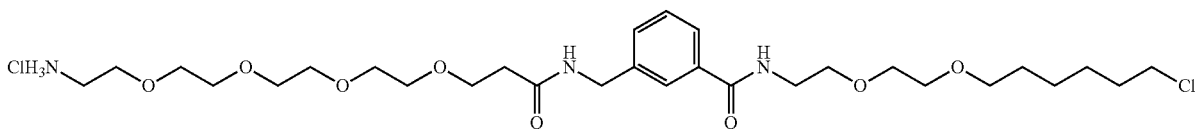

1-amino-N-(3-((2-(2-((6-chlorohexyl)oxy)ethoxy)ethyl)carbamoyl)benzyl)-3,6,9,12-tetraoxapentadecan-15-amide-HCl Tert-butyl(1-(3-((2-(2-((6-chlorohexyl)oxy)ethoxy)ethyl)carbamoyl)phenyl)-3-oxo-6,9,12,15-tetraoxa-2-azaheptadecan-17-yl)carbamate (20.0 mg, 0.3 mmol) was treated with 4.0 M HCl-dioxane (0.8 mL) with stirring overnight. The mixture was absorbed on celite, dried and subjected to flash chromatography to give the product (8.0 mg, 98.9%) as a colorless oil.

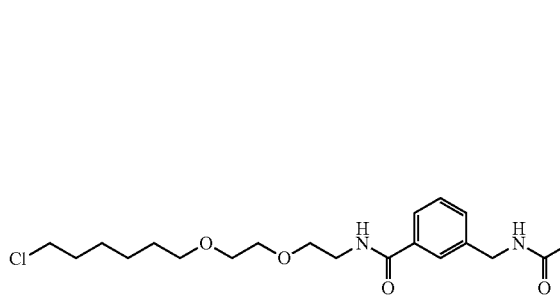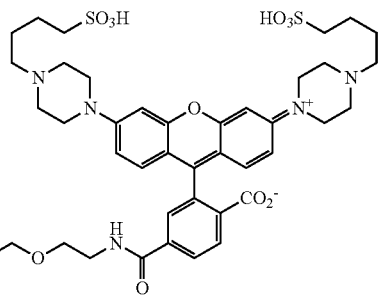

4-((1-(3-((2-(2-((6-chlorohexyl)oxy)ethoxy)ethyl)carbamoyl)phenyl)-3-oxo-6,9,12,15-tetraoxa-2-aza-heptadecan-1'7-yl)-3',6'-bis(4-(4-sulfobutyl)piperazin-1-yl) rhodamine(5',6')carboxamide (PBI-4994)

3',6'-bis(4-(4-sulfobutyl)piperazin-1-yl) rhodamine(5',6') succinimidyl ester (5.0 mg, 0.005 mmol), 3-(aminomethyl)-N-(2-(2-(6-chlorohexyl)oxy)ethoxy)ethyl)benzamide-HCl 0.025 M in DMF (0.27 mL, 0.007 mmol) and 3 drops of N,N-diisopropylethylamine were stirred in 1 mL DMF for 1 hr. The crude mixture was diluted with water and subjected to RP-HPLC preparative chromatography to give the product as a red solid (1.1 mg, 14.2%) after lyophilization. MS (ESI) m/z calcd for $C_{66}H_{93}ClN_7O_{18}S_2$ (M+H$^+$) 1370.6. found 1370.6.

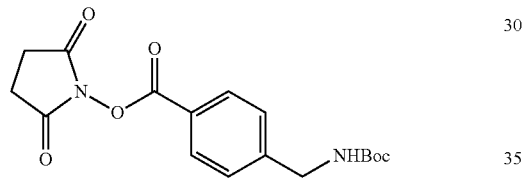

2,5-dioxopyrrolidin-1-yl 4-(((tert-butoxycarbonyl)amino)methyl)benzoate

To a solution of 4-(((tert-butoxycarbonyl)amino)methyl)benzoic acid(1.0 g, 3.98 mmol) and O—(N-succinimidyl)-N,N,N',N'-tetramethyluronium tetrafluoroborate (1.44 g, 4.78 mmol) in 20 ml DMF, N,N-diisopropylethylamine (1.0 mL, 5.97 mmol) was added. The mixture was stirred for 2 hrs, concentrated under reduced pressure giving a red solid that was dissolved in EtOAc and washed with 30% citric acid solution. The organic layer was retained, dried over Na$_2$SO$_4$ and concentrated to give a yellow sticky solid.

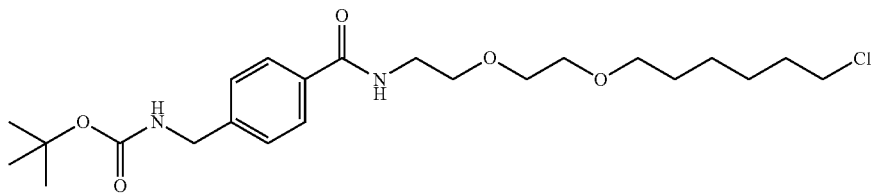 [SMILES: CC(C)(C)OC(=O)NCc1ccc(C(=O)NCCOCCOCCCCCCCl)cc1]

Tert-butyl 4-((2-(2-((6-chlorohexyl)oxy)ethoxy)ethyl)carbamoyl)benzylcarbamate

To a solution of 2,5-dioxopyrrolidin-1-yl 4-(((tert-butoxycarbonyl)amino)methyl)benzoate (50.0 mg, 0.14 mmol) in 10 mL DMF, 2-(2-((6-chlorohexyl)oxy)ethoxy)ethanamine-HCl (42.4 mg, 0.17 mmol) and N,N-diisopropylethylamine (0.13 mL, 0.72 mmol) was added. The reaction was capped and stirred overnight. Volatiles were removed under reduced pressure giving a yellow solid that was dissolved in EtOAc, washed with water, dried over Na$_2$SO$_4$ and concentrated. The residue was dissolved in DCM, absorbed on celite, dried and subjected to flash chromatography (EtOAc/Hep) purification giving the product (32.0 mg, 48.8%) as a white solid. $^1$H-NMR (300 MHz, CDCl$_3$) δ 7.73 (d, 8.4 Hz, 2H), 7.32 (d, 8.4 Hz, 2H), 4.34 (d, 6.6, 2H), 3.65-3.42 (m, 8H), 2.75 (m, 4H), 1.5 (s, 9H) 1.2 (m, 10H). MS (ESI) m/z calcd for $C_{23}H_{38}ClN_2O_5$ (M+H$^+$) 457.2. found 457.7.

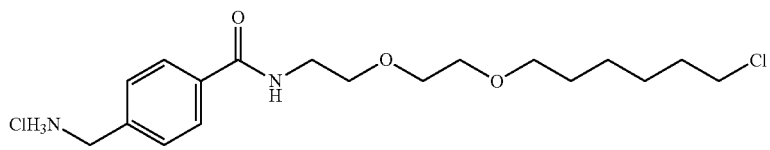

4-(aminomethyl)-N-(2-(2-(((6-chlorohexyl)oxy)ethoxy)ethyl)benzamide-HCl

Tert-butyl 4-((2-(2-(((6-chlorohexyl)oxy)ethoxy)ethyl)carbamoyl)benzylcarbamate (32.0 mg, 0.07 mmol) was treated with HCl-dioxane (1 mL) and stirred overnight. Volatiles were removed under reduced pressure, and the residue triturated with $Et_2O$ to give the product (27.0 mg, 98.0%) as a white solid.

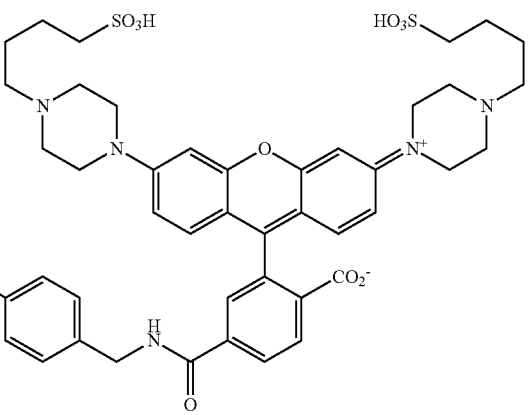

4-((4-((2-(2-(((6-chlorohexyl)oxy)ethoxy)ethyl)carbamoyl)benzyl))-3',6'-bis(4-(4-sulfobutyl)piperazin-1-yl) rhodamine(5',6') carboxamide (PBI-4959)

3',6'-bis(4-(4-sulfobutyl)piperazin-1-yl) rhodamine(5',6') succinimidyl ester (10.0 mg, 0.01 mmol), 3-(aminomethyl)-N-(2-(2-(((6-chlorohexyl)oxy)ethoxy)ethyl)benzamide-HCl 0.25 M in DMF (0.05 mL, 0.01 mmol) and N,N-diisopropylethylamine were stirred in 1 mL DMF for 1 hr. The crude mixture was diluted with water and subjected to RP-HPLC preparative chromatography to give the product as a red solid (1.1 mg, 8.9%) after lyophilization. MS (ESI) m/z calcd for $C_{55}H_{72}ClN_6O_{13}S_2$ (M+H$^+$) 1123.5. found 1123.4. Ex/Em 532/564 nm.

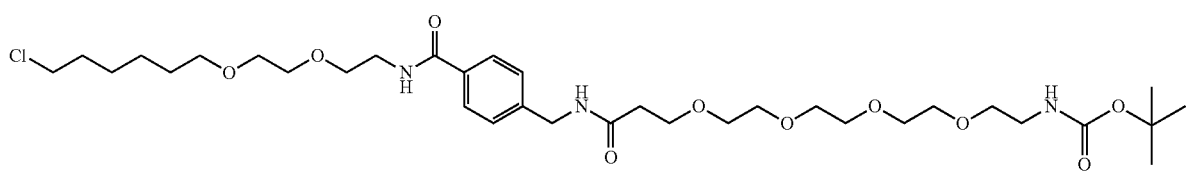 [SMILES: CC(C)(C)OC(=O)NCCOCCOCCOCCOCCC(=O)NCc1ccc(C(=O)NCCOCCOCCCCCCCl)cc1]

Tert-butyl(1-(4-((2-(2-(((6-chlorohexyl)oxy)ethoxy)ethyl)carbamoyl)phenyl)-3-oxo-6,9,12,15-tetraoxa-2-azaheptadecan-17-yl)carbamate To a solution of 2,2-dimethyl-4-oxo-3,8,11,14,17-pentaoxa-5-azaicosan-20-oic acid (20.0 mg, 0.05 mmol) in 1 mL DMF, O—(N-succinimidyl)-N,N,N',N'-tetramethyluronium tetrafluoroborate (19.8 mg, 0.07 mmol) and N,N-diisopropylethylamine (0.03 mL, 0.16 mL) was added. The mixture was stirred for 0.5 hr. A 0.5 mL aliquot was treated with 0.25 M solution of 4-(aminomethyl)-N-(2-(2-(((6-chlorohexyl)oxy)ethoxy)ethyl)benzamide-HCl (0.1 mL, 0.03 mL). The mixture was stirred overnight before being concentrated to give the product as a yellow oil.

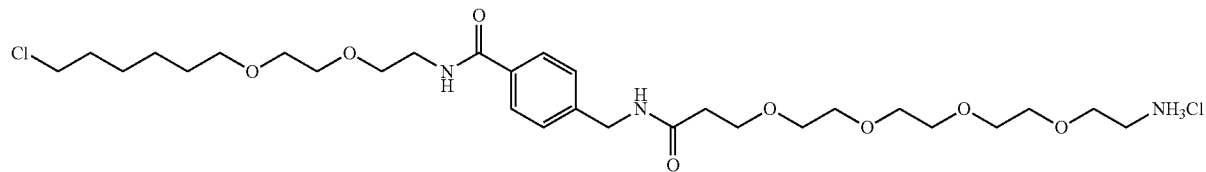

1-amino-N-(4-((2-(2-((6-chlorohexyl)oxy)ethoxy)ethyl)carbamoyl)benzyl)-3,6,9,12-tetraoxapentadecan-15-amide-HCl Tert-butyl(1-(4-((2-(2-((6-chlorohexyl)oxy)ethoxy)ethyl)carbamoyl)phenyl)-3-oxo-6,9,12,15-tetraoxa-2-azaheptadecan-17-yl)carbamate (20.0 mg, 0.3 mmol) was treated with 4.0 M HCl-dioxane (0.8 mL) with stirring overnight. The mixture was absorbed on celite, dried and subjected to flash chromatography to give the product (17.0 mg, 93.5%) as a colorless oil.

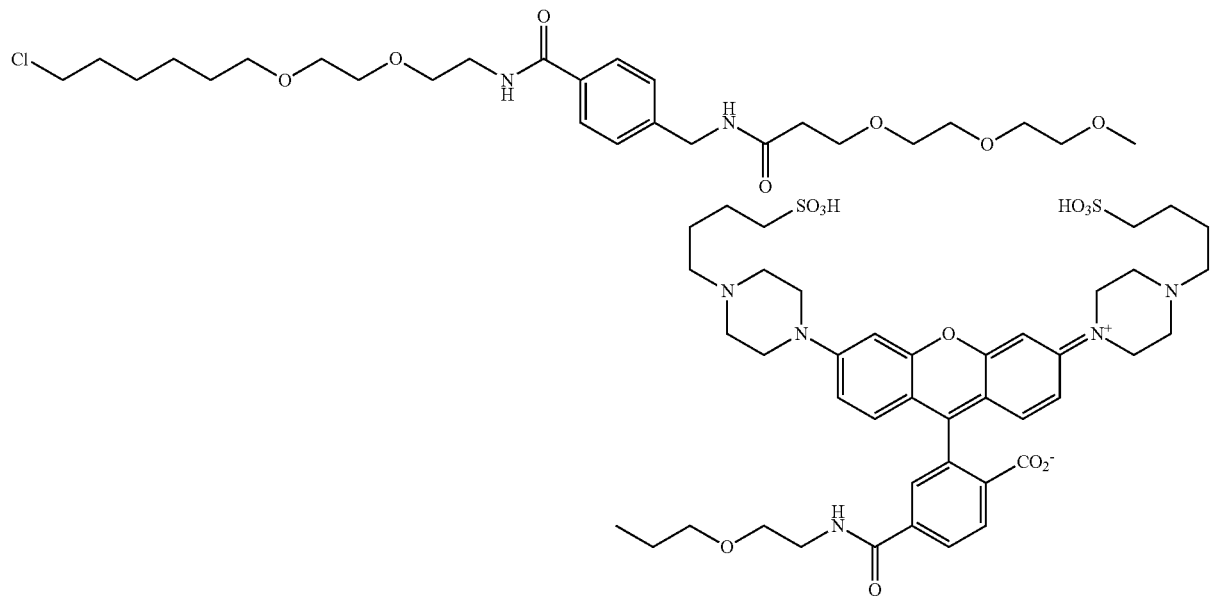

4-((1-(4-((2-(2-((6-chlorohexyl)oxy)ethoxy)ethyl)carbamoyl)phenyl)-3-oxo-6,9,12,15-tetraoxa-2-azaheptadecan-17-yl)) 3',6'-bis(4-(4-sulfobutyl)piperazin-1-yl) rhodamine(5',6')carboxamide (PBI-4995)

3',6'-bis(4-(4-sulfobutyl)piperazin-1-yl) rhodamine(5',6') succinimidyl ester (10.0 mg, 0.011 mmol), 3-(aminomethyl)-N-(2-(2-(6-chlorohexyl)oxy)ethoxy)ethyl)benzamide-HCl 0.025 M in DMF (0.54 mL, 0.0136 mmol) and 3 drops of N,N-diisopropylethylamine were stirred in 1 mL DMF for 1 hr. The crude mixture was diluted with water and subjected to RP-HPLC preparative chromatography to give the product as a red solid (4.9 mg, 31.5%) after lyophilization. MS (ESI) m/z calcd for $C_{66}H_{93}ClN_7O_{18}S_2$ (M+H$^+$) 1370.6. found 1371.0.

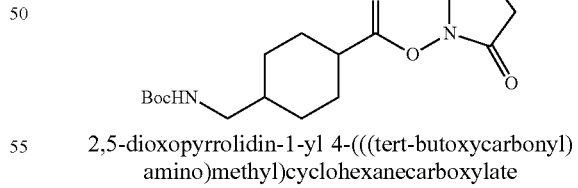

2,5-dioxopyrrolidin-1-yl 4-(((tert-butoxycarbonyl)amino)methyl)cyclohexanecarboxylate To a solution of 4-(((tert-butoxycarbonyl)amino)methyl)cyclohexanecarboxylic acid (2.0 g, 7.77 mmol) and O—(N-succinimidyl)-N,N,N',N'-tetramethyluronium tetrafluoroborate (2.81 g, 9.33 mmol) in 40 ml DMF, N,N-diisopropylethylamine (2.71 mL, 15.54 mmol) was added. The mixture was stirred for 3 hrs, concentrated under reduced pressure giving a red solid that was dissolved in EtOAc and washed with 30% citric acid solution. The organic layer was retained, dried over $Na_2SO_4$ and concentrated to give a yellowish sticky solid (0.69 g, 24.9%).

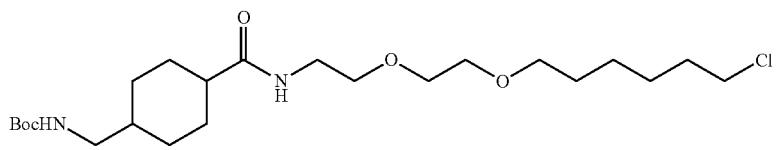 [SMILES: CC(C)(C)OC(=O)NCC1CCC(C(=O)NCCOCCOCCCCCCCl)CC1]

Tert-butyl((4-((2-(2-((6-chlorohexyl)oxy)ethoxy)ethyl)carbamoyl)cyclohexyl)methyl)carbamate To a solution of 2,5-dioxopyrrolidin-1-yl 4-(((tert-butoxycarbonyl)amino)methyl)cyclohexanecarboxylate (81.7 mg, 0.14 mmol) in 5 mL DMF, 2-(2-((6-chlorohexyl)oxy)ethoxy)ethanamine-HCl (50.0 mg, 0.19 mmol) and N,N-diisopropylethylamine (0.10 mL, 0.57 mmol) was added. The reaction was capped and stirred overnight. Volatiles were removed under reduced pressure giving a yellow residue that was dissolved in DCM, absorbed on celite, dried and subjected to flash chromatography (MeOH/DCM) purification giving the product (35.0 mg, 39.3%) as a white solid.

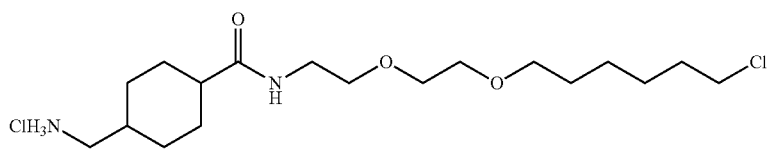

4-(aminomethyl)-N-(2-(2-((6-chlorohexyl)oxy)ethoxy)ethyl)cyclohexanecarboxamide-HCl Tert-butyl((4-((2-(2-((6-chlorohexyl)oxy)ethoxy)ethyl)carbamoyl)cyclohexyl)methyl)carbamate (35.0 mg, 0.076 mmol) was treated with HCl-dioxane (1 mL) and stirred overnight. Volatiles were removed under reduced pressure, and the residue triturated with $Et_2O$ to give the product (23.0 mg, 76.2%) as a white solid.

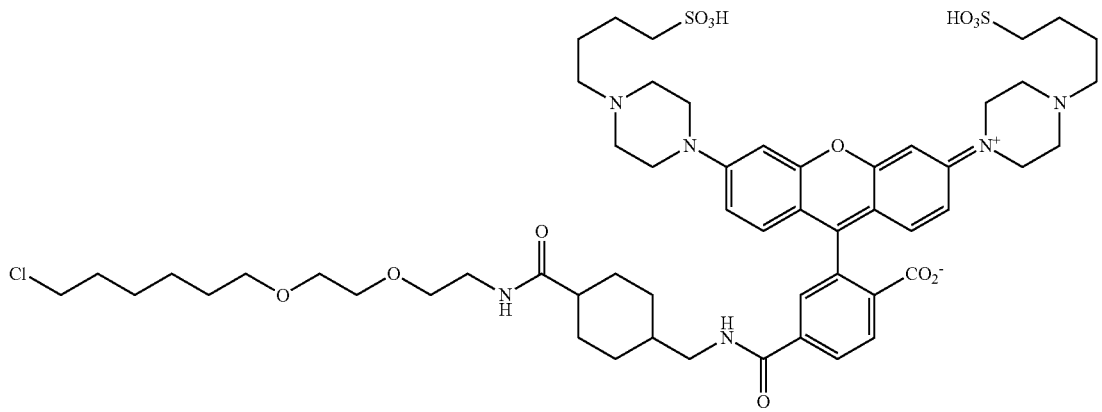

4-(((4-((2-(2-((6-chlorohexyl)oxy)ethoxy)ethyl)carbamoyl)cyclohexyl)methyl)) 3',6'-bis(4-(4-sulfobutyl)piperazin-1-yl) rhodamine(5',6') carboxamide (PBI-5004)

3',6'-bis(4-(4-sulfobutyl)piperazin-1-yl) rhodamine(5',6') succinimidyl ester (10.0 mg, 0.01 mmol), 4-(aminomethyl)-N-(2-(2-((6-chlorohexyl)oxy)ethoxy)ethyl)cyclohexanecarboxamide-HCl (0.25 M) in DMF (0.05 mL, 0.01 mmol) and N,N-diisopropylethylamine were stirred in 1 mL DMF for 1 hr. The crude mixture was diluted with water and subjected to RP-HPLC preparative chromatography to give the product as a red solid (4.3 mg, 33.6%) after lyophilization. MS (ESI) m/z calcd for $C_{55}H_{77}ClN_6O_{13}S_2$ (M+) 1128.5. found 1128.0. Ex/Em 532/560 nm.

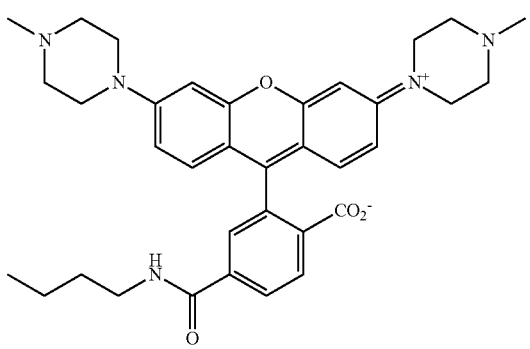

4-(butylcarbamoyl)-2-(3-(4-methylpiperazin-1-ium-1-ylidene)-6-(4-methylpiperazin-1-yl)-3H-xanthen-9-yl)benzoate (PBI-5183)

To 3',6'-bis(4-methylpiperazin-1-yl)-rhodamine(5,6)-carboxylic acid (19.3 mg, 0.030 mmol) in DMF (3 ml), O-(Nsuccinimidyl)-N,N,N',N'-tetramethyluronium tetrafluoroborate (15.4 mg, 0.049 mmol) and diisopropylethylamine (16.5 µL, 0.268 mmol) was added. The reaction mix was stirred for 3 hrs before adding butylamine (29.0 µLl, 0.017 mmol). The reaction was stirred overnight, and the volatiles removed under reduced pressure giving a dark solid that was dissolved in 1:1:0.01 ACN/water/TFA and subjected to RP-HPLC chromatography to give the product as a red solid. MS (ESI) m/z calcd for $C_{35}H_{42}N_5O_4$ (M+H+) 596.3. found 596.4.

Example 9

Toxicity of HaloTag pH Sensors in U2-OS Cells

Figure 21:
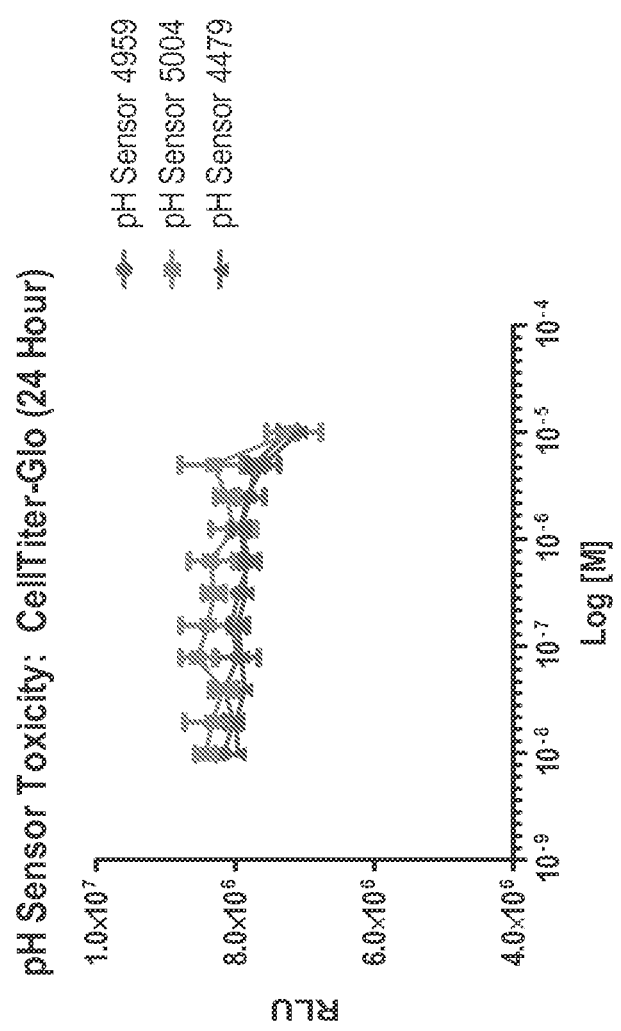
FIG. 21 shows the non-toxicity of the pH sensors PBI-4479, PBI-4959 and PBI-5004 in cells.

To demonstrate the non-toxicity of HaloTag pH sensors, U2-OS cells were exposed to PBI-4959, PBI-5004 and PBI-4479. U2-OS cells were plated at 10,000 cells/well into wells of 96-well plates and incubated overnight. The next day, 0-10 uM (serially diluted 1:2) PBI-4959, PBI-5004 or PBI-4479 was added to the cells and again incubated overnight. After incubation, the media containing the HaloTag® pH sensors was removed, and 100 ul of fresh media (McCoy's 5A+10% FBS) was added. Cell viability was determined using the CELLTITER Glo Cell Viability Assay according to the manufacturer's protocol (Promega Corporation). Luminescence was read on a GloMAX®-Multi luminometer. FIG. 21 demonstrates the non-toxicity of the pH sensors to wild-type U2-OS cells.

Example 10 pH Sensor Specificity

Figure 22:
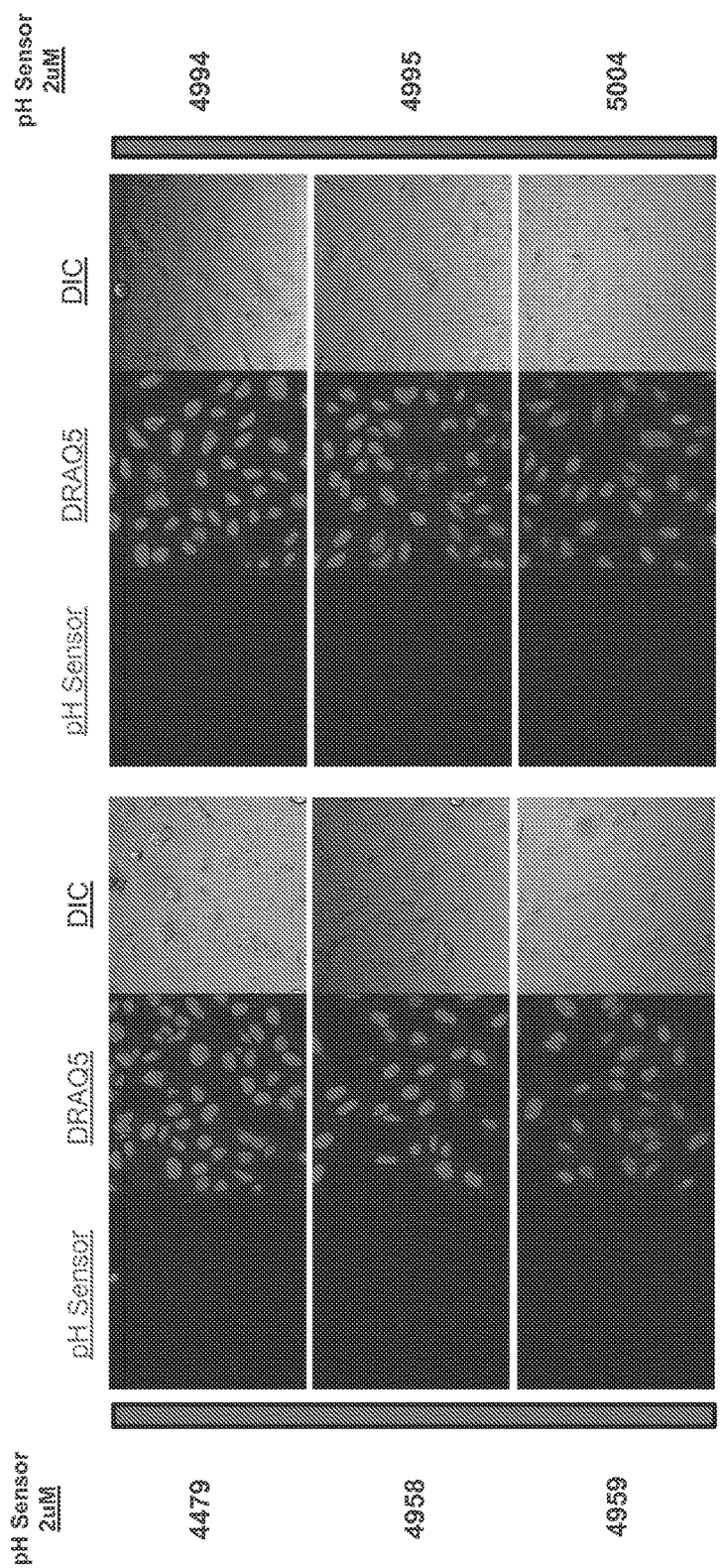
FIG. 22 shows the degree of non-specific binding of the pH sensors PBI-4479, PBI-4958, PBI-4959, PBI-4994, PBI-4995, and PBI-5004 in wild-type U2-OS cells.
Figure 23:
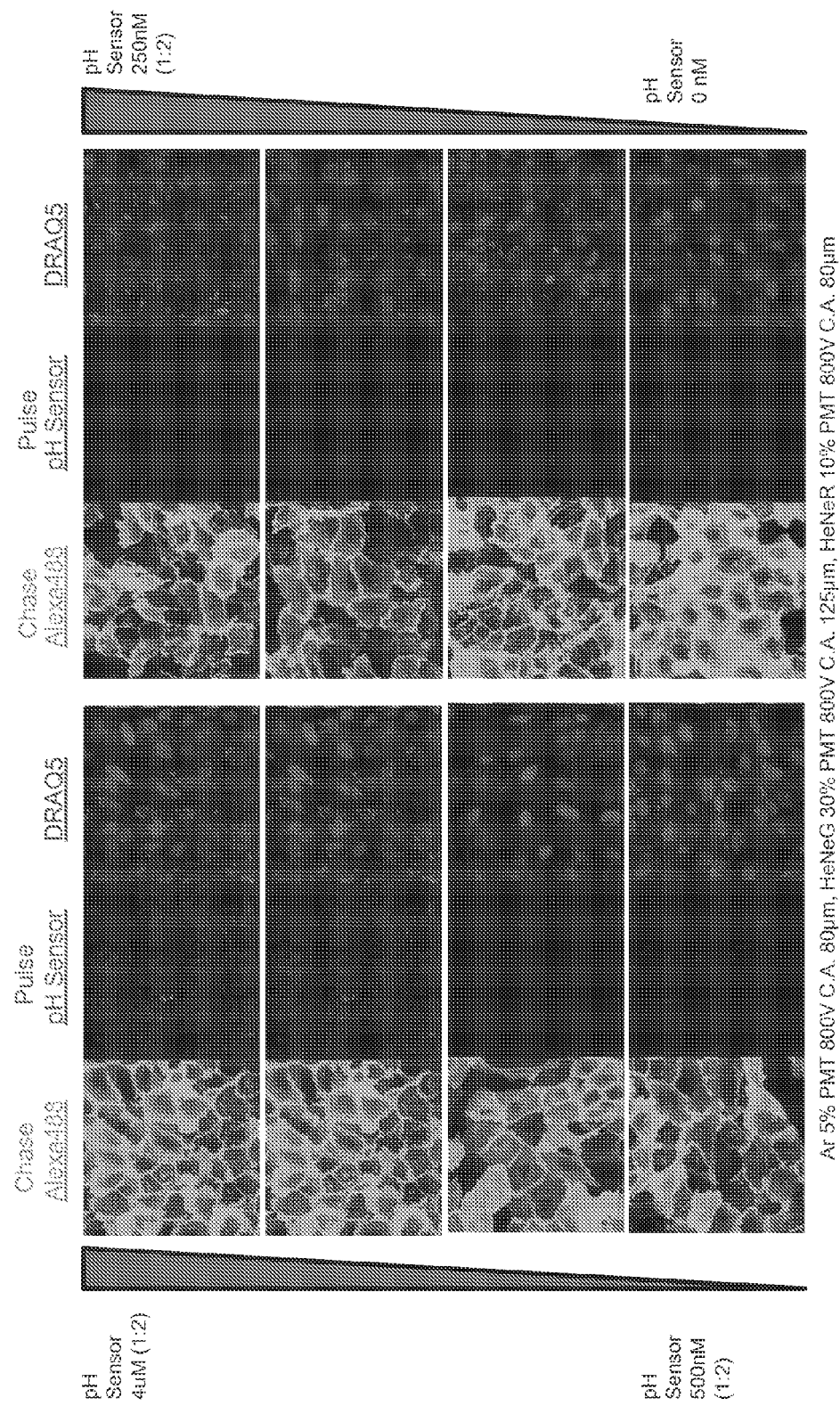
FIG. 23 shows the degree of labeling and background of pH sensor PBI-4479 in the unstimulated U2-OS HaloTag-EDG1 stable cell line.
Figure 24:
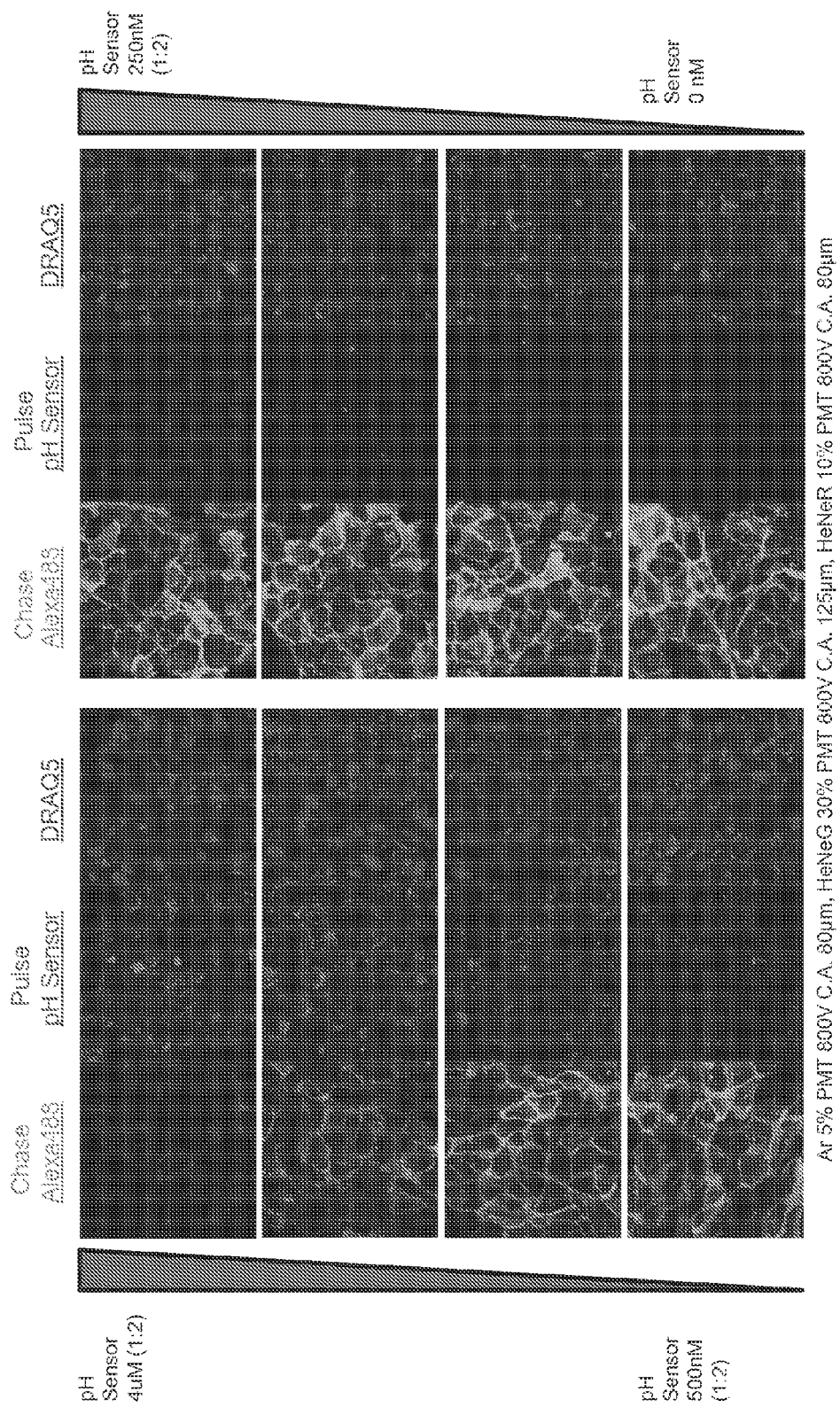
FIG. 24 shows the degree of labeling and background of pH sensor PBI-4958 in the unstimulated U2-OS HaloTag-EDG1 stable cell line.
Figure 25:
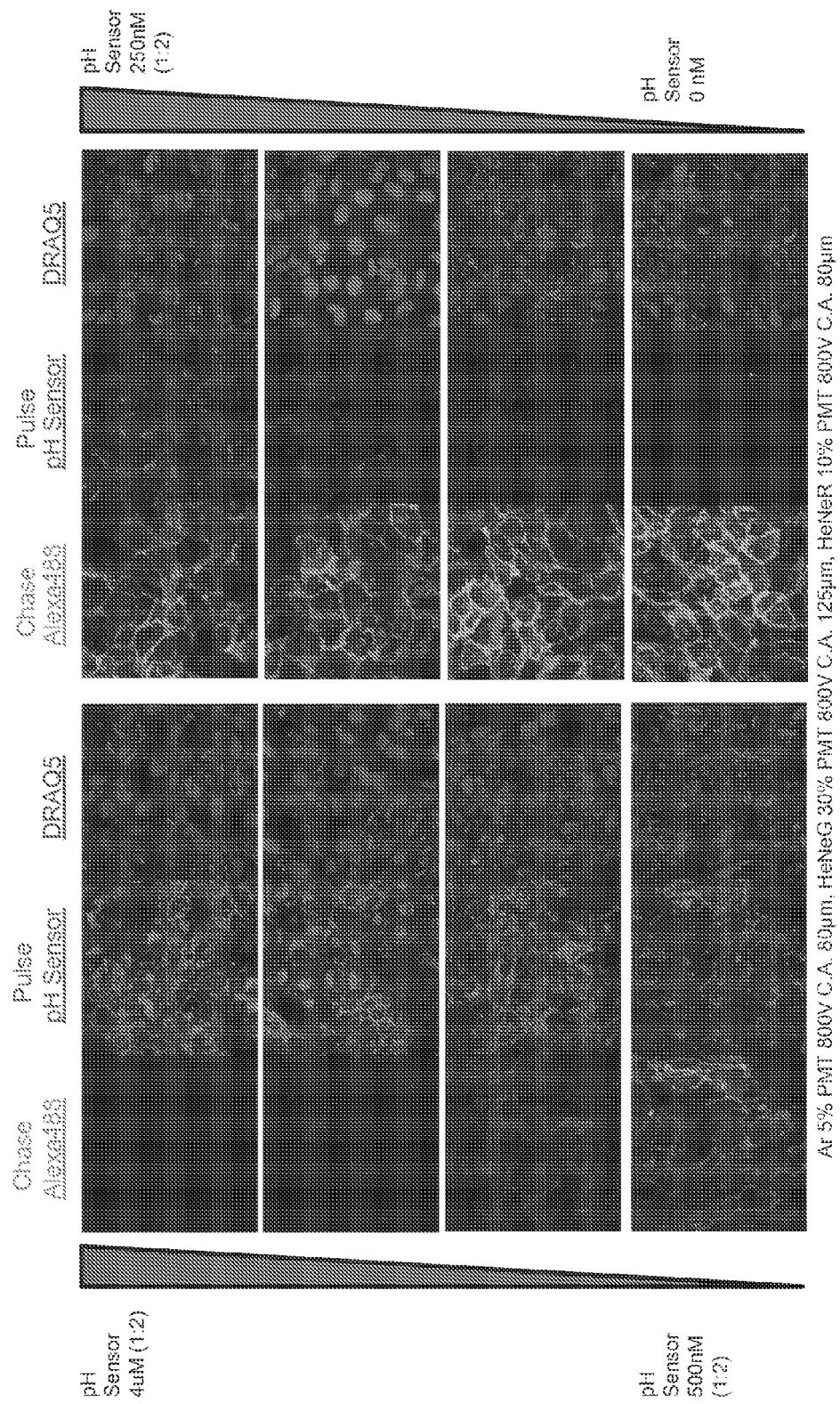
FIG. 25 shows the degree of labeling and background of pH sensor PBI-4959 in the unstimulated U2-OS HaloTag-EDG1 stable cell line.
Figure 26:
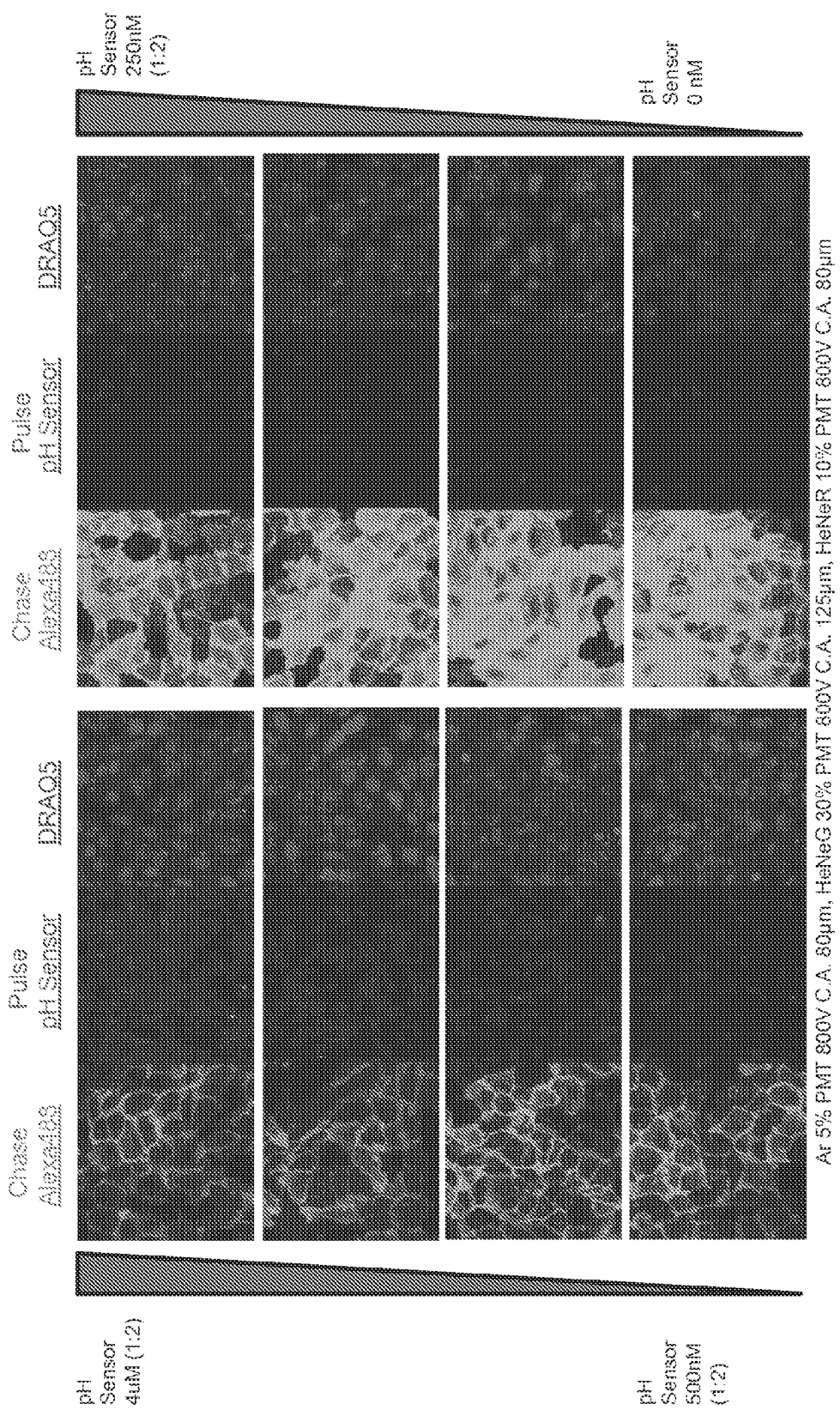
FIG. 26 shows the degree of labeling and background of pH sensor PBI-4994 in the unstimulated U2-OS HaloTag-EDG1 stable cell line.
Figure 27:
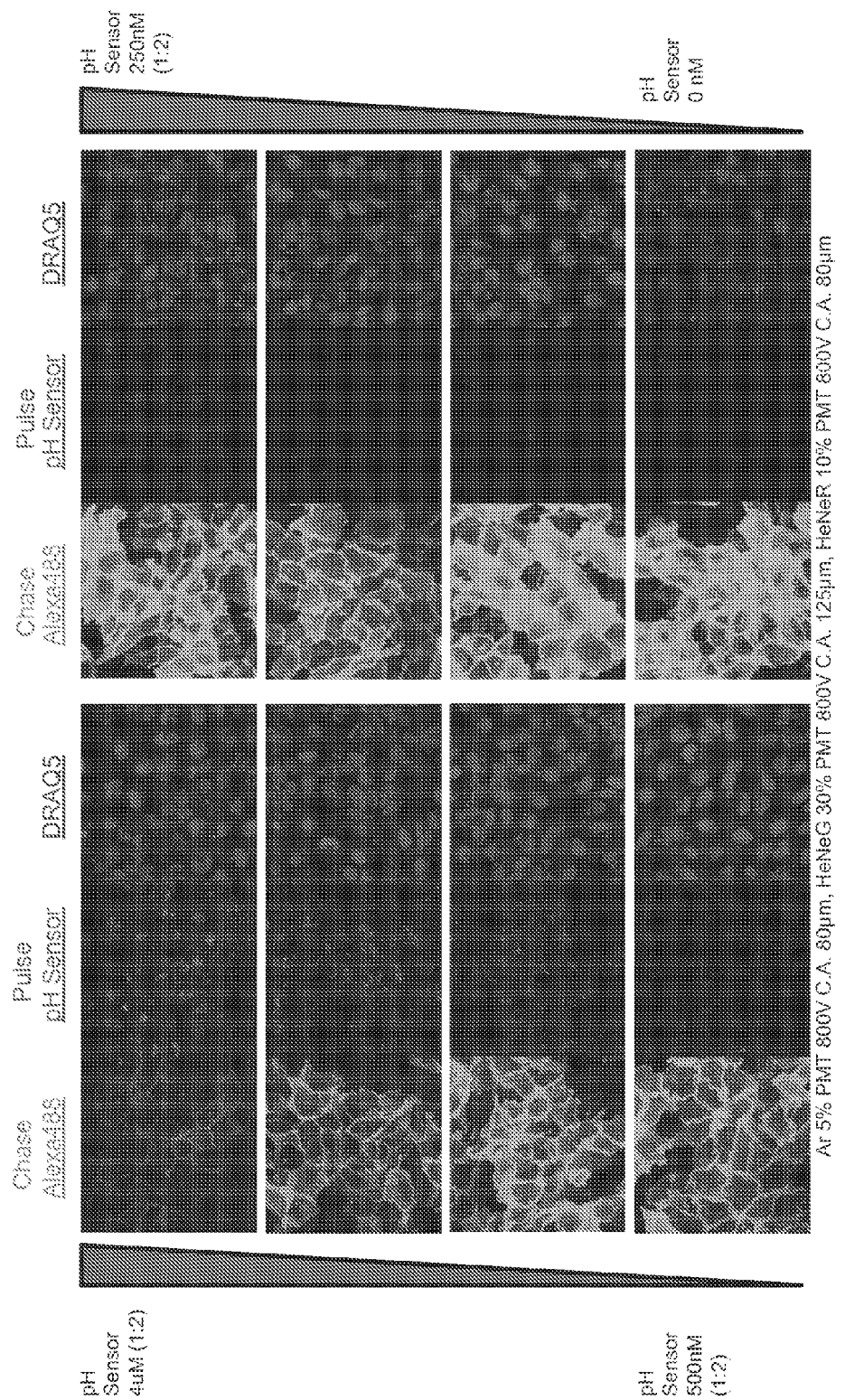
FIG. 27 shows the degree of labeling and background of pH sensor PBI-4995 in the unstimulated U2-OS HaloTag-EDG1 stable cell line.
Figure 28:
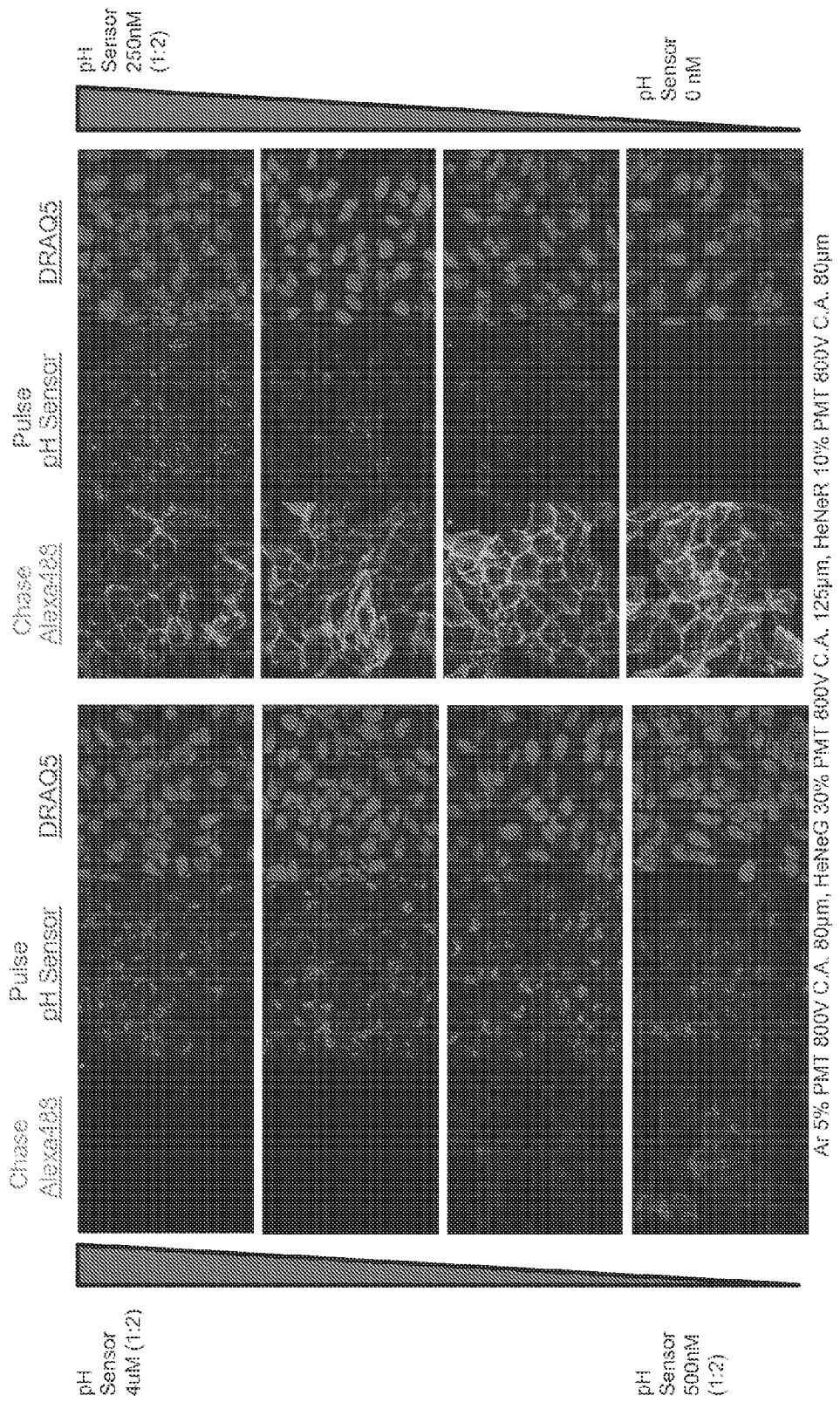
FIG. 28 shows the degree of labeling and background of pH sensor PBI-5004 in the unstimulated U2-OS HaloTag-EDG1 stable cell line.
Figure 29:
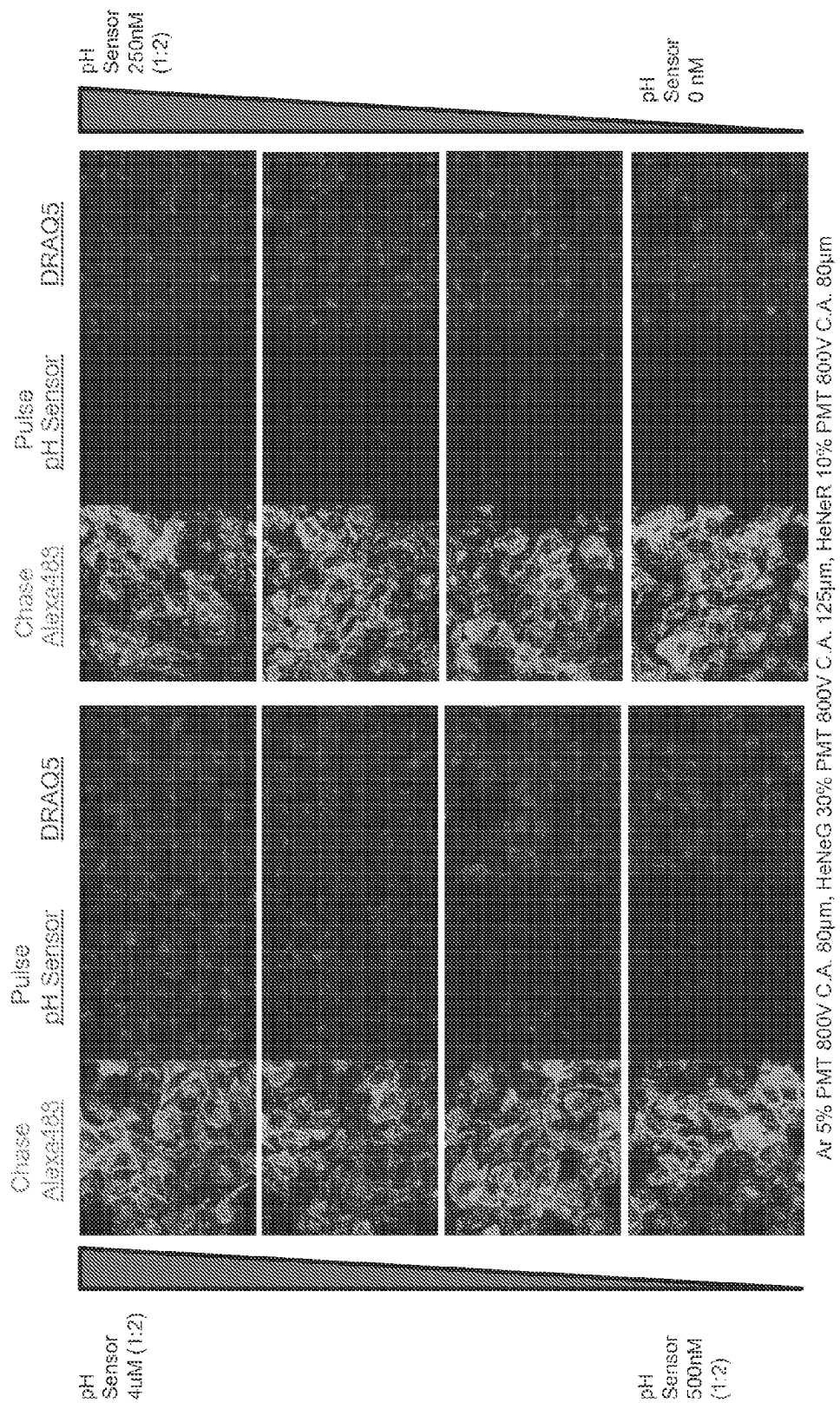
FIG. 29 shows the brightness of pH sensor PBI-4479 after agonist stimulation in U2-OS HaloTag-EDG1 stable cell line.
Figure 30:
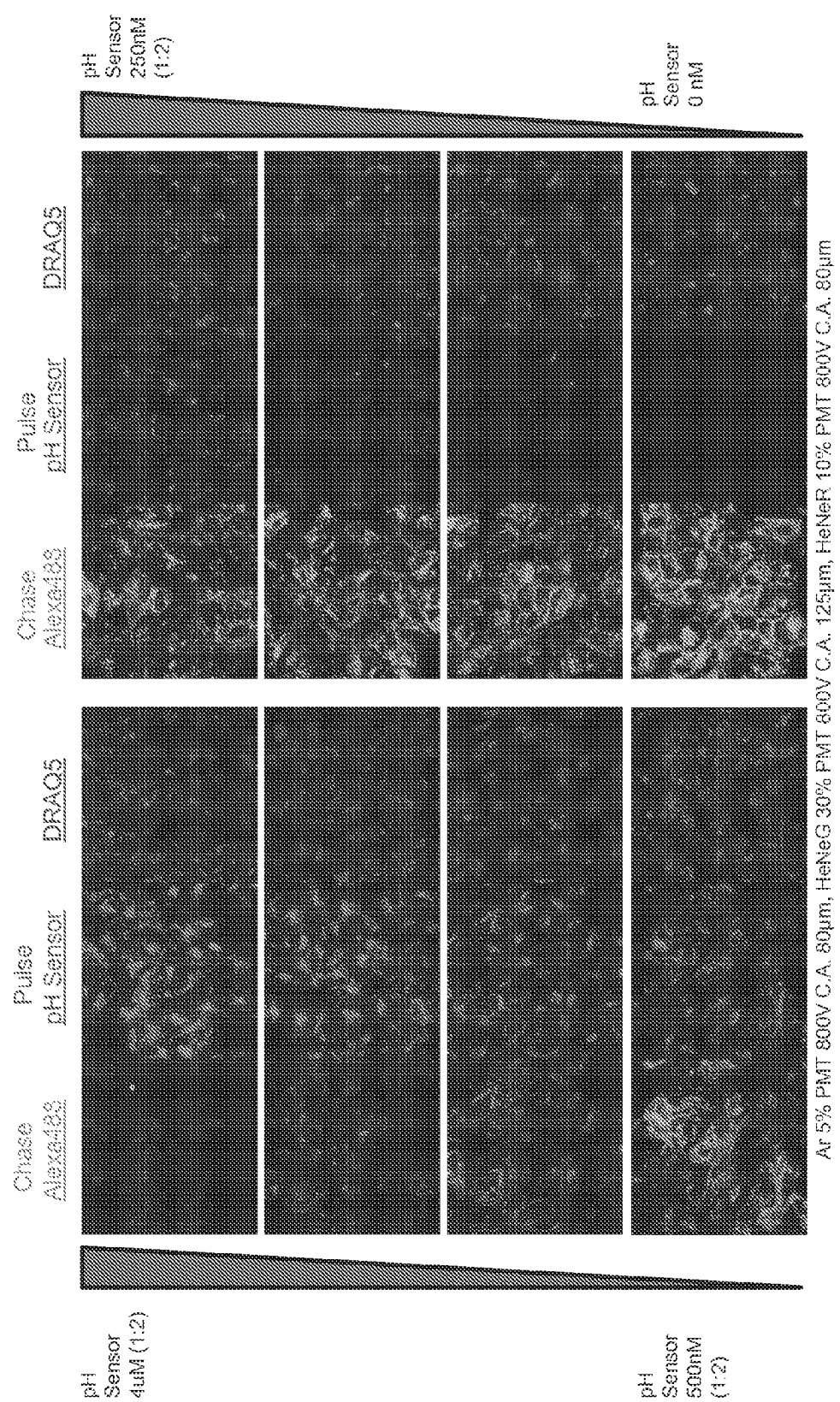
FIG. 30 shows the brightness of pH sensor PBI-4958 after agonist stimulation in U2-OS HaloTag-EDG1 stable cell line.
Figure 31:
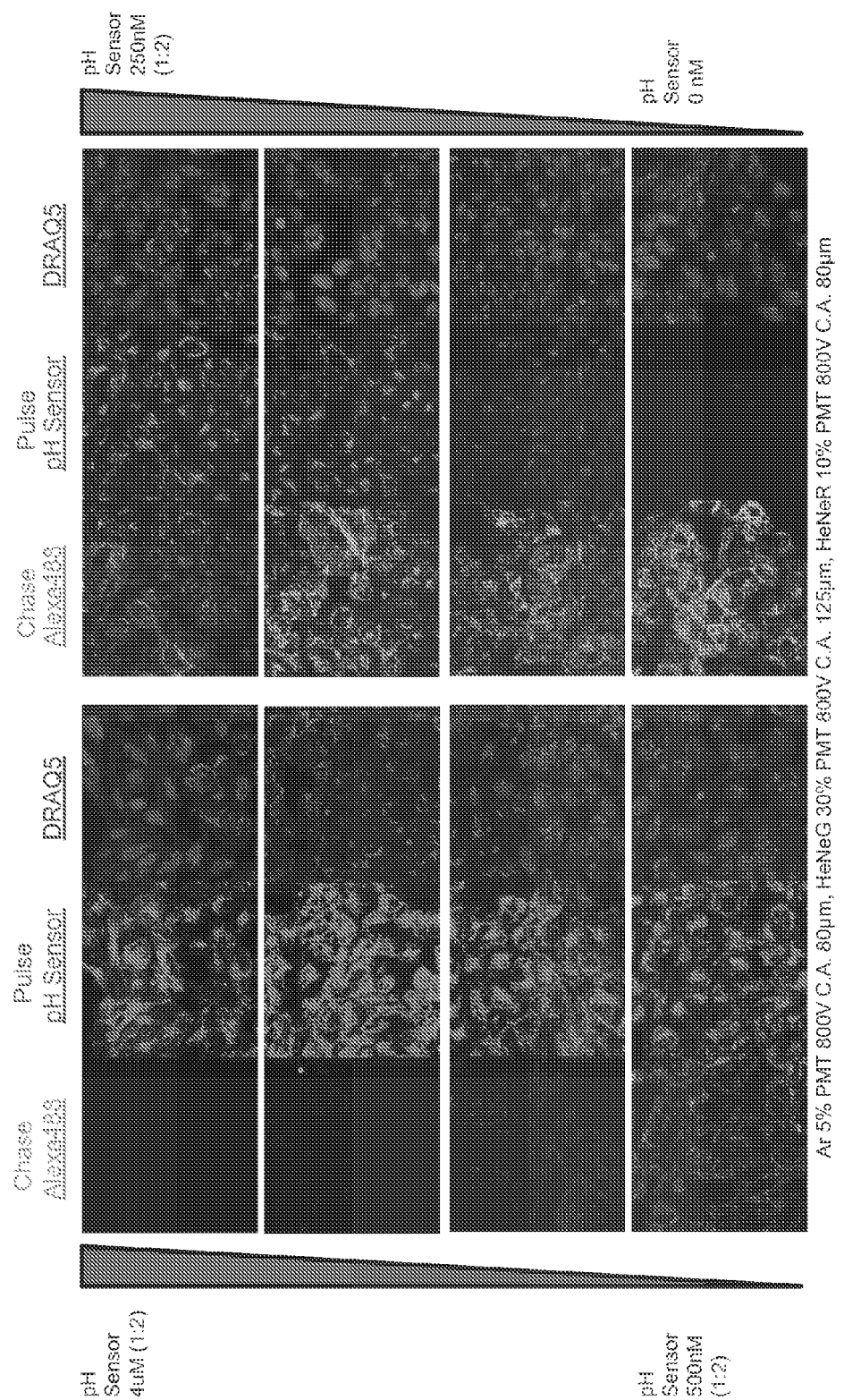
FIG. 31 shows the brightness of pH sensor PBI-4959 after agonist stimulation in U2-OS HaloTag-EDG1 stable cell line.
Figure 32:
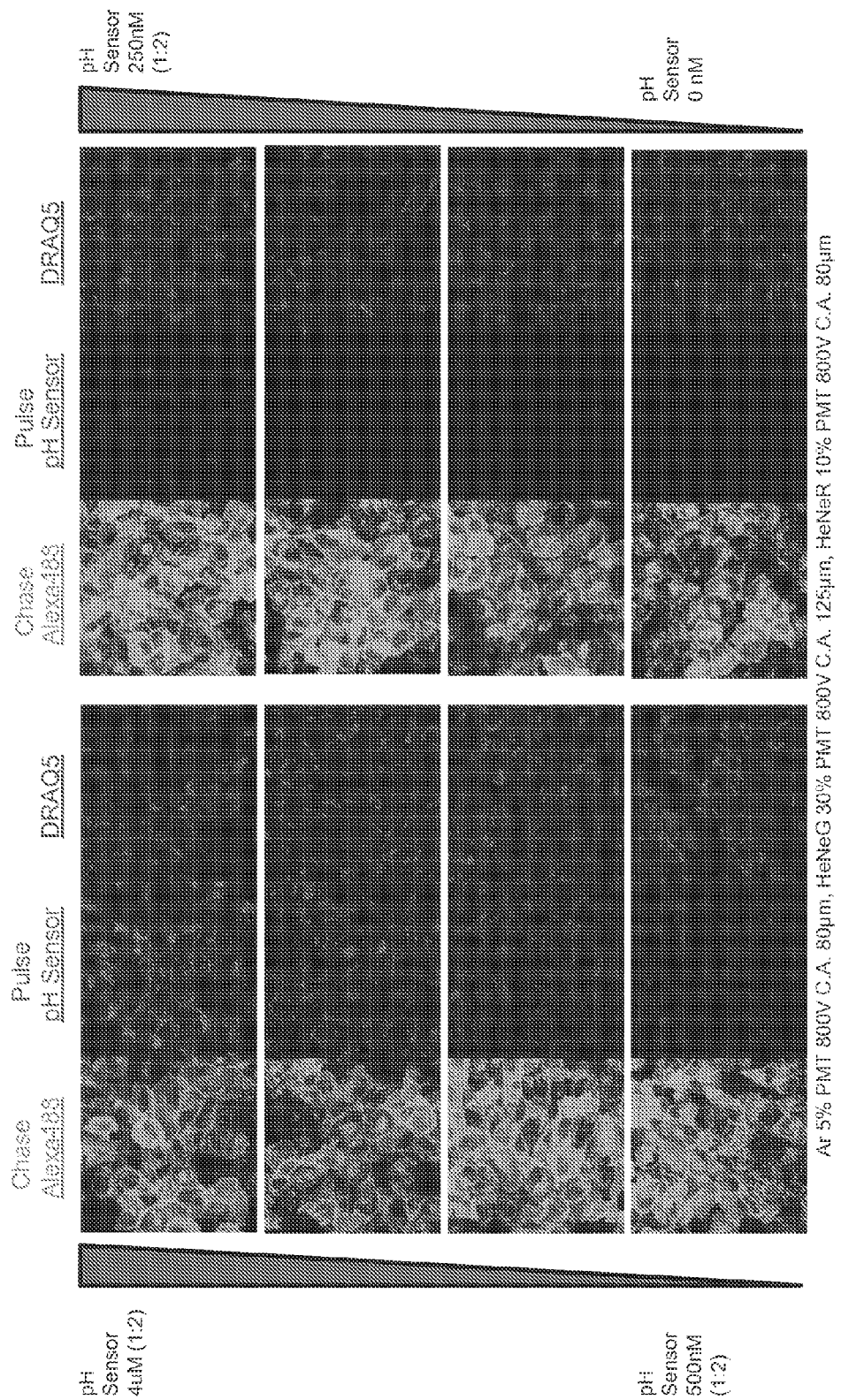
FIG. 32 shows the brightness of pH sensor PBI-4994 after agonist stimulation in U2-OS HaloTag-EDG1 stable cell line.
Figure 33:
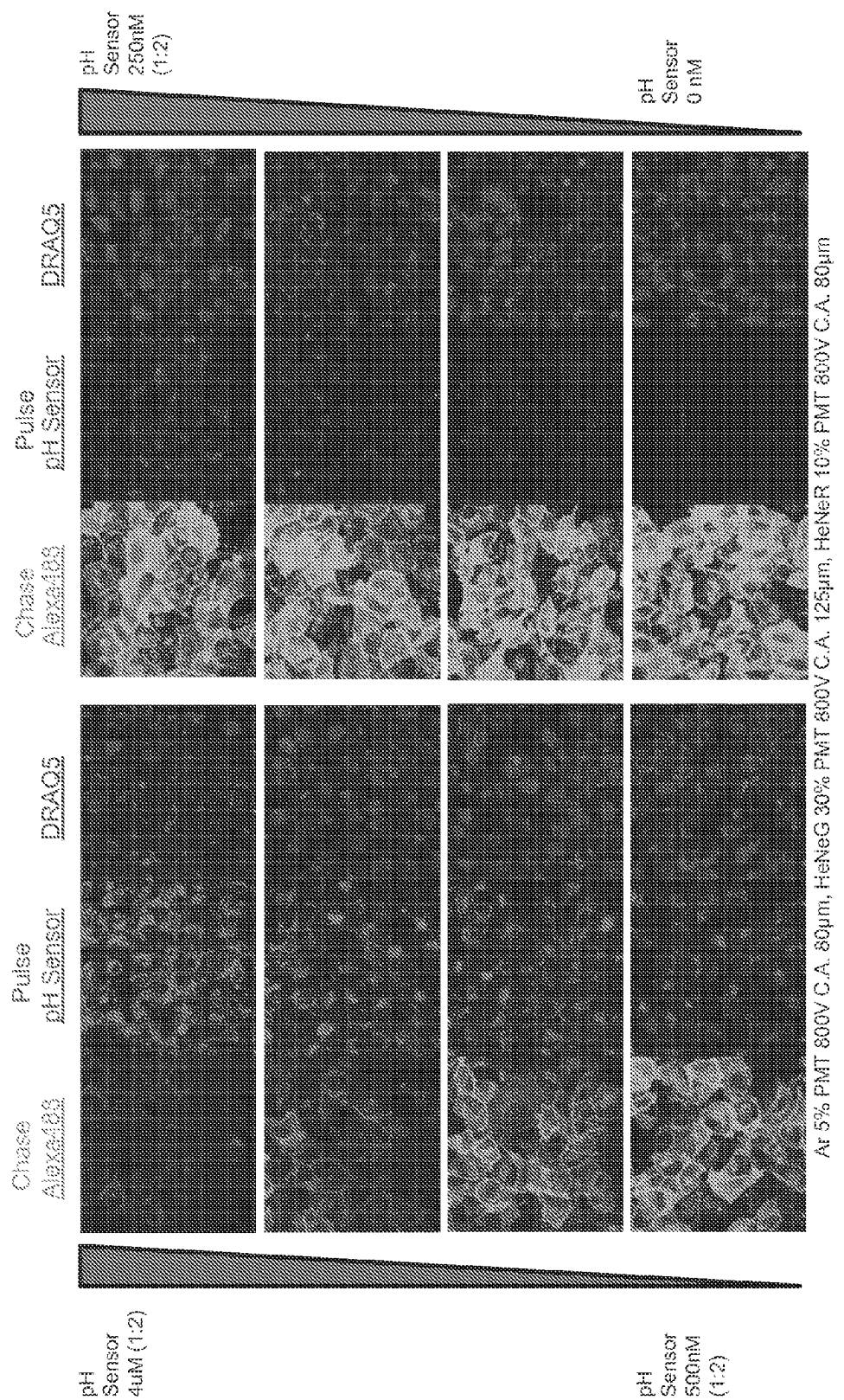
FIG. 33 shows the brightness of pH sensor PBI-4995 after agonist stimulation in U2-OS HaloTag-EDG1 stable cell line.
Figure 34:
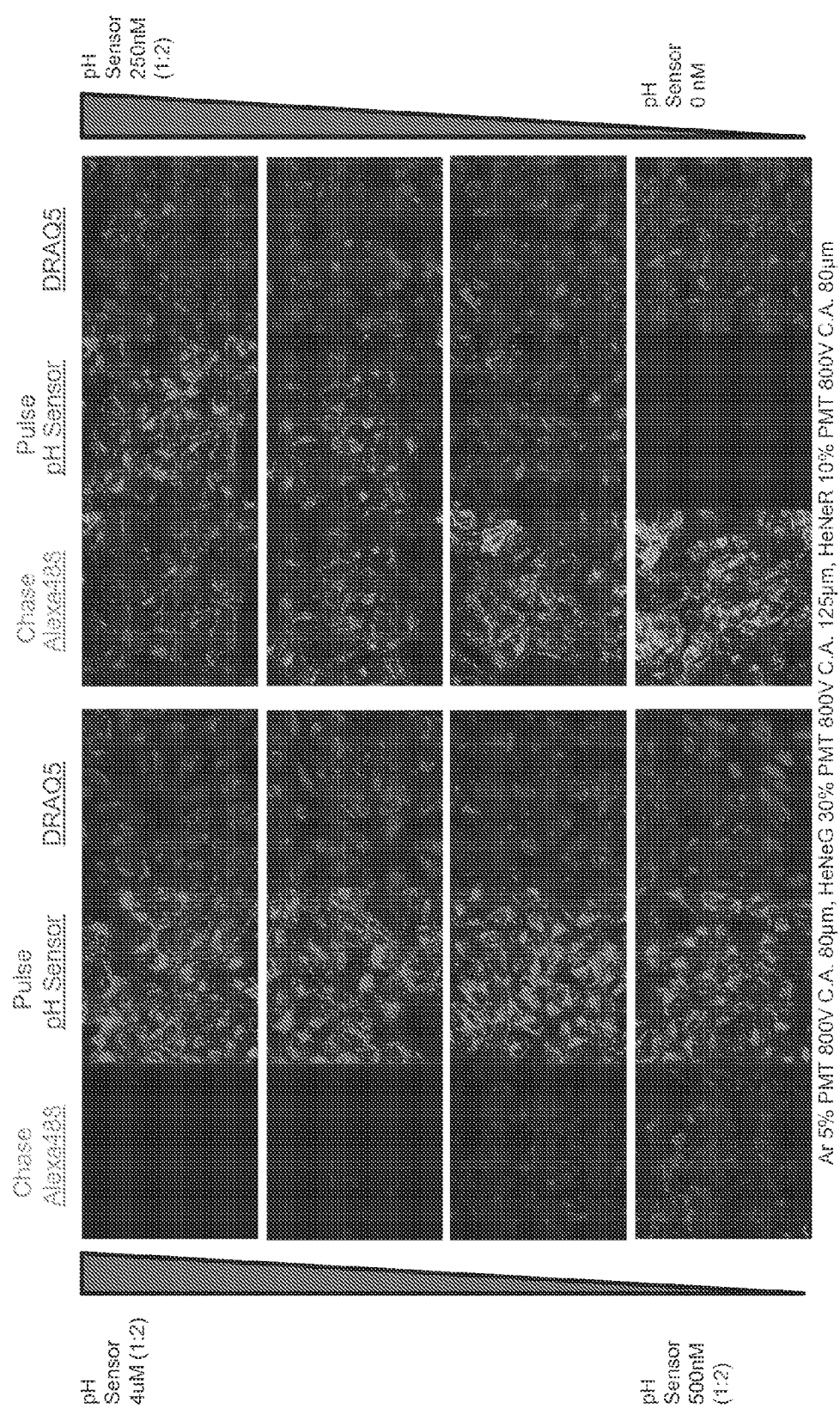
FIG. 34 shows the brightness of pH sensor PBI-5004 after agonist stimulation in U2-OS HaloTag-EDG1 stable cell line.
Figure 35:
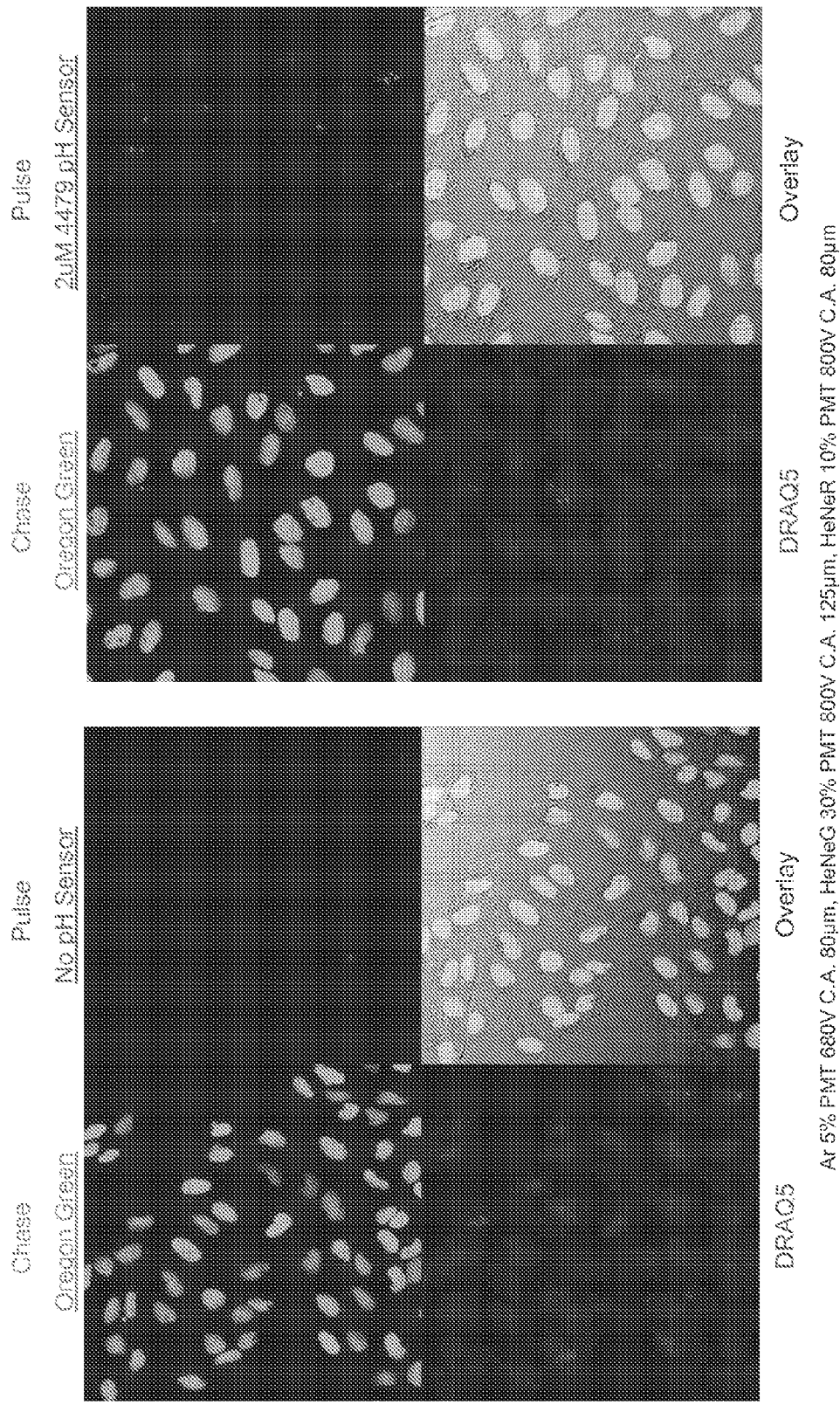
FIG. 35 shows the non-permeability of pH sensor PBI-4479 in U2-OS cells stably expressing HaloTag-NLS.
Figure 36:
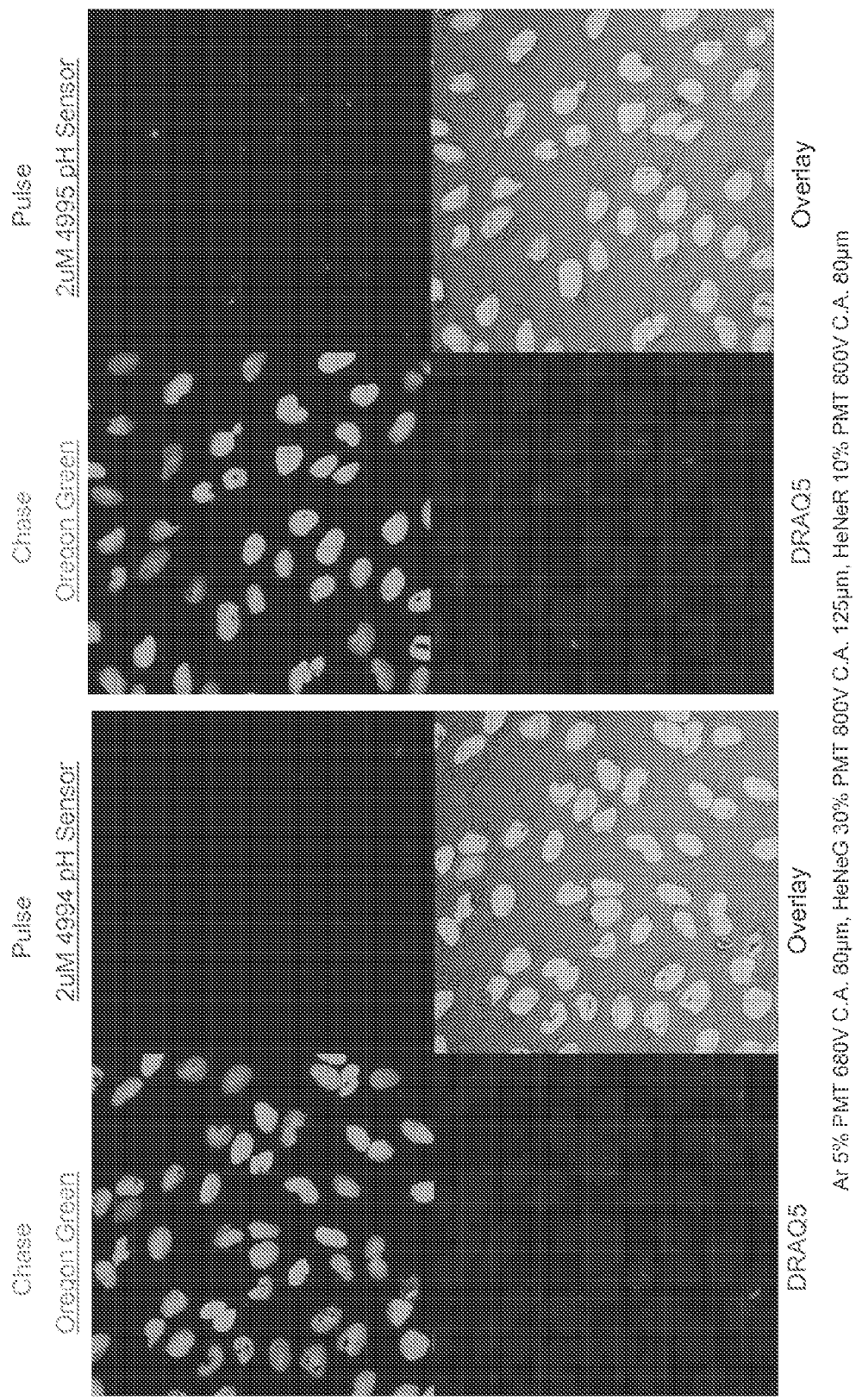
FIG. 36 shows the non-permeability of pH sensors PBI-4994 and PBI-4995 in U2-OS cells stably expressing HaloTag-NLS.
Figure 37:
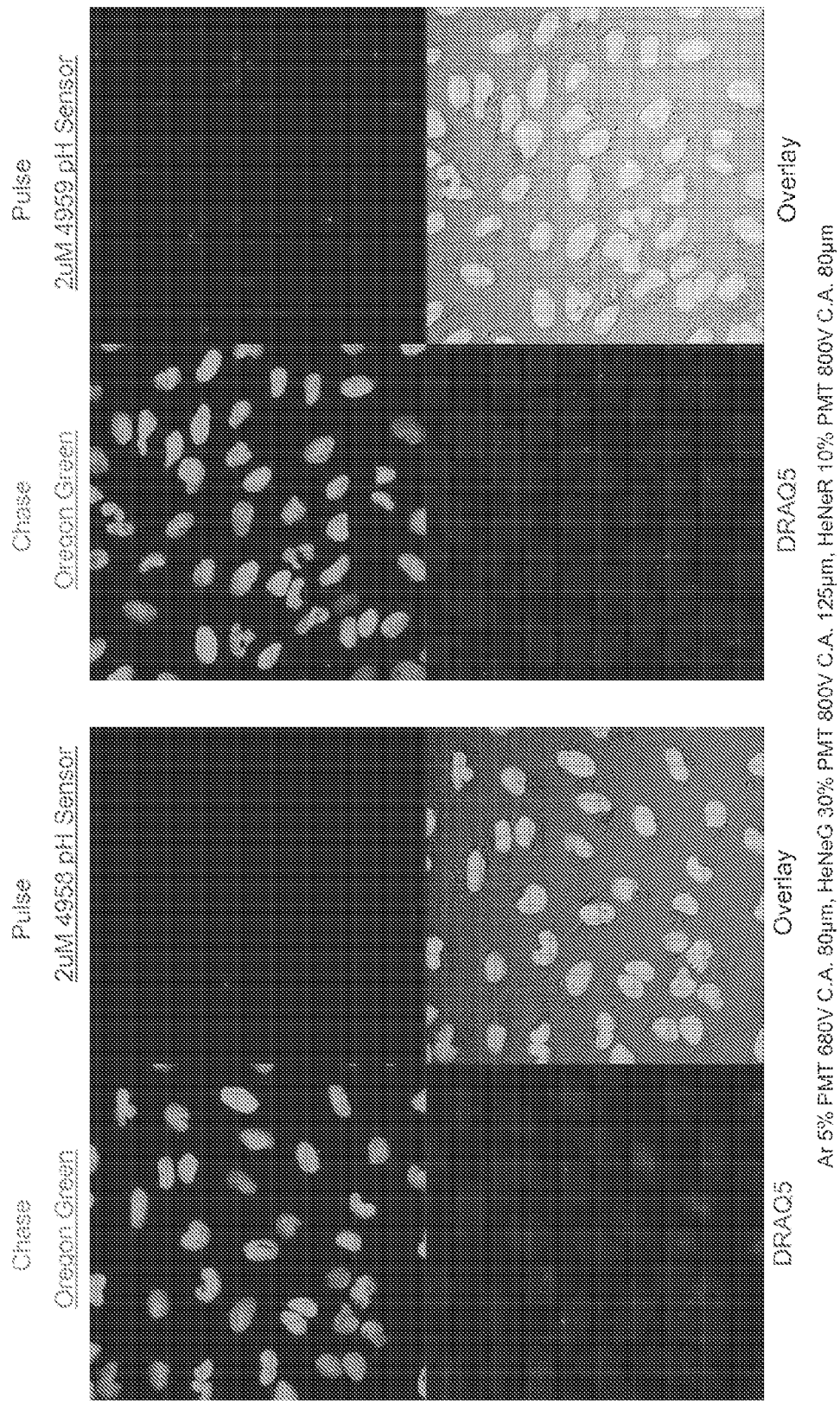
FIG. 37 shows the non-permeability of pH sensors PBI-4958 and PBI-4959 in U2-OS cells stably expressing HaloTag-NLS.
Figure 38:
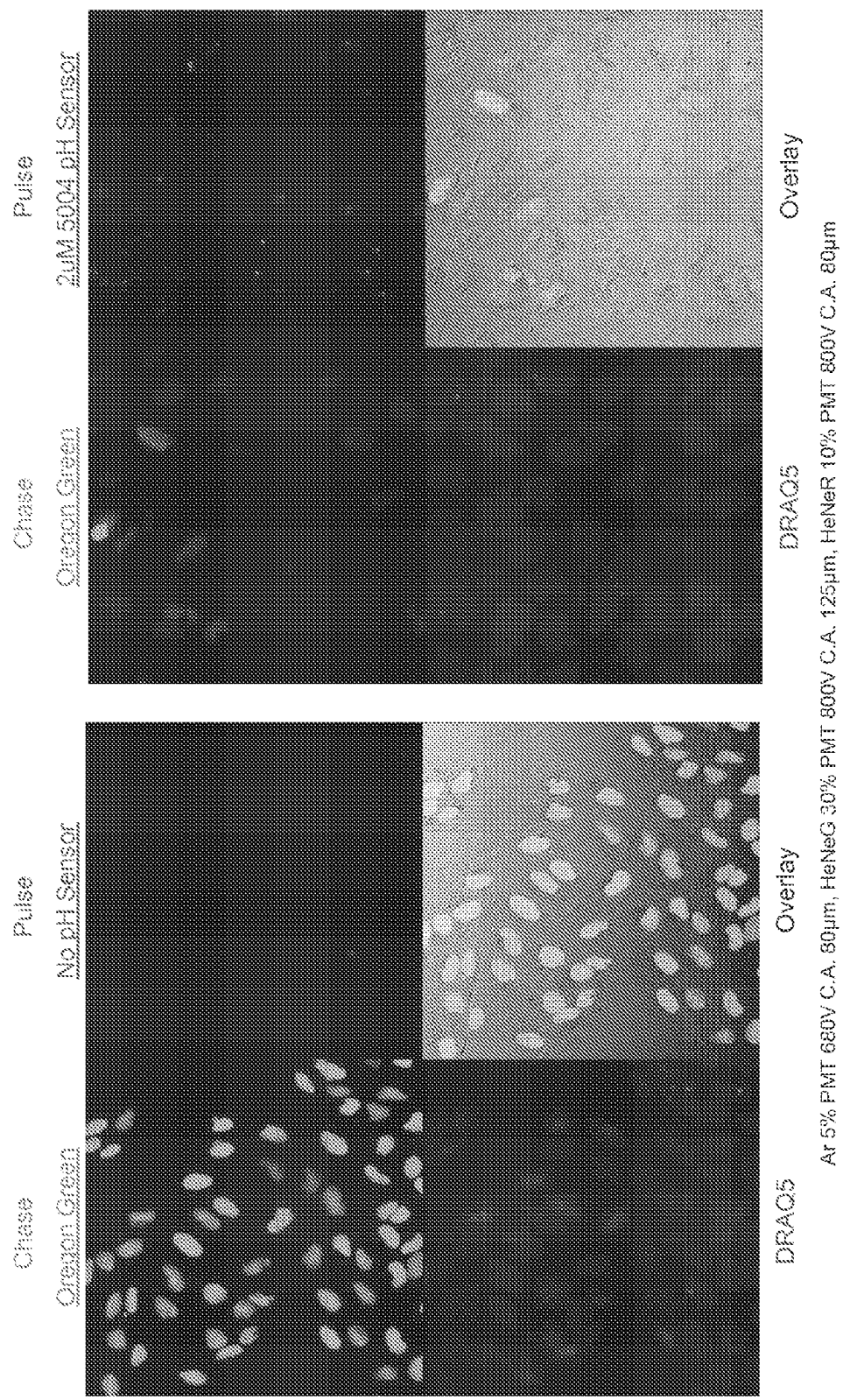
FIG. 38 shows the permeability of pH sensor PBI-5004 in U2-OS cells stably expressing HaloTag-NLS.
Figure 39:
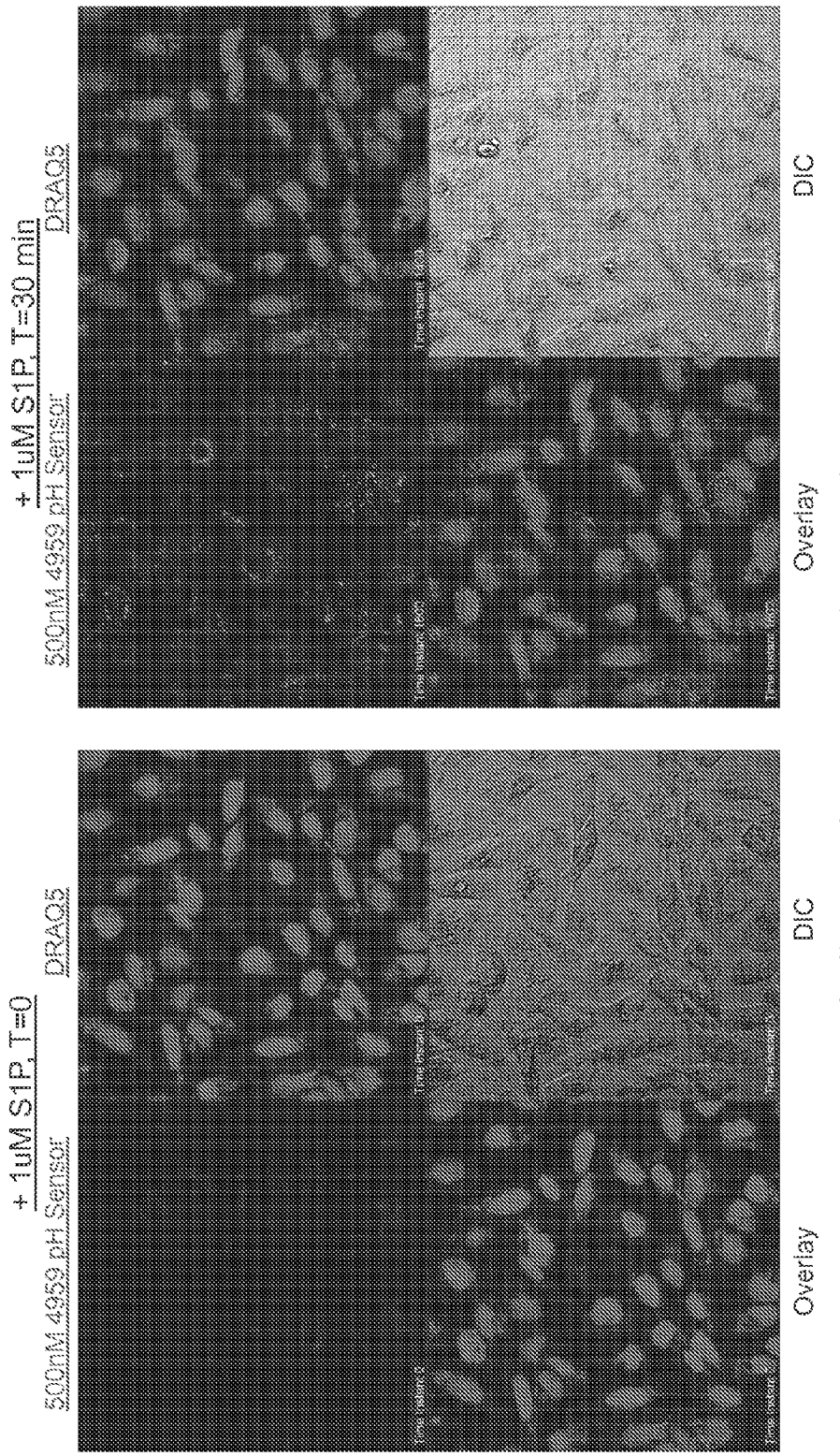
FIG. 39 shows the ability to detect internalization of HaloTag-EDG1 using the cell impermeable pH sensor PBI-4959 with 1 uM S1P.
Figure 40:
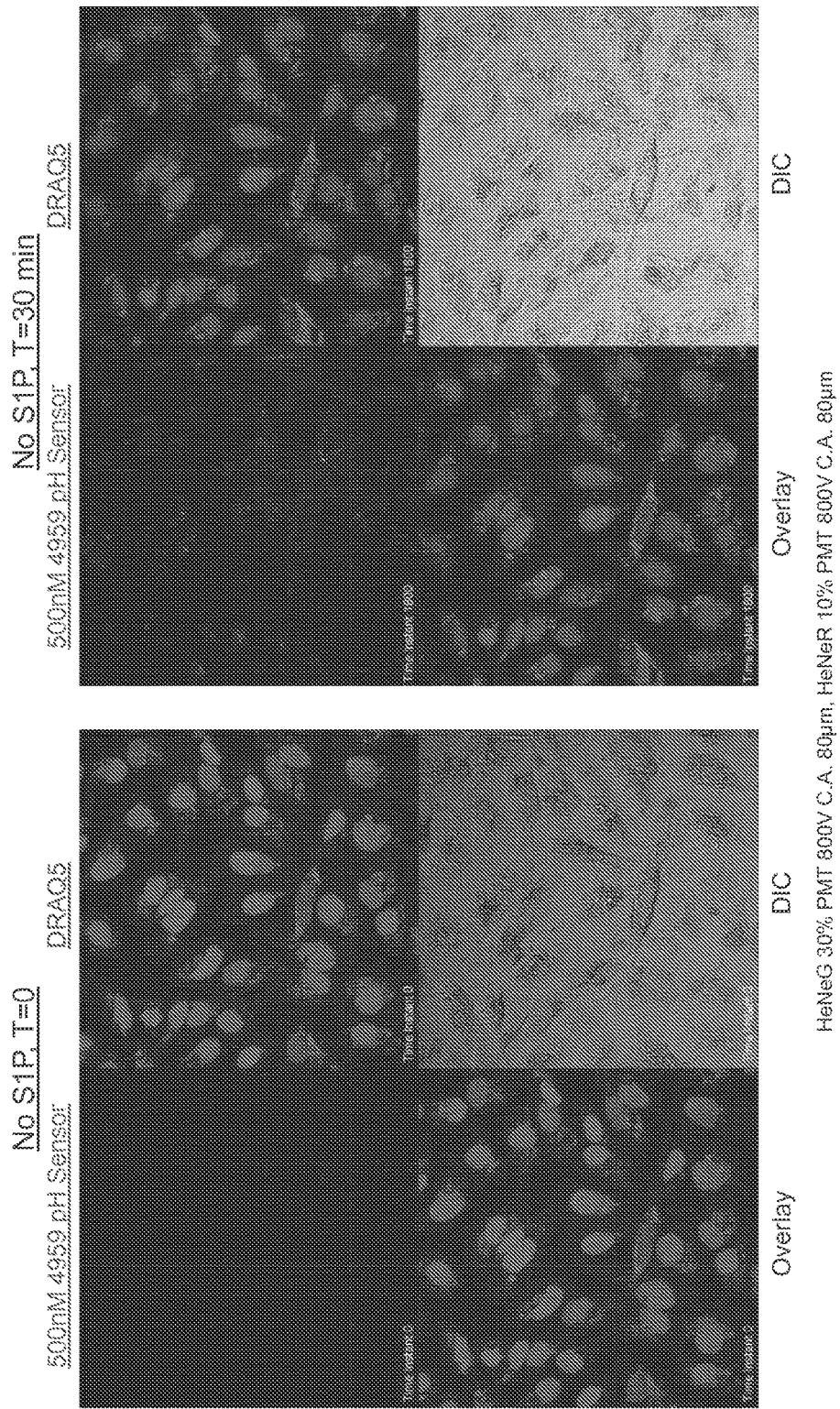
FIG. 40 shows the ability to detect background internalization of HaloTag-EDG1 using the cell impermeable pH sensor PBI-4959 without 1 uM S1P.
Figure 41:
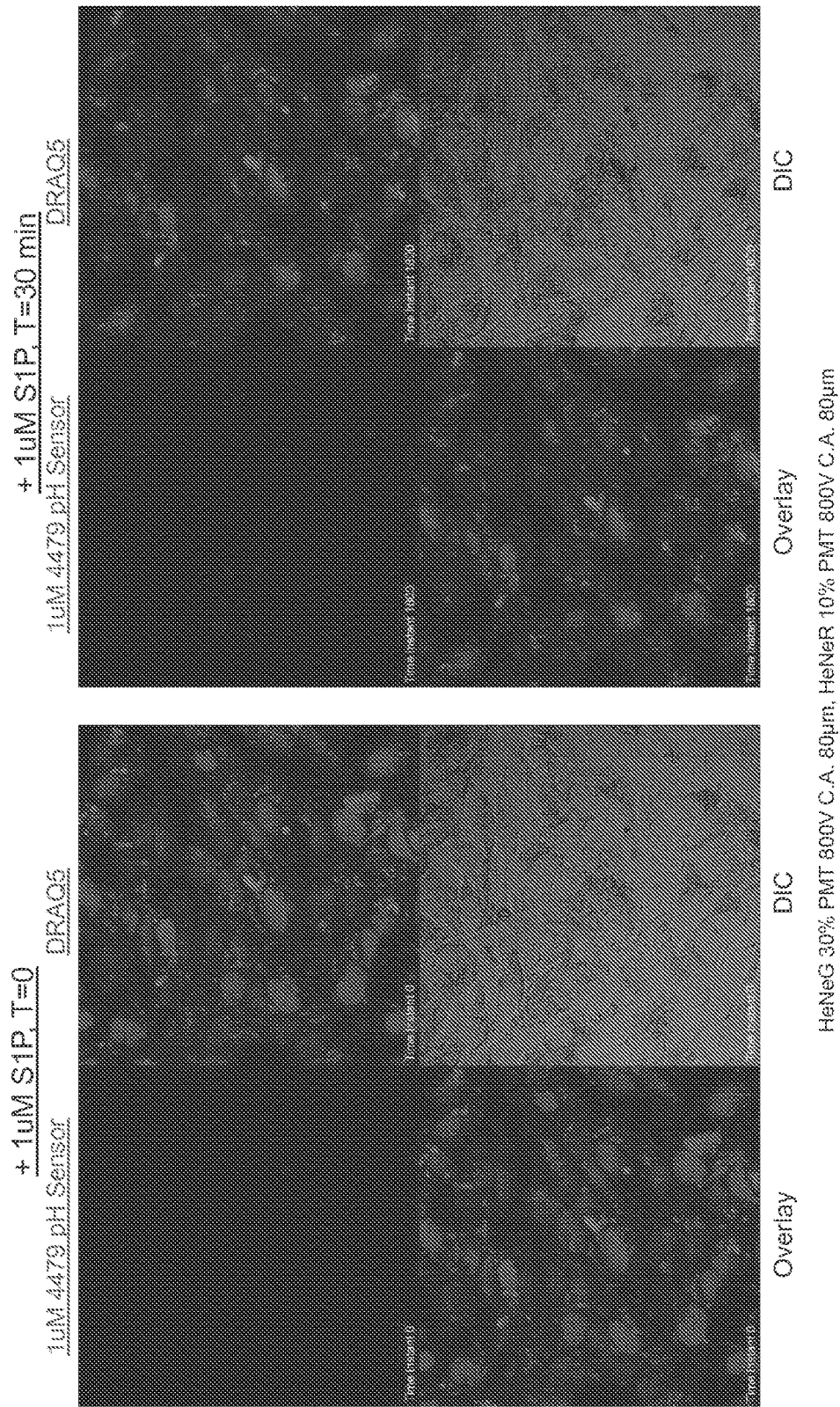
FIG. 41 shows the ability to detect internalization of HaloTag-EDG1 using the cell impermeable pH sensor PBI-4979 with 1 uM S1P.
Figure 42:
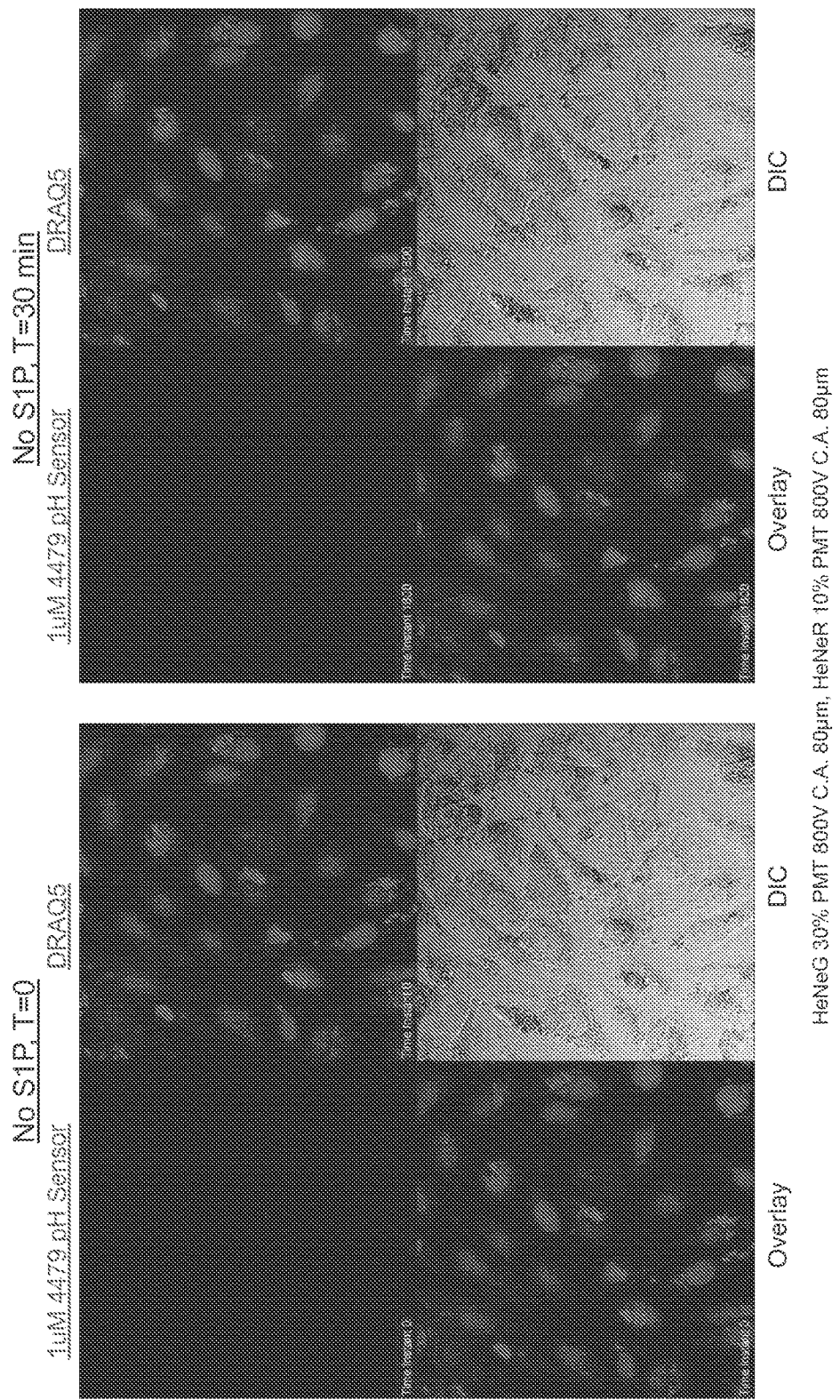
FIG. 42 shows the ability to detect background internalization of HaloTag-EDG1 using the cell impermeable pH sensor PBI-4959 without 1 uM S1P.

To demonstrate the specificity, U2-OS cells were exposed to PBI-4959, PBI-4958 and PBI-4479. U2-OS cells were plated at 40,000 cells/well into wells of an 8-well Lab-Tek® II chambered coverglass system and incubated overnight at 37° C./5% $CO_2$. The next day, the cells were labeled with 2 uM PBI-4959, PBI-4958, PBI-4479, PBI-4994, PBI-4995 or PBI-5004+500 nM DRAQ5 for 15 minutes at 37° C./5% $CO_2$. The cells were then washed three times with McCoy's 5A+0.5% cFBS and incubated at 37° C./5% $CO_2$ for 10 minutes. Images were acquired sequentially on Olympus FV500 37° C./5% $CO_2$. FIG. 22 demonstrates that there is no non-specific binding of the pH sensors in the wild-type U2-OS cells.

Example 11

Further Evaluation of the pH Sensors

To further evaluate the degree of labeling, background, binding efficiency, and brightness of the pH sensors, U2-OS cells were exposed to PBI-4449, PBI-4958, PBI-4959, PBI-4994, PBI-4995 or PBI-5004. U2-OS HaloTag™-EDG1 (Promega Corporation) cells were plated at 40,000 cells/well into an 8-well Lab-Tek® II chambered coverglass system and incubated overnight at 37° C./5% $CO_2$. The next day, the media was replaced with McCoy's 5A+0.5% cFBS and incubated overnight at 37° C./5% $CO_2$. After incubation, the cells were pulsed with PBI-4449, PBI-4958, PBI-4959, PBI-4994, PBI-4995 or PBI-5004 (0-4 uM serially diluted 1:2) for 10 minutes at 37° C./5% $CO_2$. The unbound pH sensor was removed from the cells and chased with 1 uM HaloTag™ Alexa488+500 nM DRAQ5 for 10 minutes at 37° C./5% $CO_2$. The cells were then washed three times with McCoy's 5A+0.5% cFBS and incubated at 37° C./5% $CO_2$ for 10 minutes. 1 uM S1P (Sphingosine-1-Phosphate) was then added to the cells, and images were acquired sequentially on Olympus FV500 37° C./5% $CO_2$. FIGS. 23-28 demonstrate the degree of labeling and background of the pH sensors tested at t=0 minutes. FIGS. 29-34 demonstrate the brightness of the pH sensors at t=20 minutes with S1P.

Example 12 pH Sensor Permeability

To evaluate permeability of the pH sensors, U2-OS cells were exposed to PBI-4479, PBI-4958, PBI-4959, PBI-4994, PBI-4995 or PBI-5004. U2-OS HaloTag®-NLS (Promega Corporation) cells were plated at 40,000 cells/well into wells of an 8-well Lab-Tek® II chambered coverglass system and incubated overnight at 37° C./5% CO2. The next day, the cells were pulsed with 2 uM PBI-4449, PBI-4958, PBI-4959, PBI-4994, PBI-4995 or PBI-5004 for 10 minutes at 37° C./5% $CO_2$. The pH sensor was then removed from the cells and chased with 1 uM HaloTag® Oregon Green (Promega Corporation)+500 nM DRAQ5 for 10 minutes at 37° C./5% $CO_2$. The cells were then washed three times with McCoy's 5A, and images were acquired sequentially on Olympus FV500 37° C./5% $CO_2$. FIGS. 35-38 demonstrate the permeability or non-permeability of the pH sensors tested.

Example 13

Detection of Internalization Using the pH Sensors

To evaluate internalization using an impermeable pH Sensor, U2-OS HaloTag®-EDG1 cells (Promega Corporation) were exposed to PBI-4479, PBI-4958, PBI-4959, PBI-4994 or PBI-4995 and internalization of HaloTag®-EDG1 assessed. U2-OS HaloTag®-EDG1 cells were plated at 40,000 cells/well into wells of an 8-well Lab-Tek® II chambered coverglass system and incubated overnight at 37° C./5% $CO_2$. The next day, the media was replaced with McCoy's 5A+0.5% cFBS and incubated overnight at 37° C./5% $CO_2$. After incubation, the cells were pulsed with 500 nM PBI-4479, PBI-4958, PBI-4959, PBI-4994 or PBI- 4995+500 nM DRAQ5 for 10 minutes at 37° C./5% $CO_2$. The cells were then washed three times with McCoy's 5A+0.5% cFBS and incubated at 37° C./5% $CO_2$ for 10 minutes. 1 uM S1P (Sphingosine-1-Phosphate) or carrier (DMSO) was then added to the cells, and images were acquired sequentially on Olympus FV500 at 37° C./5% CO2. FIGS. 39-42 demonstrate the ability to detect receptor internalization and background using the impermeable pH sensors tested.

Figure 43:
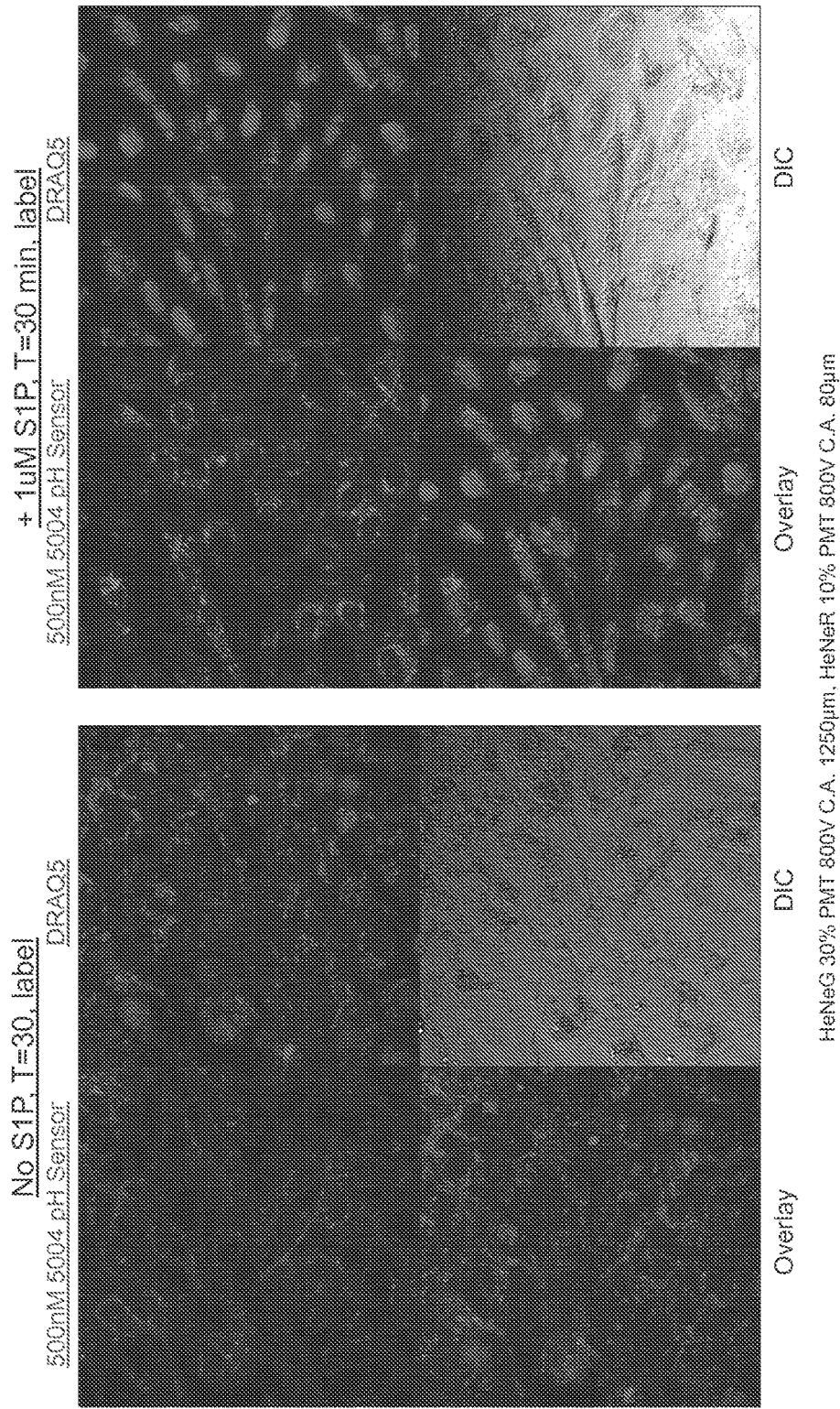
FIG. 43 shows the ability to detect internalization of HaloTag-EDG1 using the cell permeable pH sensor PBI-5004 after stimulation with or without 1 uM S1P.

To evaluate internalization using a permeable pH Sensor, U2-OS HaloTag®-EDG1 cells (Promega Corporation) were exposed to PBI-5004 and internalization of HaloTag®-EDG1 assessed. U2-OS HaloTag®-EDG1 (Promega Corporation) cells were plated at 40,000 cells/well into wells of an 8-well Lab-Tek® II chambered coverglass system and incubated overnight at 37° C./5% $CO_2$. The next day, the media was replaced with McCoy's 5A+0.5% cFBS and incubated overnight at 37° C./5% $CO_2$. After incubation, 1 uM S1P (Sphingosine-1-Phosphate) was added, and the cells incubated for 30 minutes at 37° C./5% $CO_2$. The cells were then labeled with 500 nM PBI-5004+500 nM DRAQ5 for 10 minutes at 37° C./5% $CO_2$. The cells were then washed three times with McCoy's 5A+0.5% cFBS, and images were acquired sequentially on Olympus FV500 37° C./5% $CO_2$. FIG. 43 demonstrates the ability to detect receptor internalization after stimulation using the cell permeable pH sensor tested.

Example 14

FACS Detection Using the pH Sensors

To demonstrate use in FACS detection, U2-OS or U2-OS HaloTag-ECS (Extra-Cellular Surface displayed HaloTag) were plated at 500,000 cells/well into wells of a 6-well plate in complete media+0.5% cFBS and incubated for 18 hours at 37° C./5% $CO_2$. After incubation, the cells were labeled with 1 uM impermeable pH sensor PBI-4479 for 15 minutes at 37° C./5% CO2. The cells were then washed three times with complete media+0.5% cFBS and incubated for 1 hour at 37° C./5% $CO_2$. The cells were then collected and resuspended in PBS, filtered, and sorted on Guava (Ex 546/560 nm).

FIGS. 44-45 demonstrate that the pH sensors of the present invention can be used in FACS detection. Cells that display HaloTag on the surface will bind the pH sensor. After 1 hour, internalization is observed by increase in pH sensor fluorescence in early endosome, late endosome, lysosome, or acidic compartment.

Example 15

Fluorescence Intensity Loss and Recovery of PBI-4479 when Titrated with Base and Acid This example was performed to determine if fluorescence intensity of a pH sensor of the present invention, PBI-4479, which is mostly fluorescent at pH 4, could be recovered when titrated to basic pH, then back to acidic pH. In order to limit disruption of the concentration of the sensor, the experiment was run in a large volume, and the pH was adjusted dropwise with a concentrated base, then with an acid. The product was first dissolved in DMSO to create a concentrated stock, and then a small amount was diluted into 100 mL 10 mM sodium phosphate buffer pH 4.0. Fluorescence was recorded on a HoribaJobinYvon Fluorolog throughout the experiment using an excitation of 528 nm, and emission at 557 nm maintaining a slit width of 2 nm. Excitation and emission maxima were also determined for each aliquot in the event the fluorescence properties of the molecule changed. pH was monitored using a calibrated pH probe (Denver Instruments Model 215 pH meter). 1 mL aliquots were removed when the solution increased to approximately one pH unit, and fluorescence was measured using the parameters stated above. The solution was first titrated dropwise with 2N sodium hydroxide while stirring, until a pH of approximately 8 was attained. The solution was then titrated down with 4N hydrochloric acid until a pH of approximately 4 was attained.

Figure 46:
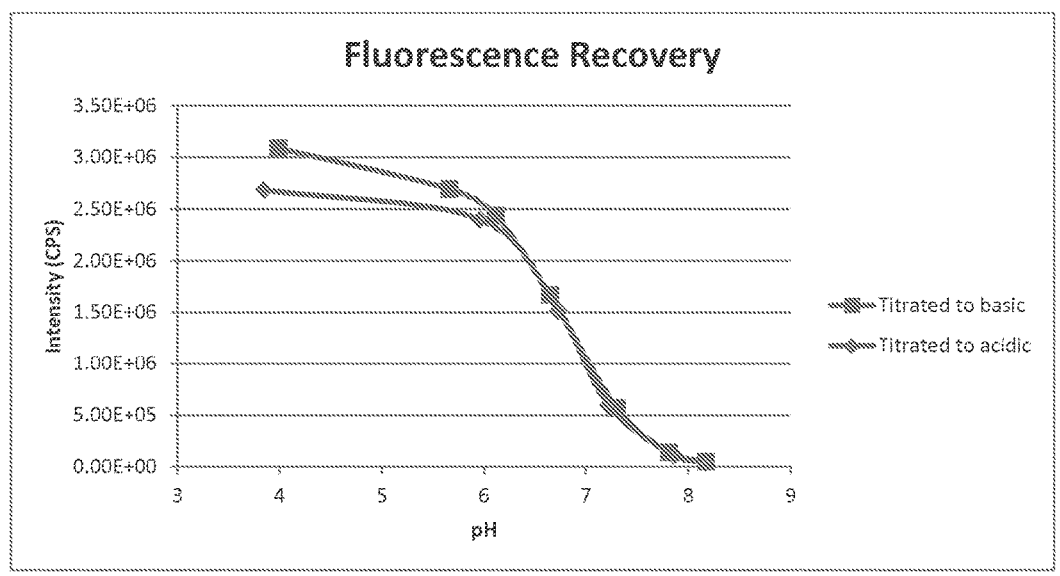
FIG. 46 shows the fluorescent intensity loss and recovery of a single sample of PBI-4479 when titrated with base and acid.

FIG. 46 demonstrates the fluorescent intensity loss and recovery of a single sample of PBI-4479 when titrated with base and acid. This further demonstrates that the pH sensors of the present invention can be used to monitor GPCR trafficking into the cell (increase in signal) as well as GPCR recycling (loss of signal). In general, the pH sensor of the present invention can be used to monitor environmental pH flux by gain/loss of signal.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A pH sensor agent comprising:

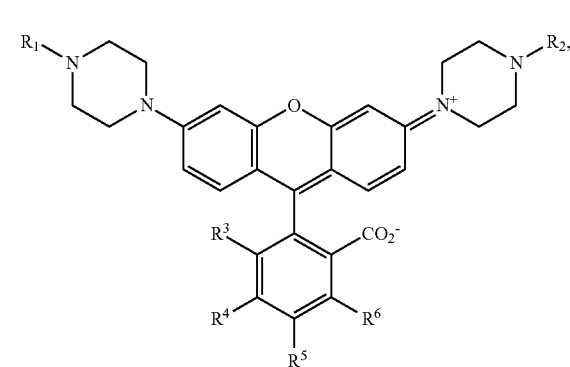

wherein R1 and R2 are independently alkyl sulfonic acids, and wherein R3-R6 are independently: H, F, Cl, Br, I, OH, an alkoxide group, an alkyl group, a heteroalkyl group, an aryl group, $CO_2H$, $SO_3H$, L-$CO_2H$, L-$SO_3H$, L-W, or L-CS; wherein L is a linear, branched, and/or cyclic covalent linkage comprising 0-16 non-hydrogen atoms and comprising any suitable combination of: ester, acid, sulphonic acid, sulfamide, amine, amide, alcohol, ether, thioether, halide, single bonds, double bonds, triple bonds, and aromatic bonds; wherein W is a reactive group; wherein X is: O, $CR_{17}$, $MR_{17}$; wherein $R_{17}$ is: H, F, Cl, Br, I, OH, an alkoxide group, an alkyl group, an aryl group, $CO_2H$, $SO_3H$, L-$CO_2H$, L-$SO_3H$, L-Y, or L-CS; and wherein M is selected from C, N, O, Si, P, S, Ge, As, Se, Sn, Sb, Te, Pb, Bi, and Po.

2. The pH sensor agent of claim 1, wherein R1 and R2 are $CH_2(CH_2)_nSO_3^-$, wherein n=0-25.

3. A composition comprising an entity of interest tethered to a pH sensor agent of claim 1.

4. A method of detecting the pH of an environment comprising:
   a) contacting a pH sensor agent of claim 1 to said environment;
   b) detecting fluorescence from said pH sensor agent; and
   c) correlating said fluorescence to said pH.

5. A method of monitoring changes in the pH of an environment comprising:
   a) contacting a pH sensor agent of claim 1 with said environment;
   b) detecting fluorescence from said pH sensor agent over time; and
   c) correlating changes in fluorescence to changes in pH.

6. A method of detecting movement of an entity of interest from a first pH environment to a second pH environment comprising:
   a) contacting a pH sensor agent of claim 1 to said first pH environment;
   b) detecting fluorescence of said pH sensor agent in said first pH environment;
   c) monitoring said fluorescence of said pH sensor agent, wherein a change in said fluorescence indicates movement of said pH sensor agent to a second pH environment.

7. The pH sensor agent of claim 2, wherein n=1-6.

8. The pH sensor of claim 7, wherein R1 and R2 are alkyl sulfonic acids of the same length.

9. The pH sensor of claim 7, wherein R1 and R2 are butyl sulphonic acid sulfonic acid.

10. The pH sensor of claim 7, wherein R3, R5, and R6 are hydrogen.

11. The pH sensor of claim 10, comprising a compound of:

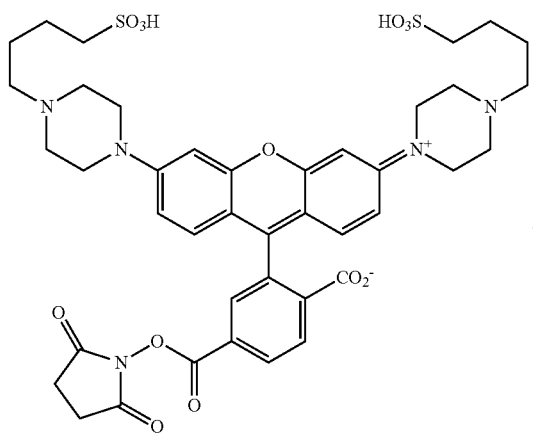

12. The pH sensor of claim 10, comprising a compound of:

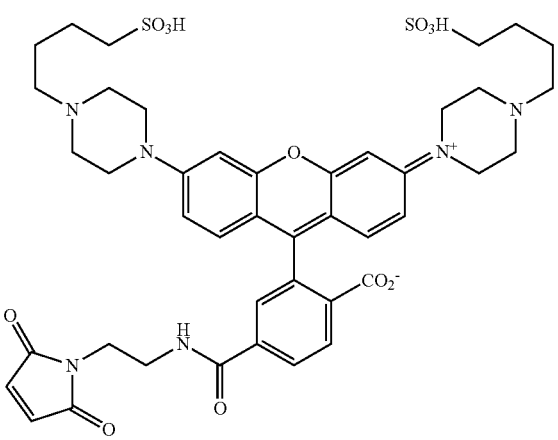

* * * * *